(12) United States Patent
Hull et al.

(10) Patent No.: US 11,542,815 B2
(45) Date of Patent: Jan. 3, 2023

(54) DETERMINING EFFECT OF OXIDATIVE HYDRAULIC FRACTURING

(71) Applicant: Saudi Arabian Oil Company, Dhahran (SA)

(72) Inventors: Katherine Leigh Hull, Houston, TX (US); Younane N. Abousleiman, Norman, OK (US); Dung Phan, Brookshire, TX (US); Khalid AlRuwaili, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 47 days.

(21) Appl. No.: 17/107,428

(22) Filed: Nov. 30, 2020

(65) Prior Publication Data

US 2022/0170365 A1 Jun. 2, 2022

(51) Int. Cl.
| | |
|---|---|
| *E21B 49/00* | (2006.01) |
| *E21B 43/26* | (2006.01) |
| *E21B 47/10* | (2012.01) |
| *E21B 49/02* | (2006.01) |
| *G01N 15/08* | (2006.01) |
| *G01N 33/24* | (2006.01) |
| *G01V 99/00* | (2009.01) |

(52) U.S. Cl.
CPC ............. *E21B 49/00* (2013.01); *E21B 43/26* (2013.01); *E21B 47/10* (2013.01); *G01N 15/08* (2013.01); *G01N 33/24* (2013.01); *E21B 49/02* (2013.01); *G01N 2015/0846* (2013.01); *G01V 99/005* (2013.01)

(58) Field of Classification Search
CPC ...... E21B 43/243; E21B 43/24; E21B 43/247; E21B 43/168; E21B 43/30; E21B 43/26
See application file for complete search history.

(56) References Cited

U.S. PATENT DOCUMENTS

| | | |
|---|---|---|
| 701,154 A | 5/1902 | Cole |
| 830,437 A | 9/1906 | Humphrey |
| 2,688,369 A | 9/1954 | Broyles |
| 2,699,212 A | 1/1955 | Dismukes |

(Continued)

FOREIGN PATENT DOCUMENTS

| | | |
|---|---|---|
| CA | 2322118 | 12/2007 |
| CA | 2635868 | 12/2008 |

(Continued)

OTHER PUBLICATIONS

PCT International Search Report and Written Opinion in International Appln. No. PCT/US2021/061006, dated Mar. 18, 2022, 16 pages.

(Continued)

*Primary Examiner* — Zakiya W Bates
(74) *Attorney, Agent, or Firm* — Fish & Richardson P.C.

(57) ABSTRACT

Estimating permeability enhancement of a subterranean formation due to presence of an oxidizer in a fracturing fluid, including determining kerogen volume percent in the subterranean formation and estimating fractured kerogen porosity, wherein the fractured kerogen porosity is associated with presence of the oxidizer. The technique includes determining an increase in connected porosity in the subterranean formation correlative with the kerogen vol % and the fractured kerogen porosity.

9 Claims, 12 Drawing Sheets

(56) References Cited

U.S. PATENT DOCUMENTS

| | | |
|---|---|---|
| 2,758,653 A | 8/1956 | Desbrow |
| 2,900,269 A | 8/1959 | Bauman et al. |
| 3,050,122 A | 8/1962 | Huitt et al. |
| 3,118,501 A | 1/1964 | Kenley |
| 3,211,221 A | 10/1965 | Huitt |
| 3,254,720 A | 8/1966 | Huitt |
| 3,284,281 A | 11/1966 | Thomas |
| 3,313,348 A | 4/1967 | Huitt et al. |
| 3,316,965 A | 5/1967 | Watanabe |
| 3,331,439 A | 7/1967 | Lawrence |
| 3,456,183 A | 7/1969 | Codrington et al. |
| 3,616,855 A | 11/1971 | Colgate |
| 3,690,622 A | 9/1972 | Brunner et al. |
| 3,716,387 A | 2/1973 | Simmons et al. |
| 3,807,557 A | 4/1974 | Miller |
| 3,834,122 A | 9/1974 | Allison et al. |
| 3,858,655 A | 1/1975 | Engle |
| 3,912,330 A | 10/1975 | Carnahan et al. |
| 3,926,575 A | 12/1975 | Meyers |
| 3,977,472 A | 8/1976 | Graham et al. |
| 3,996,062 A | 12/1976 | Frost |
| 4,043,599 A | 8/1977 | Lingane |
| 4,043,885 A | 8/1977 | Yen et al. |
| 4,047,988 A | 9/1977 | Weill |
| 4,195,010 A | 3/1980 | Russell et al. |
| 4,220,550 A | 9/1980 | Frenier et al. |
| 4,223,726 A | 9/1980 | Cha |
| 4,252,189 A | 2/1981 | Bodine |
| 4,262,745 A | 4/1981 | Stewart |
| 4,289,639 A | 9/1981 | Buske |
| 4,324,560 A | 4/1982 | Fonseca |
| 4,381,950 A | 5/1983 | Lawson |
| 4,390,067 A | 6/1983 | Willman |
| 4,444,058 A | 4/1984 | Ratigan |
| 4,480,696 A | 11/1984 | Almond et al. |
| 4,485,071 A | 11/1984 | Larter |
| 4,493,875 A | 1/1985 | Beck et al. |
| 4,587,739 A | 5/1986 | Holcomb |
| 4,594,170 A | 6/1986 | Brown et al. |
| 4,629,702 A | 12/1986 | Fan et al. |
| 4,640,692 A | 2/1987 | Audeh |
| 4,662,440 A | 5/1987 | Harmon |
| 4,681,914 A | 7/1987 | Olson et al. |
| 4,687,061 A | 8/1987 | Uhri |
| 4,708,805 A | 11/1987 | D'Muhala |
| 4,718,489 A | 1/1988 | Hallam et al. |
| 4,725,372 A | 2/1988 | Teot et al. |
| 4,735,731 A | 4/1988 | Rose et al. |
| 4,754,808 A | 7/1988 | Harmon |
| 4,780,223 A | 10/1988 | Baranet et al. |
| 4,809,793 A | 3/1989 | Hailey |
| 4,830,773 A | 5/1989 | Olson |
| 4,830,779 A | 5/1989 | Maeno et al. |
| 4,864,472 A | 9/1989 | Yoshimura |
| 4,882,128 A | 11/1989 | Hukvari et al. |
| 4,887,670 A | 12/1989 | Lord et al. |
| 4,974,675 A | 12/1990 | Austin et al. |
| 5,016,710 A | 5/1991 | Renard |
| 5,031,700 A | 7/1991 | McDougall et al. |
| 5,060,738 A | 10/1991 | Pittard et al. |
| 5,074,360 A | 12/1991 | Guinn |
| 5,111,881 A | 5/1992 | Soliman et al. |
| 5,180,556 A | 1/1993 | Nolte et al. |
| 5,193,396 A | 3/1993 | Gorski |
| 5,199,490 A | 4/1993 | Surles et al. |
| 5,203,413 A | 4/1993 | Zerhbouh |
| 5,213,705 A | 5/1993 | Olson |
| 5,224,543 A | 7/1993 | Watkins |
| 5,228,510 A | 7/1993 | Jennings, Jr |
| 5,232,490 A | 8/1993 | Bender et al. |
| 5,251,286 A | 10/1993 | Wiener et al. |
| 5,277,062 A | 1/1994 | Blanch et al. |
| 5,302,297 A | 4/1994 | Barthrope |
| 5,390,529 A | 2/1995 | Ghiselli |
| 5,435,187 A | 7/1995 | Ewy |
| 5,450,902 A | 9/1995 | Matthews |
| 5,517,854 A | 5/1996 | Plumb et al. |
| 5,551,516 A | 9/1996 | Norman et al. |
| 5,604,184 A | 2/1997 | Ellis et al. |
| 5,735,359 A | 4/1998 | Lee et al. |
| 5,757,473 A | 5/1998 | Kanduth et al. |
| 5,759,964 A | 6/1998 | Shuchart |
| 5,869,750 A | 2/1999 | Onan |
| 5,964,295 A | 10/1999 | Brown et al. |
| 5,999,887 A | 12/1999 | Giannakopoulos et al. |
| 6,035,936 A | 3/2000 | Whalen |
| 6,076,046 A | 6/2000 | Vasudevan et al. |
| 6,095,244 A | 8/2000 | Graham |
| 6,095,679 A | 8/2000 | Hammiche et al. |
| 6,119,776 A | 9/2000 | Graham et al. |
| 6,131,661 A | 10/2000 | Conner et al. |
| 6,138,760 A | 10/2000 | Lopez et al. |
| 6,140,816 A | 10/2000 | Heron et al. |
| 6,143,698 A | 11/2000 | Murphey et al. |
| 6,165,295 A | 12/2000 | Wagaman |
| 6,227,295 B1 | 5/2001 | Mitchell et al. |
| 6,258,859 B1 | 7/2001 | Dahayanake et al. |
| 6,306,800 B1 | 10/2001 | Samuel et al. |
| 6,349,595 B1 | 2/2002 | Lorenzo et al. |
| 6,399,546 B1 | 6/2002 | Chang et al. |
| 6,410,489 B1 | 6/2002 | Zhang et al. |
| 6,411,902 B1 | 6/2002 | Wiltshire |
| 6,425,448 B1 | 7/2002 | Zupanick |
| 6,435,277 B1 | 8/2002 | Qu et al. |
| 6,468,945 B1 | 10/2002 | Zhang |
| 6,482,866 B1 | 11/2002 | Dahayanake et al. |
| 6,488,087 B2 | 12/2002 | Longbottom |
| 6,488,091 B1 | 12/2002 | Weaver |
| 6,491,099 B1 | 12/2002 | Di Lullo Arias et al. |
| 6,491,425 B1 | 12/2002 | Hammiche et al. |
| 6,494,263 B2 | 12/2002 | Todd |
| 6,516,080 B1 | 2/2003 | Nur |
| 6,579,572 B2 | 6/2003 | Espin et al. |
| 6,605,570 B2 | 8/2003 | Miller et al. |
| 6,609,067 B2 | 8/2003 | Tare et al. |
| 6,652,682 B1 | 11/2003 | Fawls |
| 6,694,262 B2 | 2/2004 | Rozak |
| 6,705,398 B2 | 3/2004 | Weng |
| 6,715,553 B2 | 4/2004 | Reddy et al. |
| 6,729,394 B1 | 5/2004 | Hassan |
| 6,729,409 B1 | 5/2004 | Gupta et al. |
| 6,749,022 B1 | 6/2004 | Fredd |
| 6,776,235 B1 | 8/2004 | England |
| 6,831,108 B2 | 12/2004 | Dahanayake et al. |
| 6,832,158 B2 | 12/2004 | Mese |
| 6,843,233 B2 | 1/2005 | Berger et al. |
| 6,846,420 B2 | 1/2005 | Reddy et al. |
| 6,866,048 B2 | 3/2005 | Mattox |
| 6,875,728 B2 | 4/2005 | Gupta et al. |
| 6,881,709 B2 | 4/2005 | Nelson et al. |
| 6,884,760 B1 | 4/2005 | Brand et al. |
| 6,942,840 B1 | 9/2005 | Broderick |
| 6,947,843 B2 | 9/2005 | Fisher et al. |
| 6,989,391 B2 | 1/2006 | Funkhouser |
| 7,007,752 B2 | 3/2006 | Reddy et al. |
| 7,011,154 B2 | 3/2006 | Maher et al. |
| 7,044,220 B2 | 5/2006 | Nguyen et al. |
| 7,052,901 B2 | 5/2006 | Crews |
| 7,081,439 B2 | 7/2006 | Sullivan et al. |
| 7,086,484 B2 | 8/2006 | Smith |
| 7,098,663 B1 | 8/2006 | Bader |
| 7,148,185 B2 | 12/2006 | Fu et al. |
| 7,207,388 B2 | 4/2007 | Samuel et al. |
| 7,210,528 B1 | 5/2007 | Brannon et al. |
| 7,216,709 B2 | 5/2007 | McElfresh et al. |
| 7,255,169 B2 | 8/2007 | van Batenburg et al. |
| 7,261,158 B2 | 8/2007 | Middaugh et al. |
| 7,281,580 B2 | 10/2007 | Parker et al. |
| 7,281,581 B2 | 10/2007 | Nyuyen et al. |
| 7,291,651 B2 | 11/2007 | Chen et al. |
| 7,299,874 B2 | 11/2007 | Welton |
| 7,326,670 B2 | 2/2008 | DiLullo et al. |
| 7,334,635 B2 | 2/2008 | Nguyen |
| 7,334,636 B2 | 2/2008 | Nguyen |

(56) References Cited

U.S. PATENT DOCUMENTS

| | | |
|---|---|---|
| 7,341,980 B2 | 3/2008 | Lee et al. |
| 7,344,889 B2 | 3/2008 | Kelemen et al. |
| 7,369,980 B2 | 5/2008 | Deffenbaugh et al. |
| 7,370,696 B2 | 5/2008 | Al-Muraikhi |
| 7,373,977 B1 | 5/2008 | Berger et al. |
| 7,387,987 B2 | 6/2008 | Chen et al. |
| 7,419,005 B2 | 9/2008 | Al-Muraikhi |
| 7,424,911 B2 | 9/2008 | McCarthy et al. |
| 7,451,812 B2 | 11/2008 | Cooper et al. |
| 7,472,748 B2 | 1/2009 | Gdanski et al. |
| 7,472,751 B2 | 1/2009 | Brannon et al. |
| 7,491,444 B2 | 2/2009 | Smith et al. |
| 7,500,517 B2 | 3/2009 | Looney et al. |
| 7,513,306 B2 | 4/2009 | Pfefferle et al. |
| 7,521,400 B2 | 4/2009 | Samuel |
| 7,526,418 B2 | 4/2009 | Pita et al. |
| 7,527,097 B2 | 5/2009 | Patel |
| 7,544,643 B2 | 6/2009 | Huang |
| 7,565,831 B2 | 7/2009 | Miyahara |
| 7,571,767 B2 | 8/2009 | Parker et al. |
| 7,581,590 B2 | 9/2009 | Lesko et al. |
| 7,588,085 B2 | 9/2009 | Acock et al. |
| 7,595,284 B2 | 9/2009 | Crews |
| 7,615,517 B2 | 11/2009 | Huang et al. |
| 7,621,173 B2 | 11/2009 | Hsu |
| 7,635,844 B2 | 12/2009 | Joseph et al. |
| 7,637,316 B2 | 12/2009 | Best |
| 7,642,223 B2 | 1/2010 | Santra et al. |
| 7,645,724 B2 | 1/2010 | Crews |
| 7,645,883 B1 | 1/2010 | Hawkins et al. |
| 7,654,159 B2 | 2/2010 | Enoksson |
| 7,655,603 B2 | 2/2010 | Crews |
| 7,678,723 B2 | 3/2010 | Duenckel et al. |
| 7,703,531 B2 | 4/2010 | Huang |
| 7,770,647 B2 | 8/2010 | Watson et al. |
| 7,771,549 B1 | 8/2010 | Christe et al. |
| 7,789,164 B2 | 9/2010 | Looney et al. |
| 7,803,740 B2 | 9/2010 | Bicerano et al. |
| 7,803,744 B2 | 9/2010 | Chen et al. |
| 7,823,656 B1 | 11/2010 | Williams et al. |
| 7,825,053 B2 | 11/2010 | Duenckel et al. |
| 7,828,063 B2 | 11/2010 | Olsen et al. |
| 7,857,055 B2 | 12/2010 | Li |
| 7,867,613 B2 | 1/2011 | Smith et al. |
| 7,878,246 B2 | 2/2011 | Samuel et al. |
| 7,878,248 B2 | 2/2011 | Abad et al. |
| 7,887,918 B2 | 2/2011 | Smith et al. |
| 7,918,277 B2 | 4/2011 | Brannon et al. |
| 7,921,911 B2 | 4/2011 | Fuller et al. |
| 7,983,845 B2 | 7/2011 | Minh |
| 7,997,342 B2 | 8/2011 | Welton et al. |
| 8,003,212 B2 | 8/2011 | Smith et al. |
| 8,003,577 B2 | 8/2011 | Li et al. |
| 8,006,760 B2 | 8/2011 | Fleming et al. |
| 8,041,510 B2 | 10/2011 | Dasgupta |
| 8,047,288 B2 | 11/2011 | Skala et al. |
| 8,058,613 B2 | 11/2011 | Lou et al. |
| 8,061,424 B2 | 11/2011 | Willberg et al. |
| 8,066,068 B2 | 11/2011 | Lesko et al. |
| 8,081,802 B2 | 12/2011 | Dvorkin et al. |
| 8,104,536 B2 | 1/2012 | Looney et al. |
| 8,119,576 B2 | 2/2012 | Reyes et al. |
| 8,127,850 B2 | 3/2012 | Brannon et al. |
| 8,146,416 B2 | 4/2012 | Pisio et al. |
| 8,165,817 B2 | 4/2012 | Betancourt et al. |
| 8,177,422 B2 | 5/2012 | Kjoller et al. |
| 8,205,675 B2 | 6/2012 | Brannon et al. |
| 8,216,675 B2 | 7/2012 | Palamara et al. |
| 8,225,866 B2 | 7/2012 | Rouffignac et al. |
| 8,265,915 B2 | 9/2012 | Hsu et al. |
| 8,278,931 B2 | 10/2012 | Fang et al. |
| 8,352,228 B2 | 1/2013 | Walters et al. |
| 8,380,437 B2 | 2/2013 | Abousleiman et al. |
| 8,408,305 B2 | 4/2013 | Brannon et al. |
| 8,473,213 B2 | 6/2013 | Zhu et al. |
| 8,490,685 B2 | 7/2013 | Tolman |
| 8,490,700 B2 | 7/2013 | Lesko et al. |
| 8,606,524 B2 | 12/2013 | Soliman et al. |
| 8,614,157 B2 | 12/2013 | Pope et al. |
| 8,614,573 B2 | 12/2013 | Minh |
| 8,616,294 B2 | 12/2013 | Zubrin et al. |
| 8,631,872 B2 | 1/2014 | East |
| 8,636,065 B2 | 1/2014 | Lesko et al. |
| 8,653,011 B2 | 2/2014 | Samuel et al. |
| 8,701,788 B2 | 4/2014 | Wigand et al. |
| 8,729,903 B2 | 5/2014 | Srnka et al. |
| 8,731,889 B2 | 5/2014 | Du et al. |
| 8,757,259 B2 | 6/2014 | Lesko et al. |
| 8,763,699 B2 | 7/2014 | Medvedev et al. |
| 8,763,703 B2 | 7/2014 | Saini et al. |
| 8,778,852 B2 | 7/2014 | Huang |
| 8,796,187 B2 | 8/2014 | Reyes et al. |
| 8,821,806 B2 | 9/2014 | Hersherwitz et al. |
| 8,822,386 B2 | 9/2014 | Quintero et al. |
| 8,835,363 B2 | 9/2014 | Amanullah et al. |
| 8,839,860 B2 | 9/2014 | Wigand et al. |
| 8,844,366 B2 | 9/2014 | Warren |
| 8,851,177 B2 | 10/2014 | Wigand |
| 8,865,482 B2 | 10/2014 | Wang et al. |
| 8,868,385 B2 | 10/2014 | Fertig et al. |
| 8,883,693 B2 | 11/2014 | Eldred et al. |
| 8,936,083 B2 | 1/2015 | Nguyen |
| 8,936,089 B2 | 1/2015 | Wigand |
| 8,967,249 B2 | 3/2015 | Akkurt et al. |
| 9,006,151 B2 | 4/2015 | Amanullah et al. |
| 9,006,153 B2 | 4/2015 | Lin et al. |
| 9,033,033 B2 | 5/2015 | Thomas et al. |
| 9,033,043 B2 | 5/2015 | Hinkel |
| 9,046,509 B2 | 6/2015 | Dvorkin et al. |
| 9,057,797 B2 | 6/2015 | Omeragic et al. |
| 9,063,252 B2 | 6/2015 | Kamal |
| 9,080,440 B2 | 7/2015 | Panga et al. |
| 9,085,727 B2 | 7/2015 | Litvinets et al. |
| 9,097,818 B2 | 8/2015 | Hursan |
| 9,128,210 B2 | 9/2015 | Pomerantz |
| 9,133,398 B2 | 9/2015 | Wigand et al. |
| 9,152,745 B2 | 10/2015 | Glinsky |
| 9,187,992 B2 | 11/2015 | Cherian |
| 9,297,244 B2 | 3/2016 | Mahoney et al. |
| 9,523,268 B2 | 12/2016 | Potapenko et al. |
| 9,644,137 B2 | 5/2017 | Dean et al. |
| 9,664,018 B2 | 5/2017 | Vandeponseele et al. |
| 9,670,764 B2 | 6/2017 | Lesko et al. |
| 9,688,904 B2 | 6/2017 | Wang et al. |
| 9,696,270 B1 | 7/2017 | Roy et al. |
| 9,725,645 B2 | 8/2017 | Monastiriotis et al. |
| 9,753,016 B1 | 9/2017 | Daugela |
| 9,784,085 B2 | 10/2017 | Liu et al. |
| 9,784,882 B2 | 10/2017 | Vinegar et al. |
| 9,816,365 B2 | 11/2017 | Nguyen et al. |
| 9,834,721 B2 | 12/2017 | Chang et al. |
| 9,845,670 B2 | 12/2017 | Smjaatmadja et al. |
| 9,863,211 B2 | 1/2018 | Gamage et al. |
| 9,863,230 B2 | 1/2018 | Litvinets et al. |
| 9,863,231 B2 | 1/2018 | Hull et al. |
| 9,869,649 B2 | 1/2018 | Hull et al. |
| 9,885,691 B1 | 2/2018 | Daugela |
| 9,895,670 B2 | 2/2018 | Anders et al. |
| 9,896,919 B1 | 2/2018 | Chen |
| 9,902,898 B2 | 2/2018 | Nelson et al. |
| 9,909,404 B2 | 3/2018 | Hwang et al. |
| 9,927,344 B2 | 3/2018 | Chertov |
| 9,945,220 B2 | 4/2018 | Saini et al. |
| 9,995,125 B2 | 6/2018 | Madasu et al. |
| 9,995,220 B2 | 6/2018 | Hawie et al. |
| 10,001,769 B2 | 6/2018 | Huang et al. |
| 10,023,782 B2 | 7/2018 | Wang et al. |
| 10,030,495 B2 | 7/2018 | Litvinets et al. |
| 10,047,281 B2 | 8/2018 | Nguyen et al. |
| 10,066,149 B2 | 9/2018 | Li et al. |
| 10,077,396 B2 | 9/2018 | Nguyen et al. |
| 10,087,364 B2 | 10/2018 | Kaufman et al. |
| 10,113,396 B2 | 10/2018 | Nelson et al. |
| 10,151,715 B2 | 12/2018 | Hull et al. |

(56) References Cited

U.S. PATENT DOCUMENTS

| | | |
|---|---|---|
| 10,273,398 B2 | 4/2019 | Liu et al. |
| 10,329,478 B2 | 6/2019 | Schnoor et al. |
| 10,345,764 B2 | 7/2019 | Early et al. |
| 10,351,758 B2 | 7/2019 | Hull et al. |
| 10,379,068 B2 | 8/2019 | Hull et al. |
| 10,415,367 B2 | 9/2019 | Galford |
| 10,421,897 B2 | 9/2019 | Skiba et al. |
| 10,472,555 B2 | 11/2019 | Hutchins et al. |
| 10,479,927 B2 | 11/2019 | Hull et al. |
| 10,550,314 B2 | 2/2020 | Liang et al. |
| 10,611,967 B2 | 4/2020 | Inan |
| 10,612,355 B1 | 4/2020 | Alruwaili et al. |
| 10,753,190 B1 | 8/2020 | Schipper et al. |
| 10,781,360 B2 | 9/2020 | Hull et al. |
| 10,837,279 B2 | 11/2020 | Han et al. |
| 2002/0003115 A1 | 1/2002 | Conaway et al. |
| 2003/0093982 A1 | 5/2003 | Suwabe et al. |
| 2003/0209248 A1 | 11/2003 | Ward |
| 2003/0212465 A1 | 11/2003 | Howard et al. |
| 2004/0101457 A1 | 5/2004 | Pahlman et al. |
| 2004/0211567 A1 | 10/2004 | Aud |
| 2005/0039919 A1 | 2/2005 | Harris et al. |
| 2005/0059558 A1 | 3/2005 | Blanch |
| 2005/0060130 A1 | 3/2005 | Shapiro et al. |
| 2005/0103118 A1 | 5/2005 | Workman |
| 2005/0274523 A1 | 12/2005 | Brannon et al. |
| 2006/0047489 A1 | 3/2006 | Scheidt et al. |
| 2006/0084579 A1 | 4/2006 | Berger et al. |
| 2006/0092766 A1 | 5/2006 | Shelley et al. |
| 2006/0265204 A1 | 11/2006 | Wallis et al. |
| 2007/0051517 A1 | 3/2007 | Smjaatmadja et al. |
| 2007/0054054 A1 | 3/2007 | Svoboda et al. |
| 2007/0087940 A1 | 4/2007 | Qu et al. |
| 2007/0203677 A1 | 8/2007 | Awwiller |
| 2007/0235181 A1 | 10/2007 | Lecampion |
| 2007/0298979 A1 | 12/2007 | Perry et al. |
| 2008/0006410 A1 | 1/2008 | Looney et al. |
| 2008/0059140 A1 | 3/2008 | Salmon et al. |
| 2008/0070806 A1 | 3/2008 | Lin et al. |
| 2008/0081771 A1 | 4/2008 | Lin et al. |
| 2008/0093073 A1 | 4/2008 | Bustos et al. |
| 2008/0115930 A1 | 5/2008 | Peters et al. |
| 2008/0179060 A1 | 7/2008 | Surjaatmadja et al. |
| 2008/0234147 A1 | 9/2008 | Li et al. |
| 2008/0264640 A1 | 10/2008 | Eslinger |
| 2009/0032252 A1 | 2/2009 | Boney et al. |
| 2009/0044945 A1 | 2/2009 | Wilberg et al. |
| 2009/0071239 A1 | 3/2009 | Rojas et al. |
| 2009/0087912 A1 | 4/2009 | Ramos et al. |
| 2009/0143252 A1 | 6/2009 | Lehmann |
| 2009/0145607 A1 | 6/2009 | Li et al. |
| 2009/0193881 A1 | 8/2009 | Finnberg |
| 2009/0203557 A1 | 8/2009 | Barnes et al. |
| 2009/0242196 A1 | 10/2009 | Pao |
| 2009/0248309 A1 | 10/2009 | Nelville et al. |
| 2009/0253595 A1 | 10/2009 | Qu |
| 2009/0266548 A1 | 10/2009 | Olsen et al. |
| 2009/0283257 A1 | 11/2009 | Becker |
| 2009/0313772 A1 | 12/2009 | Talley |
| 2010/0010106 A1 | 1/2010 | Crews |
| 2010/0049625 A1 | 2/2010 | Biebesheimer et al. |
| 2010/0051511 A1 | 3/2010 | Faerman |
| 2010/0121623 A1 | 5/2010 | Yogeswaren |
| 2010/0128982 A1 | 5/2010 | Dvorkin et al. |
| 2010/0186520 A1 | 7/2010 | Wheeler |
| 2010/0213579 A1 | 8/2010 | Henry |
| 2010/0224365 A1 | 9/2010 | Abad |
| 2010/0243242 A1 | 9/2010 | Boney et al. |
| 2010/0258265 A1 | 10/2010 | Karanikas et al. |
| 2010/0263867 A1 | 10/2010 | Horton et al. |
| 2010/0276142 A1 | 11/2010 | Skildum et al. |
| 2010/0279136 A1 | 11/2010 | Bonucci |
| 2010/0323933 A1 | 12/2010 | Fuller et al. |
| 2011/0017458 A1 | 1/2011 | East et al. |
| 2011/0065612 A1 | 3/2011 | Stokes et al. |
| 2011/0067870 A1 | 3/2011 | East |
| 2011/0105369 A1 | 5/2011 | Reddy |
| 2011/0257944 A1 | 10/2011 | Du et al. |
| 2011/0259588 A1 | 10/2011 | Ali |
| 2011/0284214 A1 | 11/2011 | Ayoub et al. |
| 2012/0018159 A1 | 1/2012 | Gulta et al. |
| 2012/0026037 A1 | 2/2012 | Thomson et al. |
| 2012/0085534 A1 | 4/2012 | Morvan et al. |
| 2012/0129737 A1 | 5/2012 | Lesko et al. |
| 2012/0150515 A1 | 6/2012 | Hariharan et al. |
| 2012/0152547 A1 | 6/2012 | Hinkel |
| 2012/0160777 A1 | 6/2012 | Wahid |
| 2012/0179444 A1 | 7/2012 | Ganguly et al. |
| 2012/0193578 A1 | 8/2012 | Pan et al. |
| 2012/0247774 A1 | 10/2012 | Li et al. |
| 2012/0261129 A1 | 10/2012 | Becker |
| 2012/0261617 A1 | 10/2012 | Pan et al. |
| 2012/0267102 A1 | 10/2012 | Huang et al. |
| 2012/0305247 A1 | 12/2012 | Chen et al. |
| 2012/0318498 A1 | 12/2012 | Parsche |
| 2013/0013209 A1 | 1/2013 | Zhu et al. |
| 2013/0032349 A1 | 2/2013 | Alekseenko et al. |
| 2013/0056213 A1 | 3/2013 | Medvedev et al. |
| 2013/0084643 A1 | 4/2013 | Commarieu et al. |
| 2013/0090270 A1 | 4/2013 | Crews et al. |
| 2013/0137610 A1 | 5/2013 | Huang |
| 2013/0160994 A1 | 6/2013 | Alsop et al. |
| 2013/0161002 A1 | 6/2013 | Wigand |
| 2013/0161003 A1 | 6/2013 | Mikhailovich et al. |
| 2013/0199787 A1 | 8/2013 | Dale et al. |
| 2013/0213120 A1 | 8/2013 | Lebedev |
| 2013/0213638 A1 | 8/2013 | Keller |
| 2013/0228019 A1 | 9/2013 | Meadows |
| 2013/0231908 A1 | 9/2013 | Williams et al. |
| 2013/0233536 A1 | 9/2013 | Alqam |
| 2013/0238304 A1 | 9/2013 | Glinsky |
| 2013/0248192 A1 | 9/2013 | Cook |
| 2013/0264121 A1 | 10/2013 | Young |
| 2013/0269933 A1 | 10/2013 | Pomerantz et al. |
| 2013/0274149 A1 | 10/2013 | Lafitte et al. |
| 2013/0275099 A1 | 10/2013 | Frydman |
| 2013/0306321 A1 | 11/2013 | Lanctot-Downs et al. |
| 2013/0341028 A1 | 12/2013 | Christian et al. |
| 2014/0008305 A1 | 1/2014 | Nichols et al. |
| 2014/0027109 A1 | 1/2014 | Al-Baraik |
| 2014/0045732 A1 | 2/2014 | Mazyar |
| 2014/0048694 A1 | 2/2014 | Pomerantz |
| 2014/0069653 A1 | 3/2014 | Liu et al. |
| 2014/0078288 A1 | 3/2014 | Wu |
| 2014/0090850 A1 | 4/2014 | Benicewicz |
| 2014/0096964 A1 | 4/2014 | Chakraborty et al. |
| 2014/0116710 A1 | 5/2014 | Naser-El-Din et al. |
| 2014/0221257 A1 | 8/2014 | Roddy |
| 2014/0231077 A1 | 8/2014 | Rivero et al. |
| 2014/0243246 A1 | 8/2014 | Hendrickson |
| 2014/0247997 A1 | 9/2014 | Nishyama |
| 2014/0251605 A1 | 9/2014 | Hera |
| 2014/0260694 A1 | 9/2014 | Szlendak |
| 2014/0352968 A1 | 12/2014 | Pitcher |
| 2014/0364343 A1 | 12/2014 | Nelson et al. |
| 2014/0367100 A1 | 12/2014 | Oliveria et al. |
| 2014/0374104 A1 | 12/2014 | Kushal |
| 2015/0019183 A1 | 1/2015 | Suzuki |
| 2015/0041136 A1 | 2/2015 | Martin |
| 2015/0055438 A1 | 2/2015 | Yan et al. |
| 2015/0057097 A1 | 2/2015 | Cho |
| 2015/0057196 A1 | 2/2015 | Debord |
| 2015/0065398 A1 | 3/2015 | Gartland et al. |
| 2015/0071750 A1 | 3/2015 | Foster |
| 2015/0072902 A1 | 3/2015 | Lafitte et al. |
| 2015/0075782 A1 | 3/2015 | Sharma |
| 2015/0083405 A1 | 3/2015 | Dobroskok et al. |
| 2015/0096806 A1 | 4/2015 | Fonseca Ocampos |
| 2015/0136388 A1 | 5/2015 | Fehr et al. |
| 2015/0152724 A1 | 6/2015 | Amendt |
| 2015/0167440 A1 | 6/2015 | Kasevich |
| 2015/0176362 A1 | 6/2015 | Hariharan et al. |
| 2015/0192005 A1 | 7/2015 | Saeedfar |
| 2015/0259593 A1 | 9/2015 | Kaufman et al. |

(56) References Cited

U.S. PATENT DOCUMENTS

| | | | |
|---|---|---|---|
| 2015/0284625 A1 | 10/2015 | Silveira | |
| 2015/0293256 A1 | 10/2015 | Dusterhoft | |
| 2015/0300140 A1 | 10/2015 | Eoff et al. | |
| 2015/0322759 A1 | 11/2015 | Okoniewski | |
| 2015/0368541 A1 | 12/2015 | Monclin et al. | |
| 2016/0017202 A1 | 1/2016 | Yang et al. | |
| 2016/0060133 A1 | 3/2016 | Vollmer et al. | |
| 2016/0061017 A1 | 3/2016 | Nguyen et al. | |
| 2016/0103047 A1 | 4/2016 | Liu | |
| 2016/0103049 A1 | 4/2016 | Liu | |
| 2016/0130496 A1 | 5/2016 | Holtsclaw et al. | |
| 2016/0137904 A1 | 5/2016 | Drake | |
| 2016/0177674 A1 | 6/2016 | Shetty et al. | |
| 2016/0201440 A1 | 7/2016 | Aidagulov | |
| 2016/0203239 A1 | 7/2016 | Samuel et al. | |
| 2016/0208591 A1 | 7/2016 | Weaver et al. | |
| 2016/0215202 A1 | 7/2016 | Weaver et al. | |
| 2016/0215205 A1 | 7/2016 | Nguyen | |
| 2016/0256583 A1 | 9/2016 | Yamada | |
| 2016/0265331 A1 | 9/2016 | Weng et al. | |
| 2016/0289543 A1 | 10/2016 | Chang et al. | |
| 2016/0362965 A1 | 12/2016 | Parlar | |
| 2017/0015895 A1 | 1/2017 | Cox | |
| 2017/0030188 A1 | 2/2017 | Lehr | |
| 2017/0051598 A1 | 2/2017 | Ouenes | |
| 2017/0066959 A1 | 3/2017 | Hull | |
| 2017/0066962 A1 | 3/2017 | Ravi et al. | |
| 2017/0067836 A1 | 3/2017 | Hull et al. | |
| 2017/0137703 A1 | 5/2017 | Leverson et al. | |
| 2017/0145303 A1 | 5/2017 | Fontenelle et al. | |
| 2017/0145793 A1 | 5/2017 | Ouenes | |
| 2017/0176639 A1 | 6/2017 | Mosse et al. | |
| 2017/0198207 A1 | 7/2017 | Li et al. | |
| 2017/0247997 A1 | 8/2017 | Kovalevsky | |
| 2017/0248011 A1 | 8/2017 | Craddock et al. | |
| 2017/0275525 A1 | 9/2017 | Koep et al. | |
| 2017/0235181 A1 | 10/2017 | Lecampion et al. | |
| 2017/0328179 A1 | 11/2017 | Dykstra et al. | |
| 2017/0336528 A1 | 11/2017 | Badri et al. | |
| 2017/0370197 A1 | 12/2017 | Han et al. | |
| 2018/0051546 A1 | 2/2018 | Chen et al. | |
| 2018/0112126 A1 | 4/2018 | Yang et al. | |
| 2018/0119533 A1 | 5/2018 | Alhuthali | |
| 2018/0119535 A1 | 5/2018 | Shen et al. | |
| 2018/0155602 A1 | 6/2018 | Zhang | |
| 2018/0155615 A1 | 6/2018 | Rahy et al. | |
| 2018/0195982 A1 | 7/2018 | Hull et al. | |
| 2018/0266183 A1 | 9/2018 | Ayub | |
| 2018/0305208 A1 | 10/2018 | Mason | |
| 2018/0321416 A1 | 11/2018 | Freedman | |
| 2018/0355707 A1 | 12/2018 | Herrera et al. | |
| 2018/0371903 A1 | 12/2018 | Li et al. | |
| 2019/0010795 A1 | 1/2019 | Cascio et al. | |
| 2019/0017203 A1 | 1/2019 | Andoh et al. | |
| 2019/0078424 A1 | 3/2019 | Copeland et al. | |
| 2019/0112912 A1 | 4/2019 | Thompson et al. | |
| 2019/0195043 A1 | 6/2019 | Singh | |
| 2019/0211658 A1 | 7/2019 | Hull et al. | |
| 2019/0218907 A1 | 7/2019 | Ow | |
| 2019/0226956 A1 | 7/2019 | Alruwaili et al. | |
| 2019/0292436 A1 | 9/2019 | Mason et al. | |
| 2019/0345377 A1 | 11/2019 | Haque et al. | |
| 2020/0024935 A1 | 1/2020 | Eitschberger et al. | |
| 2020/0024936 A1 | 1/2020 | Chang | |
| 2020/0048531 A1 | 2/2020 | Hull et al. | |

FOREIGN PATENT DOCUMENTS

| | | | |
|---|---|---|---|
| CA | 2669788 C * | 3/2010 | ............ C09K 8/592 |
| CN | 101726223 | 6/2010 | |
| CN | 102015959 | 4/2011 | |
| CN | 102220116 | 10/2011 | |
| CN | 101819111 | 12/2011 | |
| CN | 1621803 | 5/2012 | |
| CN | 103387827 | 11/2013 | |
| CN | 102183410 | 5/2014 | |
| CN | 104727799 | 6/2015 | |
| CN | 105219948 | 1/2016 | |
| CN | 105445440 | 3/2016 | |
| CN | 105567213 | 5/2016 | |
| EA | 004186 | 2/2004 | |
| EP | 0247669 | 12/1987 | |
| EP | 0460927 | 12/1991 | |
| EP | 0474350 | 9/1994 | |
| EP | 2480625 | 4/2013 | |
| EP | 2480626 | 4/2013 | |
| GB | 2161269 | 8/1988 | |
| GB | 2332223 | 6/1999 | |
| RU | 2211318 | 8/2003 | |
| SU | 1036926 | 8/1983 | |
| SU | 1680925 | 9/1991 | |
| SU | 1709055 | 1/1992 | |
| WO | WO 1997028098 | 8/1997 | |
| WO | WO 0060379 | 10/2000 | |
| WO | WO 2000060379 | 10/2000 | |
| WO | WO 0194749 | 12/2001 | |
| WO | WO 2001094749 | 12/2001 | |
| WO | WO 2002064702 | 8/2002 | |
| WO | WO 2004005435 | 1/2004 | |
| WO | WO 2008001218 | 1/2008 | |
| WO | WO 2010008684 | 1/2010 | |
| WO | WO 2010074581 | 7/2010 | |
| WO | WO 2010083166 | 7/2010 | |
| WO | WO 2010138914 | 12/2010 | |
| WO | WO 2011035292 | 3/2011 | |
| WO | WO 2011035294 | 3/2011 | |
| WO | WO 2012051647 | 4/2012 | |
| WO | WO 2012057910 | 5/2012 | |
| WO | WO 2012087887 | 6/2012 | |
| WO | WO 2012087898 | 6/2012 | |
| WO | WO 2012088476 | 6/2012 | |
| WO | WO 2012104582 | 8/2012 | |
| WO | WO 2012122505 | 9/2012 | |
| WO | WO 2012171857 | 12/2012 | |
| WO | WO 2013052359 | 4/2013 | |
| WO | WO 2013112114 | 8/2013 | |
| WO | WO 2013149122 | 10/2013 | |
| WO | WO 2013154926 | 10/2013 | |
| WO | WO 2013155061 | 10/2013 | |
| WO | WO 2014008496 | 1/2014 | |
| WO | WO 2014008598 | 1/2014 | |
| WO | WO 2014116305 | 7/2014 | |
| WO | WO 2014123672 | 8/2014 | |
| WO | WO 2014178504 | 11/2014 | |
| WO | WO 2015041664 | 3/2015 | |
| WO | WO 2015041669 | 3/2015 | |
| WO | WO 2015071750 | 5/2015 | |
| WO | WO 2015097116 | 7/2015 | |
| WO | WO 2015126082 | 8/2015 | |
| WO | WO 2015163858 | 10/2015 | |
| WO | WO 2015181028 | 12/2015 | |
| WO | WO 2015200060 | 12/2015 | |
| WO | WO 2016089813 | 6/2016 | |
| WO | WO 2016094153 | 6/2016 | |
| WO | WO-2016127108 A1 * | 8/2016 | ........... E21B 43/164 |
| WO | WO 2017035371 | 3/2017 | |
| WO | WO 2017040824 | 3/2017 | |
| WO | WO 2017040834 | 3/2017 | |
| WO | WO 2017065331 | 4/2017 | |
| WO | WO 2017078674 | 5/2017 | |
| WO | WO 2017086975 | 5/2017 | |
| WO | WO 2017106513 | 6/2017 | |
| WO | WO 2017136641 | 8/2017 | |
| WO | WO 2017161157 | 9/2017 | |
| WO | WO 2018025010 | 2/2018 | |
| WO | WO 2018045290 | 3/2018 | |
| WO | WO 2018118024 | 6/2018 | |
| WO | WO 2018170035 | 9/2018 | |
| WO | WO 2018170065 | 9/2018 | |
| WO | WO 2018174987 | 9/2018 | |
| WO | WO 2018175394 | 9/2018 | |

(56) References Cited

FOREIGN PATENT DOCUMENTS

| WO | WO 2019064041 | 4/2019 |
|---|---|---|
| WO | WO 2019140058 | 7/2019 |

OTHER PUBLICATIONS

Li et al., "A methodology for estimating the organic porosity of the source rocks at the mature stage: example from the marlstone in the Shulu Sag, Bohai Bay Basin," Arabian Journal of Geosciences, Springer International Publishing, Cham, 9(6): 1-11, May 2016, 11 pages.
Lu et al., "Investigation of oxidation and heat treatment to improve mass transport ability in coals," Fuel, IPC Science and Technology Press, Guildford, GB, 283: 118840, Aug. 2020, 17 pages.
U.S. Appl. No. 15/243,312, filed Aug. 22, 2016, Chen.
"Hydraulic Fracturing Fluid Product Component Information Disclosure," 2012, 2 pages.
Abad et al., "Evaluation of the Material Properties of the Multilayered Oxides formed on HCM12A using New and Novel Techniques," Manuscript No. OX1D-D-15-00019, Manuscript Draft, 2015, 44 pages.
Abass et al., "Wellbore Instability of Shale Formation, Zuluf Field, Saudi Arabia," Society of Petroleum Engineers (SPE), presented at the SPE Technical Symposium on Saudi Arabia Section, Dhahran, Saudi Arabia, May 21-23, 2006, 10 pages.
Abousleiman and Nguyen, "Poromechanics Response of Inclined Wellbore Geometry in Fractured Porous Media," Journal of Engineering Mechanics, ASCE, Nov. 2005, 131:11, 14 pages.
Abousleiman et al, "Anisotropic Porothermoelastic Solution and Hydro-Thermal Effects on Fracture Width in Hydraulic Fracturing," Int. J. Numer. Anal. Meth. Geomech., 2013, 25 pages.
Abousleiman et al, "Poroviscoelastic Analysis of Borehole and Cylinder Problems," ACTA Mechanica, 1996, 119: 199-219, 21 pages.
Abousleiman et al, "The Granular and Polymer Nature of Kerogen Rich Shale," Acta Geotechnica 2016, 11 (3): 573-594, 22 pages.
Abousleiman et al., "A Micromechanically Consistent Poroviscoelasticity Theory for Rock Mechanics Applications," International Journal of Rock Mechanics and Mining Services & Geomechanics, Abstracts, 1993, 30:7 (1177-1180), 4 pages.
Abousleiman et al., "GeoGenome Industry Consortium (G2IC)," JIP, 2004-2006, 6 pages.
Abousleiman et al., "Geomechanics Field and Laboratory Characterization of Woodford Shale: The Next Gas Play," SPE 110120, Society of Petroleum Engineers (SPE), presented at the 2007 SPE Annual Technical Conference and Exhibition on Nov. 11-14, 2007, 14 pages.
Abousleiman et al., "Geomechanics Field Characterization of the Two Prolific U.S. Mid-West Gas Plays with Advanced Wire-Line Logging Tools," SPE 124428, Society of Petroleum Engineers (SPE), presented at 2009 SPE Annual Technical Conference and Exhibition, Oct. 4-7, 2009, 19 pages.
Abousleiman et al., "Geomechanics Field Characterization of Woodford Shale and Barnett Shale with Advanced Logging Tools and Nano-indentation on Drill Cuttings," The Leading Edge, Special Section: Borehole Geophysics, Jun. 2010, 6 pages.
Abousleiman et al., "Mandel's Problem Revisited," Geotechnique, 1996, 46:2 (187-195), 9 pages.
Abousleiman et al., "Mechanical Characterization of Small Shale Samples subjected to Fluid Exposure using the Inclined Direct Shear Testing Device," International Journal of Rock Mechanics and Mining Sciences, 2010, 47:3 (355-367), 13 pages.
Abousleiman et al., "Modeling Real-Time Wellbore Stability within the Theory of Poromechanics," AADE-03-NTCE-11, presented at the AADE 2003 National Technology Conference, Practical Solutions for Drilling Challenges, Texas, Apr. 1-3, 2003, 14 pages.
Abousleiman et al., "Poroelastic Solutions in Transversely Isotropic Media for Wellbore and Cylinder," PPI: S0020-7683(98)00101-2, International Journal of Solids Structures, 1998, 35:34-35 (4905-4929), 25 pages.

Abousleiman et al., "Time-Dependent wellbore (instability predictions: theory and case study," IADC/SPE 62796, International Association of Drilling Contractors (IADC), Society of Petroleum Engineers (SPE), presented at the 2000 IADC/SPE Asia Pacific Drilling Technology held in Kuala Lumur, Malaysia, Sep. 11-13, 2000, 8 pages.
Agenet et al., "Fluorescent Nanobeads: a First Step Toward Intelligent Water Tracers," SPE 157019, Society of Petroleum Engineers (SPE), SPE International Oilfield Nanotechnology Conference, Jun. 12-14, 2012, 13 pages.
Agilent Technologies, "Field-Deployable Solution for Nanoporosity Measurements in Mud Logging Operations and a Novel Method for Fracability Analysis Using Mud Cuttings," Gulf Coast Conference, Agilent Restricted, Oct. 2013, 44 pages.
Ahmed et al. "7.2.2 Information Required to Move to a Pilot Project," Unconventional Resources Exploitation and Development, 2016, 1 page.
Aidagulov et al., "Model of Hydraulic Fracture Initiation from the Notched Open hole," SPE-178027-MS, Society of Petroleum Engineers (SPE), presented at the SPE Saudi Arabia Section Annual Technical Symposium and Exhibition, Apr. 21-23, 2015, 13 pages.
Aidagulov et al., "Notching as a New Promising Well Intervention Technique to Control Hydraulic Fracturing in Horizontal Open Holes," AAPG Datapages/Search and Discovery Article #90254, American Association of Petroleum Geologists (AAPG), presented at the 12th Middle East Geosciences Conference and Exhibition GEO-2016, Mar. 7-10, 2016.
AlDuailej et al., "CO 2 Emulsified Fracturing Fluid for Unconventional Applications," SPE-177405, Society of Petroleum Engineers, Abu Dhabi International Petroleum Exhibition and Conference held in Abu Dhabi, UAE, Nov. 9-12, 2015, 12 pages.
Al-Ghamdi et al., "Impact of Acid Additives on the Rheological Properties of Viscoelastic Surfactants and Their Influence on Field Application" SPE-89418-MS, Society of Petroleum Engineers, Presented at the SPE/DOE Symposium on Improved Oil Recovery, Tulsa, Apr. 17-21, 2004, 13 pages.
Allan et al., "A Multiscale Methodology for the Analysis of Velocity Anisotropy in Organic-Rich Shale," Geophysics, Jul.-Aug. 2015, 80:4 (C73-C88), 16 pages.
Alleman et al., "The Development and Successful Field Use of Viscoelastic Surfactant-based Diverting Agents for Acid Stimulation" SPE-80222-MS, Society of Petroleum Engineers, Presented at the International Symposium on Oilfield Chemistry, Houston, Feb. 5-7, 2004, 10 pages.
Al-Muntasheri, "A Critical Review of Hydraulic-Fracturing Fluids for Moderate- to Ultralow-Permeability Formations Over the Last Decade," SPE-169552-PA, Society of Petroleum Engineers, SPE Prod & Oper 29, Nov. 2014, (4):243-260, 18 pages.
Al-Munthasheri, "A Critical Review of Hydraulic Fracturing Fluids over the Last Decade," SPE 169552, Society of Petroleum Engineers (SPE), presented at the SPE Western North American and Rocky Mountain Joint Regional Meeting, Apr. 16-18, 2014, 25 pages.
Al-Qahtani et al., "A Semi-Analytical Model for Extended-Reach Wells with Wellbore Flow Splitting; a Production Optimization Scheme," SPE-177931, Society of Petroleum Engineers (SPE), presented at the Abu Dhabi International Petroleum Exhibition and Conference, Nov. 9-12, 2015, 21 pages.
Altowairqi, "Shale elastic property relationships as a function of total organic carbon content using synthetic samples," Journal of Petroleum Science and Engineering, Sep. 2015, 133: 392-400, 9 pages.
Al-Yami et al., "Engineered Fit-for-Purpose Cement System to Withstand Life-of-the-Well Pressure and Temperature Cycling," SPE-188488-MS, Society of Petroleum Engineers (SPE), presented at the Abu Dhabi International Petroleum Exhibition & Conference, Nov. 2017, 14 pages.
Ananthan et al., "Influence of Strain Softening on the Fracture of Plain Concrete Beams," International Journal of Fracture, 1990, 45: 195-219, 25 pages.

(56) References Cited

OTHER PUBLICATIONS

Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.
Apageo.com [online], "Menard Pressuremeter Pressuremeter test according," 2016, retrieved on Oct. 7, 2019, retrieved from URL <https://www.apageo.com/en/3/products%2Cpressuremeter-tests%2Cmenard-pressuremeter%2C14%2C5,html>, 2 pages.
Arias et al., "New Viscoelastic Surfactant Fracturing Fluids Now Compatible with CO2 Drastically Improve Gas Production in Rockies," SPE-111431-MS, Presented at the SPE International Symposium and Exhibition on Formation Damage Control, Lafayette, Louisiana, Feb. 13-15, 2008, 5 pages.
Arns et al., "Computation of linear elastic properties from microtomographic images: Methodology and agreement between theory and experiment," Geophysics, Sep.-Oct. 2002, 67:5 (1396-1405), 10 pages.
Aslan et al., "Fluorescent Core—Shell AG@SiO$_2$ Nanocomposites for Metal-Enhanced Fluorescence and Single Nanoparticle Sensing Platforms," American Chemical Society (ACS), J. Am. Chem. Soc., JACS Communications, Jan. 19, 2007, 129: 1524-1525, 2 pages.
Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170: 390-397, 8 pages.
Azizi et al, "Design of Deep Foundations Using the Pressuremeter Method," Proceedings of the Sixth International Offshore and Polar Engineering Conference, Los Angeles, May 1996, The International Offshore and Polar Engineers, 1, 9 pages.
Ballice, "Solvent Swelling Studies of Goynuk (Kerogen Type-I) and Beypazari Oil Shales (Kerogen Type-II)," Science Direct, Fuel, 2003, 82: 1317-1321, 5 pages.
Bandyopadhyay et al., "Effect of Silica Colloids on the Rheology of Viscoelastic Gels Formed by the Surfactant Cetyl Trimethylammonium Tosylate," J. Colloid Interf. Sci., 2005, 283(2):585-591, 7 pages.
Barati and Liang, "A Review of Fracturing Fluid Systems Used for Hydraulic Fracturing of Oil and Gas Wells," Journal of Applied Polymer Science, Aug. 15, 2014, 131:16, 11 pages.
Barenblatt et al., "Basic Concepts in the Theory of Seepage of Homogeneous Liquids in Fissured Rocks (Strata)," PMM 1960, 24:5 (852-864), 18 pages.
Bazant et al., "Deformation of Progressively Cracking Reinforced Concrete Beams," Title No. 81-26, ACI Journal, Technical Paper, May-Jun. 1984, 81:3, 11 pages.
Bazant et al., "Size Effect in Brazilian Split-Cylinder Tests: Measurements and Fracture Analysis," ACI Materials Journal, Technical Paper, Title No. 88-M40, May 31, 1991, 88:3 (325-332), 8 pages.
Bazant et al., "Strain-Softening Bar and Beam: Exact Non-Local Solution," International Journal of Solids Structures, 1988, 24:7 (659-673), 15 pages.
Benafan et al., "Shape Memory Alloy Rock Splitters (SMARS)—A Non-Explosive Method for Fracturing Planetary Rocklike Materials and Minerals," NASA/TM—2015-218832, NASA STI Program, Jul. 2015, 42 pages.
Bennett et al., "Instrumented Nanoindentation and 3D Mechanistic Modeling of a Shale at Multiple Scales," Acta Geotechnica, Jan. 2015, 10:21, 14 pages.
Berger et al., "Effect of eccentricity, voids, cement channels, and pore pressure decline on collapse resistance of casing," SPE-90045-MS, Society of Petroleum Engineers (SPE), presented at the SPE Annual Technical Conference and Exhibition, Sep. 26-29, 2004, 8 pages.
Bernheim-Groswasser et al., "Micellar Growth, Network Formation, and Criticality in Aqueous Solutions of the Nonionic Surfactant C12E5," Langmuir, Apr. 2000, 16(9):4131-4140, 10 pages.
Berryman, "Extension of Poroelastic Analysis to Double-Porosity Materials: New Technique in Microgeomechanics," Journal of Engineering Mechanics, 128:8 (840), Aug. 2002, 8 pages.

Bhandari et al., "Two-Dimensional DEM Analysis of Behavior of Geogrid-Reinforced Uniform Granular Bases under a Vertical Cyclic Load," Acta Geotechnica 10:469-480, 2014, 12 pages.
Biot et al., "Temperature analysis in hydraulic fracturing," Journal of Petroleum Technology, 39:11, Nov. 1987, 9 pages.
Biot, "General Theory of Three-Dimensional Consolidation," The Ernest Kempton Adams Fund for Physical Research of Columbia University, Reprint Series, Journal of Applied Physics, Feb. 1941, 12:2, 11 pages.
Bisnovat et al., "Mechanical and petrophysical behavior of organic-rich chalk from the Judea Plains, Israel," Marine and Petroleum Geology, 64: 152-164, Jun. 2015, 13 pages.
Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.
Bobko et al., "The Nanogranular Origin of Friction and Cohesion in Shale—A Strength Homogenization Approach to Interpretation of Nanoindentation Results," International Journal for Numerical Analytical Method in Geomechanics, 2010, 23 pages.
Boskey et al., "Perspective—Collagen and Bone Strength," Journal of Bone and Mineral Research, 1999, 14:3, 6 pages.
Bourbie and Zinszner, "Hydraulic and Acoustic Properties as a Function of Porosity in Fontainebleau Sandstone," Journal of Geophysical Research, 90:B13 (11524-11532), Nov. 1985, 9 pages.
Bratton et al., "The Nature of Naturally Fractured Reservoirs," Oilfield Review, Jun. 2006, 21 pages.
Brochard et al., "Fracture Properties of Kerogen and Importance for Organic-Rich Shales," Annual World Conference on Carbon (Carbon 2013), Jul. 2013, 5 pages.
Brown et al., "Use of a Viscoelastic Carrier Fluid in Frack-Pack Applications," SPE-31114-MS, Society of Petroleum Engineers, Presented at the SPE Formation Damage Control Symposium, Lafayette, Louisiana, Feb. 14-15, 1996, 10 pages.
Bunzil et al., "Taking Advantage of Luminescent Lanthanide Ions," Chemical Society Reviews (CSR), Critical Review, 34: 1048-1077, Dec. 2005, 30 pages.
Bustos et al., "Case Study: Application of a Viscoelastic Surfactant-Based CO2 Compatible Fracturing Fluid in the Frontier Formation, Big Horn Basin, Wyoming," SPE-107966-MS, Society of Petroleum Engineers, Presented at the Rocky Mountain Oil & Gas Technology Symposium, Denver, Apr. 16-18, 2007, 11 pages.
Caenn et al., "Chapter 9: Wellbore Stability," p. 359, in Composition and Properties of Drilling and Completion Fluids, 7th Edition: Gulf Professional Publishing, 2016, 1 page.
Cahill et al., "Nanoscale Thermal Transport II," Applied Physics Reviews 1.1:011305, 2014, 46 pages.
Cahill et al., "Nanoscale Thermal Transport," Journal of Applied Physics 93:2, Jan. 15, 2003, 28 pages.
Cai et al., "Experimental Investigation on Perforation of Shale with Ultra-High Pressure Abrasive Water Jet: Spake, Mechanism and Sensitivity," Journal of Natural Gas Science and Engineering, Jul. 2019, 67: 196-213, 18 pages.
California Council on Science and Technology Lawrence Berkeley National Laboratory Pacific Institute, "Advanced Well Stimulation Technologies in California: An Independent Review of Scientific and Technical Information," CCST, Jul. 2016, 400 pages.
Carcione and Avseth, "Rock-physics templates for clay-rich source rocks," Geophysics 80:5 (D481-D500), Sep. 2015, 21 pages.
Carcione et al., "Theory of borehole stability when drilling through salt formations," Geophysics, May-Jun. 2006, 71:3, 17 pages.
Carter and Hanson, "Fake Moon Dirt, HOOD Solar System Science," UT Dallas Magazine, 6:2, Spring 2016, 1 page.
Cates, "Nonlinear Viscoelasticity of Wormlike Micelles (and Other Reversibly Breakable Polymers)," J. Phys. Chem., 1990, 94(1):371-375, 5 pages.
Cates, "Statics and Dynamics of Worm-Like Surfactant Micelles," J. Phys-Condens., 1990, Mat. 2(33):6869-6892, 25 pages.
Chang et al, "Multiple Fracture Initiation in Openhole without Mechanical Isolation: First Step to Fulfill an Ambition," SPE 168638, Society of Petroleum Engineers (SPE), presented at the SPE Hydraulic Fracturing Technology Conference, Feb. 4-6, 2014, 18 pages.

(56) References Cited

OTHER PUBLICATIONS

Chang et al., "A Novel Self-Diverting-Acid Developed for Matrix Stimulation of Carbonate Reservoirs," SPE-65033-MS, Society of Petroleum Engineers, Presented at the SPE International Symposium on Oilfield Chemistry, Houston, Feb. 13-16, 2001, 6 pages.

Chang et al., "Experience in Acid Diversion in High Permeability Deep Water Formations Using Visco-Elastic-Surfactant," SPE-68919-MS, Society of Petroleum Engineers, Presented at the SPE European Formation Damage Conference, The Hague, The Netherlands, 21-22 May 21-22, 2001, 5 pages.

Chang et al., "Magnetic SERS Composite Nanoparticles for Microfluidic Detection," abstract to 251st ACE National Meeting, Mar. 13-17, 2016, 1 page (abstract).

Chang, "In-Situ Formation of Proppant and Highly Permeable Blocks for Hydraulic Fracturing," SPE-173328-MS, Society of Petroleum Engineers (SPE), SPE Hydraulic Fracturing Technology Conference Feb. 3-5, 2015, 11 pages.

Chen et al., "Novel CO2-Emulsified Viscoelastic Surfactant Fracturing Fluid System," SPE-94603-MS, Society of Petroleum Engineers, Presented at the SPE European Formation Damage Conference, Scheveningen, The Netherlands, May 25-27, 2005, 6 pages.

Chen et al., "Size Effect in Micro-Scale Cantilever Beam Bending," Acta Mech., 2011, 219: 291-307, 17 pages.

Chen et al., "FITC functionalized magnetic core-shell $Fe_3O_4/Ag$ hybrid nanoparticle for selective determination of molecular biothiols," Sensorsand Actuators B: Chemical, 193: 857-863, Dec. 2013, 7 pages.

Chern et al., "Deformation of Progressively Cracking Partially Prestressed Concrete Beams," PCI Journal, Jan.-Feb. 1992, 37:1, 11 pages.

Cheshomi et al., "Determination of uniaxial compressive strength of microcystalline limestone using single particles load test," Journal of Petroleum Science and Engineering, 111: 121-126, 2013, 6 pages.

Chevalier et al., "Micellar Properties of Zwitterionic Phosphobetaine Amphiphiles in Aqueous Solution: Influence of the Intercharge Distance," Colloid Polym. Sci., 1988, 266(5):441-448, 8 pages.

Chevalier et al., "Structure of Zwitterionic Surfactant Micelles: Micellar Size and Intermicellar Interactions," J. Phys. Chem., Jun. 1992, 96(21):8614-8619, 6 pages.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.

Chupin et al., "Finite Strain Analysis of Nonuniform Deformation Inside Shear Bands in Sands," International Journal for Numerical and Analytical Methods in Geomechanics, 2012, 36: 1651-1666, 16 pages.

Clough et al., "Characterization of Kerogen and Source Rock Maturation Using Solid-State NMR Spectroscopy," Energy & Fuels, 2015, 29(10): 6370-6382, 42 pages.

Corapcioglu, "Fracturing Fluid Effects on Young's Modulus and Embedment in the Niobrara Formation," Thesis for degree of Master of Science (Petroleum Engineering), Colorado School of Mines, 2014, 189 pages.

Couillet et al., "Synergistic Effects in Aqueous Solutions of Mixed Wormlike Micelles and Hydrophobically Modified Polymers," Macromolecules, American Chemical Society, 2005, 38(12):5271-5282, 12 pages.

Crews et al., "Internal Breakers for Viscoelastic Surfactant Fracturing Fluids," SPE-106216-MS, Society of Petroleum Engineers, Presented at the International Symposium on Oilfield Chemistry, Houston, Feb. 28-Mar. 2, 2007, 8 pages.

Crews et al., "New Remediation Technology Enables Removal of Residual Polymer in Hydraulic Fractures," SPE-135199-MS, Society of Petroleum Engineers, Presented at the SPE Annual Technical Conference and Exhibition, Florence, Italy, Sep. 19-22, 2010.

Crews et al., "New Technology Improves Performance of Viscoelastic Surfactant Fluids" SPE-103118-PA, Society of Petroleum Engineers, SPE Drill & Compl, SPE Annual Technical Conference and Exhibition, San Antonio, Texas, Sep. 24-27, 2008, 23(1):41-47, 7 pages.

Crews et al., "Performance Enhancements of Viscoelastic Surfactant Stimulation Fluids with Nanoparticles," SPE-113533-MS, Society of Petroleum Engineers, Presented at the Europec/EAGE Annual Conference and Exhibition, Rome, Jun. 9-12, 2008, 10 pages.

Crews et al., "The Future of Fracturing-Fluid Technology and Rates of Hydrocarbon Recovery," SPE-115475-MS, Society of Petroleum Engineers, Presented at the SPE Annual Technical Conference and Exhibition, Denver, Sep. 21-24, 2008, 13 pages.

Crews, "Internal Phase Breaker Technology for Viscoelastic Surfactant Gelled Fluids," SPE-93449-MS, Society of Petroleum Engineers, Presented at the SPE International Symposium on Oilfield Chemistry, Houston, 2-4 Feb. 2-4, 2005, 11 pages.

Cubillos et al., "The Value of Inter-well and Single Well Tracer Technology for De-Risking and Optimizing a CEOR Process—Caracara Field Case," SPE 174394-MS, Society of Petroleum Engineers (SPE), presented at EUROPEC 2015, Jun. 1-4, 2015, 19 pages.

Cui et al., "Poroelastic solution for an inclined borehole," Transactions of the ASME, Journal of Applied Mechanics, 64, Mar. 1997, 7 pages.

Custelcean et al., "Aqueous Sulfate Separation by Crystallization of Sulfate-Water Clusters," Angewandte Chemie, International Edition, 2015, 54: 10525-10529, 5 pages.

Dagan, "Models of Groundwater Flow in Statistically Homogeneous Porous Formations," Water Resource Search 15:1, Feb. 1979, 17 pages.

Daneshy, "Hydraulic Fracturing to Improve Production," Tech 101, TheWayAhead, 6:3, Oct. 2010, 4 pages.

Daniel et al., "New Visco-Elastic Surfactant Formulations Extend Simultaneous Gravel-Packing and Cake-Cleanup Technique to Higher-Pressure and Higher-Temperature Horizontal Open-Hole Completions: Laboratory Development and a Field Case History From the North Sea," SPE-73770-MS, Society of Petroleum Engineers, Presented at the SPE International Symposium and Exhibition on Formation Damage, Lafayette, Louisiana, Feb. 20-21, 2002, 10 pages.

Das et al., "Molecular Fluorescence, Phosphorescence, and Chemiluminescence Spectrometry," American Chemical Society Publications (ACS), Analytical Chemistry, 84: 597-625, Nov. 3, 2011, 29 pages.

De Block et al., "A New Solution for the Characterization of Unconventional Shale Resources Based on Analysis or Drill Cutting," SPE-177601-MS, Society of Petroleum Engineers (SPE), presented at the Abu Dhabi International Petroleum Exhibition and Conference, Nov. 9-12, 2015, 6 pages.

De Rocha et al., "Concentrated CO2-in-Water Emulsions with Nonionic Polymeric Surfactants," Journal of Colloid and Interface Science, 2001, 239:1 (241-253), 13 pages.

Deans, "Using Chemical Tracers To Measure Fractional Flow And Saturation In-Situ," SPE 7076, Society of Petroleum Engineers (SPE) of AIME, presented at Fifth Symposium on Improved Methods for Oil Recovery of the Society of Petroleum Engineers of AIME, Apr. 16-19, 1978, 10 pages.

Deirieh et al., "Nanochemomechanical Assessment of Shale: A Coupled WDS-Indentation Analysis," Acta Geotechnica, 2012, 25 pages.

Delafargue and Ulm, "Explicit approximations of the indentation modulus of elastically orthotropic solids for conical indenters," International Journal of Solids and Structures 41:26 (7351-7360), Dec. 2004, 10 pages.

Detournay and Cheng, "Poroelastic Response of a Borehole in a Non-Hydrostatic Stress Field," International Journal of Rock Mechanics, Min. Science and Geomech. Abstracts, 25:3, 1988, 12 pages.

Devarapalli et al., "Micro-CT and FIB-SEM imaging and pour structure characterization of dolomite rock at multiple scales," Arabian Journal of Geosciences, Aug. 2017, 9 pages, abstract only.

Di Lullo et al., "Toward Zero Damage: New Fluid Points the Way," SPE-69453-MS, Society of Petroleum Engineers, Presented at the SPE Latin American and Caribbean Petroleum Engineering Conference, Buenos Aires, Argentina, Mar. 25-28, 2001, 8 pages.

(56) References Cited

OTHER PUBLICATIONS

Dreiss, "Wormlike Micelles: Where Do We Stand? Recent Developments, Linear Rheology, and Scattering Techniques," The Royal Society of Chemistry, Soft Matter, 2007, 3(8):956-970, 15 pages.

Dropek et al., "Pressure-temperature creep testing as applied to a commercial rock salt," Union Carbide, Office of Waste Isolation, prepared for the U.S. Energy Research and Development Administration, Jun. 1976, 54 pages.

Du et al., "Interwell Tracer Tests: Lessons Learned from past Field Studies," SPE 93140, Society of Petroleum Engineers (SPE), presented at SPE Asia Pacific Oil and Gas Conference and Exhibition, Apr. 5-7, 2005, 9 pages.

Ducros, "Source Rocks of the Middle East," Source Rock Kinetics: Goal and Perspectives. AAPG Geosciences Technology Workshop, Jul. 2016, 30 pages.

Dvorkin, "Kozeny-Carman Equation Revisited," 2009, 16 pages.

Eastoe et al, "Water-in-CO2 Microemulsions Studied by Small-Angle Neutron Scattering," Langmuir 1997, 13:26 (6980-6984), 5 pages.

Economides et al., Reservoir Stimulation, 2nd ed., Prentice Hall, Englewood Cliffs, New Jersey, 1989, 408 pages.

Ehlig-Economides and Economides, "Water as Poppant," SPE-147603, Society of Petroleum Engineers (SPE), presented at the SPE Annual Technical Conference and Exhibition, Oct. 30-Nov. 2, 2011, 8 pages.

Ekbote et al., "Porochemoelastic Solution for an Inclined Borehole in a Transversely Isotropic Formation," Journal of Engineering Mechanics, ASCE, Jul. 2006, 10 pages.

El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.

Elijah, "Numerical Modeling of Wellbore Instability (Tensile Failure) Using Fracture Mechanics Approach," Thesis for the degree of Master of Science, African University of Science and Technology Abuja, May 2013, 77 pages.

Eliyahu et al, "Mechanical Properties of organic matter in shales mapped at the nanometer scale," Marine and Petroleum Geology, 59:294-304, Sep. 18, 2014, 11 pages.

Ertas et al., "Petroleum Expulsion Part 1. Theory of Kerogen Swelling in Multicomponent Solvents," Energy & Fuels, 2006, 20: 295-300, 6 pages.

Eseme et al., "Review of mechanical properties of oil shales: implications for exploitation and basin modeling," Oil Shale 24:2 (159-174), Jan. 2007, 16 pages.

Esfahani et al., "Quantitative nanoscale mapping of three-phase thermal conductivities in filled skutterudites via scanning thermal microscopy," Nature Science Review 5:1, Feb. 2017, 31 pages.

Ewy, "Shale Swelling/Shrinkage and Water Content Change due to Imposed Suction and Due to Direct Brine Contact," Acta Geotechnica, 2014, 9: 869-886, 18 pages.

Ewy, "Wellbore-Stability Predictions by Use of a Modified Lade Criterion," SPE Drill and Completion, 14:2, Jun. 1999, 7 pages.

Fakoya et al., "Rheological Properties of Surfactant-Based and Polymeric Nano-Fluids," SPE-163921-MS, Society of Petroleum Engineers, Presented at the SPE/ICoTA Coiled Tubing and Well Intervention Conference and Exhibition, The Woodlands, Texas, Mar. 26-27, 2013, 17 pages.

fekete.com [online], "Dual Porosity," retrieved from URL <www.fekete.com/SAN/WebHelp/FeketeHarmony/Harmony_WebHelp/Content/HTML_Files/Reference_Material/General_Concepts/Dual_Porosity.htm>, available on or before 2014, retrieved on Nov. 11, 2019, 6 pages.

Finney, "Random packings and the structure of simple liquids I. The geometry of random close packing," Proceedings of the Royal Society A, May 1970, 319: 479-493, 15 pages.

Fjaer et al., "Stresses around Boreholes. Borehole Failure Criteria," in Petroleum Related Rock Mechanics, 2nd Edition, 2008, 156, 1 page.

Fontana et al., "Successful Application of a High Temperature Viscoelastic Surfactant (VES) Fracturing Fluids Under Extreme Conditions in Patagonian Wells, San Jorge Basin," SPE-107277-MS, Society of Petroleum Engineers, Presented at the EUROPEC/EAGE Annual Conference and Exhibition, London, Jun. 11-14, 2007, 15 pages.

Frazer et al., "Localized Mechanical Property Assessment of SiC/SiC Composite Materials," Science Direct, Composites: Part A, 2015, 70: 93-101, 9 pages.

Fredd et al., "Polymer-Free Fracturing Fluid Exhibits Improved Cleanup for Unconventional Natural Gas Well Applications" SPE-91433-MS, Society of Petroleum Engineers, Presented at the SPE Eastern Regional Meeting, Charleston, West Virginia, Sep. 15-17, 2004, 15 pages.

Gallegos and Varela, "Trends in Hydraulic Fracturing Distributions and Treatment Fluids, Additives, Proppants, Water Volumes Applied to Wells Drilled in the United States from 1947 through 2010—Data Analysis and Comparison to the Literature," USGS, United States Geological Survey, 2015, 24 pages.

Gandossi and Estorff, "An overview of hydraulic fracturing and other formation stimulation technologies for shale gas production," JRC Science for Policy Report, European Commission, EUR 26347 EN, Jan. 2013, 62 pages.

Ganjdanesh et al. "Treatment of Condensate and Water Blocks in Hydraulic-Fractured Shale-Gas/Condensate Reservoirs," SPE-175145, Society of Petroleum Engineers (SPE), presented at the SPE Annual Technical Conference and Exhibition, Sep. 28-30, 2015, SPE Journal, Apr. 2016, 10 pages.

Gao et al., "Materials Become Insensitive to Flaws at Nanoscale: Lessons from Nature," Proceedings of the National Academy of Sciences, PNAS, May 2003, 100:10 (5597-55600), 4 pages.

Gardiner et al., "Chapter 1: Introduction to Raman Scattering," in Practical Raman Spectroscopy, Springer-Verlag, 1989, 9 pages.

Garnero, "The Contribution of Collagen Crosslinks to Bone Strength," International Bone & Mineral Society, BoneKEy Reports, Sep. 2012, 1: 182, 8 pages.

George et al., "Approximate relationship between frequency-dependent skin depth resolved from geoelectronnagnetic pedotransfer function and depth of investigation resolved from geoelectrical measurements: A case study of coastal formation, southern Nigeria," Journal of Earth Syst. Sci, 125:7 (1379-1390), Oct. 2016, 12 pages.

Georgi et al., "Physics and Chemistry in Nanoscale Rocks," Society of Petroleum Engineers (SPE), SPE Forum Series, Frontier of Technology, Mar. 22-26, 2015, La Jolla, California, USA, 4 pages.

Glossary.oilfield.slb.com [online], "Oilfield Glossary: fluid-friction reducer," available on or before Jun. 15, 2017, retrieved from URL< http://www.glossary.oilfield.slb.com/Terms/f/fluid-friction_reducer.aspx>, 1 page.

Glover et al., "The Use of Measurements Made on Drill Cuttings to Construct and Apply Geomechanical Well Profiles," ARMA 16-0737, American Rock Mechanics Association (ARMA), presentation at the 50th US Rock Mechanics/Geomechanics Symposium, Jun. 26-29, 2016, 11 pages.

Godwin et al., "Simultaneous Gravel Packing and Filter-Cake Cleanup with Shunt Tubes in Openhole Completions: A Case History From the Gulf of Mexico," SPE-78806, Society of Petroleum Engineers, SPE Drill & Compl, Sep. 2002, 17(3):174-178, 5 pages.

Golomb et al, "Macroemulsion of liquid and supercritical CO2-in-water and water-in-liquid CO2 stabilized with fine particles," American Chemical Society (ACS), Ind. Eng. Chem. Res. 2006, 45:8 (2728-2733), 6 pages.

Gomaa et al., "New Insights Into the Viscosity of Polymer-Based In-Situ-Gelled Acids," SPE-121728-PA, Society of Petroleum Engineers, SPE Prod & Oper, Aug. 2010, 25(3):367-375, 9 pages.

Gomaa et al., "Viscoelastic Behavior and Proppant Transport Properties of a New Associative Polymer-Based Fracturing Fluid," SPE-168113-MS, Society of Petroleum Engineers, Presented at the SPE International Symposium and Exhibition on Formation Damage Control, Lafayette, Louisiana, Feb. 26-28, 2014, 17 pages.

Gomaa et al., "Viscoelastic Behavior and Proppant Transport Properties of a New High-Temperature Viscoelastic Surfactant-Based Fracturing Fluid," SPE-173745-MS, Society of Petroleum Engi-

(56) References Cited

OTHER PUBLICATIONS neers, Presented at the SPE International Symposium on Oilfield Chemistry, The Woodlands, Texas, Apr. 13-15, 2015, 25 pages.

Gomaa et al., "Viscoelastic Evaluation of a Surfactant Gel for Hydraulic Fracturing," SPE-143450-MS, Society of Petroleum Engineers, Presented at the SPE European Formation Damage Conference, Noordwijk, The Netherlands, Jun. 7-10, 2011, 18 pages.

Goodman, "Chapter 3: Rock Strength and Failure Criteria," in Introduction to Rock Mechanics, John Wiley & Sons, 21 pages.

Gravsholt, "Viscoelasticity in Highly Dilute Aqueous Solutions of Pure Cationic Detergents," Journal of Colloid and Interface Science, Dec. 1976, 57(3):575-577, 3 pages.

Gu and Mohanty, "Effect of Foam Quality on Effectiveness of Hydraulic Fracturing in Shales," International Journal of Rock Mechanics and Mining Sciences, 70: 273-285, 2014, 13 pages.

Gupta et al., "Frac-Fluid Recycling and Water Conservation: A Case History," SPE-119478-PA, Society of Petroleum Engineers, SPE Prod & Oper, Feb. 2010, 25(1):65-69, 5 pages.

Gupta et al., "Surfactant Gel Foam/Emulsion: History and Field Application in the Western Canadian Sedimentary Basin," SPE-97211-MS, Society of Petroleum Engineers, Presented at the SPE Annual Technical Conference and Exhibition, Dallas, Oct. 9-12, 2005, 7 pages.

Gupta, "Unconventional Fracturing Fluids for Tight Gas Reservoirs," SPE-119424-MS, Society of Petroleum Engineers, Presented at the SPE Hydraulic Fracturing Technology Conference, The Woodlands, Texas, Jan. 19-21, 2009, 9 pages.

Gurluk et al., "Enhancing the Performance of Viscoelastic Surfactant Fluids Using Nanoparticles," SPE-164900-MS, Society of Petroleum Engineers, Presented at the EAGE Annual Conference and Exhibition, London, Jun. 10-13, 2013, 15 pages.

Hamley, Introduction to Soft Matter: Synthetic and Biological Self-Assembling Materials, Hoboken, New Jersey: John Wiley & Sons, 2007.

Han et al., "Impact of Depletion on Integrity of Sand Screen in Depleted Unconsolidated Sandstone Formation," ARMA-2015-301, In 49th US Rock Mechanics/Geomechanics Symposium. American Rock Mechanics Association, 2015, 9 pages.

Han et al., "LBM-DEM Modeling of Fluid-Solid Interaction in Porous Media," International Journal for Numerical and Analytical Methods in Geomechanics, 2013, 37: 1391-1407, 17 pages.

Han et al., "Numerical and Experimental Studies of Kerogen Rich Shales on Millimeter-Scale Single-Edge Notched Beam," ARMA-19-211, American Rock Mechanics Association (ARMA), prepared for presentation at the 53rd US Rock Mechanics and Geomechanics Symposium in New York, Jun. 23-26, 2019, 8 pages.

Han et al., "Numerical Modeling of Elastic Hemispherical Contact for Mohr-Coulomb Type Failures in Micro-Geomaterials," Experimental Mechanics, Jun. 2017, 57: 1091-1105, 14 pages.

Han et al., "Application of Silver-Coated Magnetic Microspheres to a SERS-Based Optofluidic Sensor," American Chemical Society Publications (ACS), the Journal of Physical Chemistry C (JPCC), 115: 6290-6296, Mar. 7, 2011, 7 pages.

Harrison et al, "Water-in-Carbon Dioxide Microemulsions with a Fluorocarbon-Hydrocarbon Hybrid Surfactant," Langmuir 1994, 10:10 (3536-3541), 6 pages.

Hay, "Development of an Insitu Rock Shear Testing Device," Dissertation for the Degree of Doctor of Philosophy, University of Florida, Graduate School, 2007, 67 pages.

He et al., "Hydrolysis Effect on the Properties of a New Class of Viscoelastic Surfactant-Based Acid and Damage Caused by the Hydrolysis Products," SPE-165161-MS, Society of Petroleum Engineers, Presented at the SPE European Formation Damage Conference & Exhibition, Noordwijk, The Netherlands, Jun. 5-7, 2013, 17 pages.

Helgeson et al., "Formation and Rheology of Viscoelastic "Double Networks" in Wormlike Micelle-Nanoparticle Mixtures," American Chemical Society, Langmuir, 2010, 26(11):8049-8060, 12 pages.

Hiramatsu and Oka, "Stress around a shaft or level excavated in ground with a three-dimensional stress state," Mem. Fra. Eng. Kyoto Univ. 24, 1962, 2 pages (Abstract).

Hirata et al., "Estimation of Damaged Region Around a Tunnel By Compact VSP Probe Using Super Elastic Alloy," 9th IRSM Congress, International Society for Rock Mechanics, Jan. 1999, 4 pages.

Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, Aug. 2012, 112:044907, 16 pages.

Hoek and Brown, "Empirical Strength Criterion for Rock Masses," Journal of the Geotechnical Engineering Division, Sep. 1980, 20 pages.

Hornby et al., "Anisotropic Effective-Medium Modeling of the Elastic Properties of Shales," Geophysics, Oct. 1994, 59:10 (1570-1583), 14 pages.

Hosemann et al., "An Exploratory Study to Determine Applicability of Nano-Hardness and Microcompression Measurements for Yield Stress Estimation," Science Direct, Journal of Nuclear Materials, 2008, 375: 135-143, 9 pages.

Hosemann et al., "Mechanical Characteristics of SiC Coating Layer in TRISO Fuel Particles," Journal of Nuclear Materials, 2013, 442: 133-142, 10 pages.

Hu et al., "Smart Liquid SERS Substrates based on $Fe_3O_4$/Au Nanoparticles with Reversibility Tunable Enhancement Factor for Practical Quantitative Detection," a natureresearch journal, Scientific Reports, 4:7204, Nov. 27, 2014, 10 pages.

Huang et al., "A theoretical study of the critical external pressure for casing collapse" Journal of Natural Gas Science and Engineering, Nov. 2015, 27:1 (1-8), 8 pages.

Huang et al., "Collapse strength analysis of casing design using finite element method," International Journal of Pressure Vessels and Piping 2000, 77:359-367, 8 pages.

Huang et al., "Do Viscoelastic-Surfactant Diverting Fluids for Acid Treatments Need Internal Breakers?" SPE-112484-MS, Society of Petroleum Engineers (SPE), presented at the SPE International Symposium and Exhibition on Formation Damage Control, Lafayette, Louisiana, Feb. 13-15, 2008, 8 pages.

Huang et al., "Field Case Study on Formation Fines Control with Nanoparticles in Offshore Wells," SPE-135088-MS, Society of Petroleum Engineers (SPE), presented at the SPE Annual Technical Conference and Exhibition, Florence, Italy, Sep. 19-22, 2010, 8 pages.

Huang et al., "Fluid-Loss Control Improves Performance of Viscoelastic Surfactant Fluids," SPE-106227-PA, Society of Petroleum Engineers (SPE), SPE Production and Operations, Feb. 2009, 24:1 (60-65), 6 pages.

Huang et al., "Improving Fracture Fluid Performance and Controlling Formation Fines Migration with the Same Agent: Is It Achievable?" IPTC-17044-MS, International Petroleum Technology Conference, Presented at the International Petroleum Technology Conference, Beijing, Mar. 26-28, 2013, 8 pages.

Huang et al., "Nanoparticle Pseudocrosslinked Micellar Fluids: Optimal Solution for Fluid-Loss Control With Internal Breaking," SPE-128067-MS, Society of Petroleum Engineers (SPE), presented at the SPE International Symposium and Exhibition on Formation Damage Control, Lafayette, Louisiana, Feb. 10-12, 2010, 8 pages.

Huang et al., "Nanotechnology Applications in Viscoelastic-Surfactant Stimulation Fluids," SPE-107728-PA, Society of Petroleum Engineers (SPE), SPE Production and Operations, Nov. 2008, 23:4 (512-517), 6 pages.

Huang et al., "Pressuremeter Tests In Poorly Cemented Weak Rocks," Rock Mechanics for Industry, Amadei, Kranz, Scott and Smealtie (eds), 1999, 6 pages.

Hull and Abousleiman, "Chapter 10: Insights of the Rev of Source Shale from Nano-and Micromechanics," in New Frontiers in Oil and Gas Exploration, Springer International Publishing Switzerland, 2016, 29 pages.

Hull et al, "Nanomechanical Characterization of the Tensile Modulus of Rupture of Kerogen-Rich Shale," SPE 177628, Society of Petroleum Engineers (SPE), presented at the Abu Dhabi Interna-

(56) References Cited

OTHER PUBLICATIONS tional Petroleum Exhibition and Conference, Nov. 9-12, 2015, SPE Journal 2017, 22:4 (1024-1033), 10 pages.

Hull et al., "Bromate Oxidation of Ammonium Salts: In Situ Acid Formation for Reservoir Stimulation," Inorganic Chemistry, 2019, 58, 3007-3014, 8 pages.

Hull et al., "Oxidative Kerogen Degradation: A Potential Approach to Hydraulic Fracturing in Unconventionals," Energy Fuels 2019, 33:6 (4758-4766), 9 pages.

Hull et al., "Recent Advances in Viscoelastic Surfactants for improved Production from Hydrocarbon Reservoirs," SPE 173776, Society of Petroleum Engineers (SPE), presented at the SPE International Symposium on Oilfield Chemistiy, Apr. 13-15, 2015, SPE Journal, 2016, 18 pages.

Huseby et al., "High Quality Flow Information from Tracer Data," SPE-169183-MS, Society of Petroleum Engineers (SPE), presented at the SPE Bergen One Day Seminar, Apr. 2, 2014, 9 pages.

Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.

Imanishi et al., "Wormlike Micelles of Polyoxyethylene Alkyl Ether Mixtures C10E5 + C14E5 and C14E5 + C14E7: Hydrophobic and Hydrophilic Chain Length Dependence of the Micellar Characteristics," Journal of Physical Chemistry B, 2007, 111:1 (62-73), 12 pages.

Inaba et al., "Static Rock Splitter Using Shape Memory Alloy as Pressure Source," Journal of Mining and Materials Processing Institute of Japan, Jan. 1991, 4 pages.

Infante and Chenevert, "Stability of boreholes drilled through salt formations displaying plastic behaviour," SPE Drilling Engineering, vol. 4, No. 1, Mar. 1989, 9 pages.

Iqbal et al., "In situ micro-cantilver tests to study fracture properties of NiAl single crystals," Acta Materialia, Feb. 2012, 60:3 (1193-1200), 8 pages.

Israelachvili et al., "Theory of Self-Assembly of Hydrocarbon Amphiphiles into Micelles and Bilayers," Journal of Chemical Society, Faraday Transactions, 1976, 2:72 (1525-1567), 44 pages.

Itasca, "Fast Lagrangian Analysis of Continua," Version 7.0. Minneapolis, Minnesota, 2011, 22 pages.

itascacg.com [online], "Particle Flow Code, Version 5.0," Itasca Consulting Group, Inc., available on or before Apr. 11, 2014, [retrieved on May 11, 2018], retrieved from URL: <https://www.itascacg.com/software/pfc>, 5 pages.

Itascag.com [online], "Three-dimensional Fast Lagrangian Analysis of Continua (FLAC3D)," available on or before 2012, [retrieved on Jun. 7, 2018], retrieved from URL: < https://www.itascacg.com/software/flac3d>, 4 pages.

Iyengar et al., "Analysis of Crack Propagation in Strain-Softening Beams," Engineering Fracture Mechanics, 2002, 69: 761-778, 18 pages.

Jaeger et al., "Fundamentals of Rock Mechanics," 4th Edition, Wiley, 2007, 486 pages.

Jerke et al., "Flexibility of Charged and Uncharged Polymer-Like Micelles," Langmuir 1998, 14:21 (6013-6024), 12 pages.

Jia et al., "Highly Efficient Extraction of Sulfate Ions with a Tripodal Hexaurea Receptor," Angew. Chem. Int. Ed., 2011, 50: 486-490, 5 pages.

Jianhong et al., "Estimation of the Tensile Elastic Modulus using Brazilian disc by Applying Diametrically Opposed Concentrated Loads," International Journal of Rock Mechanics & Mining Sciences 46:3 (568-576), 2009, 9 pages.

Johnston et al, "Water-in-Carbon Dioxide Microemulsions: An Environment for Hydrophiles Including Proteins," Science, 271:5249 (624-626), Feb. 2, 1996, 3 pages.

Jose et al., "Continuous multi cycle nanoindentation studies on compositionally graded $Ti_{1-x}Al_xN$ multilayer thin films," Materials Science and Engineering: A, Elsevier, Apr. 20, 2011, 528:21 (6438-6444), 7 pages.

Jun et al., "Multifunctional Silver-Embedded Magnetic Nanoparticles as SERS Nanoprobes and Their Applications," Nano Micro Small, Multifunctional Nanoparticles, 6:1 (119-125), Jan. 4, 2010, 7 pages.

Kang et al., "An experimental study on oxidizer treatment used to improve the seepage capacity of coal reservoirs," Natural Gas Industry B, 6: 129-137, Sep. 25, 2018, 9 pages.

Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels, 2006, 20: 301-308, 8 pages.

Kethireddy, "Quantifying the effect of kerogen on Electrical Resistivity Measurements in Organic Rich Source Rocks," Thesis in partial fulfillment of the requirements for the degree of Master of Science, Dec. 2013, 78 pages.

Kim et al., "Numerical analysis of fracture propagation during hydraulic fracturing operations in shale gas systems," International Journal of Rock and Mechanics Mining Sciences, 76: 127-137, 2015, 11 pages.

King, "Thirty Years of Gas Shale Fracturing: What Have We Learned?" SPE-133456, Society of Petroleum Engineers (SPE), presented at the SPE Annual Technical Conference and Exhibition, Sep. 19-22, 2010, 50 pages.

Klapetek, "Chapter 11: Thermal Measurements," in Quantitative Data Processing in Scanning Probe Microscopy: SPM Applications for Nanometrology, 2018, 26 pages.

Kneipp et al., "Single Molecule Detection Using Surface-Enhanced Raman Scattering (SERS)," Physical Review Letters, American Physical Society 78:9, Mar. 3, 1997, 4 pages.

Kolymbas, "Kinematics of Shear Bands," Acta Geotechnica, 2009, 4: 315-318, 4 pages.

Kreh, "Viscoelastic Surfactant-Based Systems in the Niagaran Formation," SPE-125754-MS, Society of Petroleum Engineers (SPE), presented at the SPE Eastern Regional Meeting, Charleston, West Virginia, Sep. 23-25, 2009, 7 pages.

Kumar et al., "Nano to Macro Mechanical Characterization of Shale," SPE 159804, Society of Petroleum Engineers (SPE), presented at the SPE Annual Technical Conference and Exhibition, Oct. 8-10, 2012, 23 pages.

Kuperkar et al., "Viscoelastic Micellar Water/CTAB/NaNO3 Solutions: Rheology, SANS and Cryo-TEM Analysis," Journal of Colloid and Interface Science, 2008, 323:2 (403-409), 7 pages.

Lam et al., "Experiments and Theory in Strain Gradient Elasticity," Journal of Mechanics and Physics Of Solids, 2003, 51: 1477-1508, 32 pages.

Larsen et al., "Changes in the Cross-Link Density of Paris Basin Toarcian Kerogen During Maturation," Organic Geochemistry, 2002, 33:1143-1152, 10 pages.

Lee et al, "Water-in carbon dioxide emulsions: Formation and stability," Langmuir, 1999, 15:20 (6781-6791), 11 pages.

Lee et al., "An Analytical Study on Casing Design for Stabilization of Geothermal Well," Korean J. Air-Conditioning and Ref. Eng., 2012, 11:24, 16 pages.

Leitzell, "Viscoelastic Surfactants: A New Horizon in Fracturing Fluids for Pennsylvania," SPE-111182-MS, Society of Petroleum Engineers (SPE), presented at the Eastern Regional Meeting, Lexington, Kentucky, Oct. 17-19, 2007, 6 pages.

Lewan, "Evaluation of petroleum generation by hydrous pyrolysis experimentation," Phil. Trans. R. Soc. Lond. A, 1985, 315: 123-134, 13 pages.

L'homme, "Initiation of hydraulic fractures in natural sandstones," Master of Science in Geomechanics, University of Minnesota, PhD dissertation, Delft University of Technology, Delft, 2005, 281 pages.

Li et al., "A review of crosslinked fracturing fluids prepared with produced water," KeAi Advanced Research Evolving Science, Southwest Petroleum University, Petroleum 2, 2:4 (313-323), Dec. 2016, 11 pages.

Li et al., "Differentiating Open Natural Fractures from Healed Fractures Using the New, High-Definition Oil-Based Mud Microelectrical Imager-Case Studies from Organic Rich Shales," SPE-174923-MS, Society of Petroleum Engineers (SPE), presented at the SPE Annual Technical Conference and Exhibition, Sep. 28-30, 2015, 16 pages.

(56) References Cited

OTHER PUBLICATIONS

Li et al., "High-Temperature Fracturing Fluids Using Produced Water with Extremely High TDS and Hardness," IPTC-17797-MS, International Petroleum Technology Conference (IPTC), presented at the International Petroleum Technology Conference, Dec. 10-12, 2014, 13 pages.

Li et al., "Mechanical Characterization of Micro/Nanoscale Structures for MEMS/NEMS Applications using Nanoindentation Techniques," Science Direct, Ultramicroscopy, 2003, 97:481-494, 14 pages.

Li et al., "The Brazilian Disc Test for Rock Mechanics Applications: Review and New Insights," Rock Mech Rock Eng, 2013, 46: 269-287, 19 pages.

Li et al., "Well Treatment Fluids Prepared With Oilfield Produced Water: Part II," SPE-133379-MS, Society of Petroleum Engineers (SPE), presented at the SPE Annual Technical Conference and Exhibition, Sep. 19-22, 2010, 7 pages.

Liang et al., "An Experimental Study on interactions between Imbibed Fractured Fluid and Organic-Rich Tight Carbonate Source Rocks," SPE-188338-MS, Society of Petroleum Engineers (SPE), presented at the Abu Dhabi International Petroleum Exhibition and Conference, Nov. 13-16, 2017, 14 pages.

Liu and Abousleiman, "Multiporosity/Multipermeability Inclined-Wellbore Solutions with Mudcake Effects," Society of Petroleum Engineers (SPE), SPE Journal 23:5, Oct. 2018, 25 pages.

Liu and Abousleiman, "N-Porosity and N-Permeability generalized wellbore stability analytical solutions and applications," ARMA 16-417, America Rock Mechanics Association (ARMA), presented at the 50th US Rock Mechanics/Geomechanics Symposium held in Houston, Texas, Jun. 26-29, 2016, 10 pages.

Liu et al., "Applications of nano-indentation methods to estimate nanoscale mechanical properties of shale reservoir rocks," Journal of Natural Gas Science and Engineering, 35: 1310-1319, Sep. 29, 2016, 10 pages.

Liu et al., "Microstructural and geomechanical analysis of Bakken shale at nanoscale," Journal of Petroleum Science and Engineering, 153: 138-144, Mar. 23, 2017, 12 pages.

Liu et al., "Poroelastic Dual-Porosity/Dual-Permeability After-Closure Pressure-Curves Analysis in Hydraulic Fracturing," SPE 181748, Society of Petroleum Engineers (SPE), SPE Journal 2016, 21 pages.

Liu et al., "Safe Drilling in Chemically Active and Naturally Fractured Source Rocks: Analytical Solution and Case Study," IADC/SPE-189658-MS, Society of Petroleum Engineers (SPE), IADC, presented at the IADC/SPE Drilling Conference and Exhibition, Mar. 6-8, 2018, 13 pages.

Liu, "Dimension effect on mechanical behavior of silicon microcantilver beams," Measurement, Oct. 2008, 41:8 (885-895), 11 pages.

Liu, "Elastic Constants Determination and Deformation Observation Using Brazilian Disk Geometiy," Experimental Mechanics, 2010, 50: 1025-1039, 15 pages.

Liu, "Fracture Toughness Assessment of Shales by Nanoindentation," Thesis for the degree of Master of Science in Civil Engineering, Geotechnical Engineering Masters Projects, University of Massachusetts Amherst, Sep. 2015, 80 pages.

Liu, "Micro-cantilver Testing to Evaluate the Mechanical Properties of Thermal Barrier Coatings," 19th European Conference on Fracture (ECF19): Fracture Mechanics for Durability, Reliability and Safety; Conference Proceedings held Aug. 26-31, 2012, Kazan, Russia, 7 pages.

Long et al., "Chapter 2: Advanced Well Stimulation Technologies," in An Independent Scientific Assessment of Well Stimulation in California, vol. I, Well Stimulation Technologies and their Past, Present and Potential Future Use in California, Jan. 2015, 62 pages.

Low, "Advances in Ceramic Matrix Composites: Second Edition," Processing, properties, and applications of SiC, 2018, 11 pages.

Low, "Advances in Ceramics Matrix Composites," Processing. Properties and applications of SiCl/SiC, 10-19, Nanoceramic Matric Composites, 30-41, 2014, 11 pages.

Low, "Ceramic-Matrix Composites: Microstructure, Properties and Applications," Woodhead Publishing Limited, 11-19, 30-40, 2006, 11 pages.

Lu et al, "Fabrication and characterization of ceramic coatings with alumina-silica sol-incorporated a-alumina powder coated on woven quartz fiber fabrics," Ceramics International 39:6 (6041-6050), Aug. 2013, 10 pages.

Lu et al., "Quantitative prediction of seismic rock physics of hybrid tight oil reservoirs of the Permian Lucaogou Formation, Junggar Basin, Northwest China," Journal of Asian Earth Sciences, 2019, 178: 216-223, 8 pages.

Luan et al., "Creation of synthetic samples for physical modelling of natural shale," European Association of Geoscientists and Engineers (EAGE), Geophysical Prospecting 64: 898-914, Jul. 2016, 17 pages.

Lungwitz et al., "Diversion and Cleanup Studies of Viscoelastic Surfactant-Based Self-Diverting Acid," SPE-86504-PA, Society of Petroleum Engineers (SPE), SPE Production and Operations, 2007, 22:1 (121-127), 7 pages.

Luo et al., 2012. "Rheological Behavior and Microstructure of an Anionic Surfactant Micelle Solution with Pyroelectric Nanoparticle," Colloid and Surface A: Physiochemical English Aspects, Feb. 5, 2012, 395: 267-275, 9 pages.

Lyngra et al. "Heavy Oil Characterization: Lessons Learned During Placement of a Horizontal Injector at a Tar/Oil Interface," SPE-172673-MS, Society of Petroleum Engineers (SPE), presented at the SPE Middle East Oil & Gas Show and Conference, Mar. 8-11, 2015, 20 pages.

Lynn et al., "A Core Based Comparison Of The Reaction Characteristics Of Emulsified And In-Situ Gelled Acids In Low Permeability, High Temperature, Gas Bearing Carbonates," SPE-65386-MS, Society of Petroleum Engineers (SPE), presented at the SPE International Symposium on Oilfield Chemistry, Houston, Feb. 13-16, 2001, 16 pages.

Mahabadi et al., "A novel approach for micro-scale characterization and modeling of geomaterials incorporating actual material heterogeneity," (XP002689941) Geophysical Research Letters 39:1 (L01303), Jan. 1, 2012, 6 pages.

Mahabadi et al., "Development of a new fully-parallel finite-discrete element code: Irazu," ARMA-2016-516, American Rock Mechanics Association (ARMA), presented at the 50th US Rock Mechanics/Geomechanics Symposium, Jun. 26-29, 2016, 9 pages.

Mahmoud et al., "Removal of Pyrite and Different Types of Iron Sulfide Scales in Oil and Gas Wells without H2S Generation," IPTC-18279-MS, International Petroleum Technology Conference (IPTC), presented at the International Petroleum Technology Conference, Doha, Qatar, Dec. 6-9, 2015, 8 pages.

Maio et al., "Measuring Fracture Toughness of Coatings using Focused-ion-beam-machined Microbeams," Journal of Materials Research, Feb. 2005, 20:2, 4 pages.

Mao et al., "Chemical and nanometer-scale structure of kerogen and its change during thermal maturation investigated by advanced solid-state 13C NMR spectroscopy," Geochimica et Cosmochimica Acta, 2010, 74(7): 2110-2127, 18 pages.

Marchetti et al., "Fluorous affinity chromatography for enrichment and determination of perfluoroalkyl substances," American Chemical Society (ACS), Annual Review of Analytical Chemistry 84: 7138-7145, Jul. 19, 2012, 8 pages.

Maxwell, "Microseismic hydraulic fracture imaging: The path toward optimizing shale gas production," The Leading Edge, Special Section: Shales, Mar. 2011, 6 pages.

McElfresh et al., "A Single Additive Non-Ionic System for Frac Packing Offers Operators a Small Equipment Footprint and High Compatibility with Brines and Crude Oils," SPE-82245-MS, Society of Petroleum Engineers (SPE), presented at the SPE European Formation Damage Conference, The Hague, The Netherlands, May 13-14, 2003, 11 pages.

McMahon et al., "First 100% Reuse of Bakken Produced Water in Hybrid Treatments Using Inexpensive Polysaccharide Gelling Agents," SPE-173783-MS, Society of Petroleum Engineers (SPE), presented at the SPE International Symposium on Oilfield Chemistry, Apr. 13-15, 2015, 9 pages.

(56) References Cited

OTHER PUBLICATIONS

Medlin et al., "Laboratory investigation of Fracture Initiation and Orientation," SPE-6087-PA, Society of Petroleum Engineers (SPE), Society of Petroleum Engineers Journal, Apr. 1976, 19:02, 16 pages.
Mehrabian and Abousleiman, "Generalized Biot's Theory an Mandel's Problem of Multiple Porosity and Multiple-Permeability Poroelasticity," American Geophysical Union (AGU), Journal of Geological Research: Solid Earth, 119:4 (2745-2763), 2014, 19 pages.
Mesa, "Spherical and rounded cone nano indenters," Micro Star Technologies Inc., available on or before Jan. 23, 2018, 24 pages.
Meyer et al., "Identification of Source Rocks on Wireline Logs by Density/Resistivity and Sonic Transit Time/Resistivity Crossplots," AAPG Bulletin, 1984, 68(2): 121-129, 9 pages.
Meyers et al., "Point load testing of drill cuttings from the determination of rock strength," ARMA-05-712, presented at the 40th U.S. Symposium on Rock Mechanics (USRMS), Alaska Rocks 2005, American Rock Mechanics Association, Jun. 25-29, 2005, 2 pages, (Abstract).
Middleton et al, "Shale gas and non-aqueous fracturing fluids: Opportunities and challenges for supercritical CO 2," Applied Energy, 147: 500-509, 2015, 10 pages.
Mitchell et al., "Chapter 7—Casing and Tubing Design," Properties of Casing and Tubing, Petroleum well construction, 1998, 40 pages.
Mohammed et al., "Casing structural integrity and failure modes in a range of well types—A review," Journal of Natural Gas Science and Engineering, 2019, 68: 102898, 25 pages.
Mohammed et al., "Successful Application of Foamed Viscoelastic Surfactant-Based Acid," SPE-95006-MS, Society of Petroleum Engineers (SPE), presented at the SPE European Formation Damage Conference, Sheveningen, The Netherlands, May 25-27, 2005, 7 pages.
Montgomery and Smith, "Hydraulic Fracturing: History of Enduring Technology," Journal of Petroleum Technology, Dec. 2010, 7 pages.
Montgomery, "Chapter 1: Fracturing Fluids," in Effective and Sustainable Hydraulic Fracturing, Intech, the proceedings of the International Conference for Effective and Sustainable Hydraulic Fracturing (HF2103) on May 20-22, 2013, 23 pages.
Montgomery, "Chapter 2: Fracturing Fluid Components," in Effective and Sustainable Hydraulic Fracturing, Intech, 2013, 21 pages.
Moyer, "A Case for Molecular Recognition in Nuclear Separations: Sulfate Separation from Nuclear Wastes," American Chemical Society (ACS), Inorganic Chemistry, 2012, 52: 3473-3490, 18 pages.
Moyner et al., "The Application of Flow Diagnostics for Reservoir Management," SPE 171557, Society of Petroleum Engineers (SPE), SPE Journal, Apr. 2015, 18 pages.
Nagarajan, "Molecular Packing Parameter and Surfactant Self-Assembly: The Neglected Role of the Surfactant Tail," Langmuir 2002, 18:1 (18-38), 8 pages.
Nasr-El-Din et al., "Investigation and Field Evaluation of Foamed Viscoelastic Surfactant Diversion Fluid Applied During Coiled-Tubing Matrix-Acid Treatment," SPE-99651-MS, Society of Petroleum Engineers (SPE), presented at the SPE/ICoTA Coiled Tubing Conference & Exhibition, The Woodlands, Texas, Apr. 4-5, 2006, 14 pages.
Nasr-El-Din et al., "Lessons Learned and Guidelines for Matrix Acidizing With Viscoelastic Surfactant Diversion in Carbonate Formations," SPE-102468-MS, Society of Petroleum Engineers (SPE), presented at the SPE Annual Technical Conference and Exhibition, San Antonio, Texas, Sep. 24-27, 2006, 11 pages.
Nehmer, "Viscoelastic Gravel-Pack Carrier Fluid," SPE-17168-MS, Society of Petroleum Engineers (SPE), presented at the SPE Formation Damage Control Symposium, Bakersfield, California, Feb. 8-9, 1988, 10 pages.
Nettesheim et al., "Influence of Nanoparticle Addition on the Properties of Wormlike Micellar Solutions," Langmuir 2008, 24:15 (7718-7726), 9 pages.
Nottenburg et al., "Temperature and stress dependence of electrical and mechanical properties of Green River oil shale," Fuel, IPC Science and Technology Press, 58:2 (144-148), Feb. 1, 1979, 5 pages.
Okiongbo et al., "Changes in Type II Kerogen Density as a Function of Maturity: Evidence from the Kimmeridge Clay Formation," Energy Fuels, 2005, 19: 2495-2499, 5 pages.
Oliver and Pharr, "Measurement of hardness and elastic modulus by instrumented indentation: Advances in understanding and refinements to methodology," Journal of Materials Research, 19:1, Jan. 2004, 18 pages.
Oliver, "An Improved Technique for Determining Hardness and Elastic Modulus using Load and Displacement Sensing Indentation Experiments," Journal of Materials Research, Jun. 1992, 7:6, 20 pages.
Ortega et al., "The Effect of Particle Shape and Grain-Scale Properties of Shale: A Micromechanics Approach," International Journal for Numerical and Analytical Methods in Geomechanics, 2010, 34: 1124-1156, 33 pages.
Ortega et al., "The Effect of the Nanogranular Nature of Shale on their Poroelastic Behavior," Acta Geotechnica, 2007, 2: 155-182, 28 pages.
Ortega et al., "The Nanogranular Acoustic Signature of Shale," Geophysics, May-Jun. 2009, 74:3 (D65-D84), 20 pages.
Osman and Pao, "Mud Weight Prediction for Offshore Drilling," 8 pages.
Ottesen, "Wellbore Stability in Fractured Rock," IADC/SPE 128728, International Association of Drilling Contractors (IADC), Society of Petroleum Engineers (SPE), presented at the 2010 IADC/SPE Drilling Conference and Exhibition, Louisiana, Feb. 2-4, 2010, 8 pages.
Palisch et al., "Determining Realistic Fracture Conductivity and Understanding Its Impact on Well Performance—Theory and Field Examples," SPE-106301-MS, Society of Petroleum Engineers (SPE), presented at the SPE Hydraulic Fracturing Technology Conference, College Station, Texas, Jan. 29-31, 2007, 13 pages.
Pandey et al., "Fracture Stimulation Utilizing a Viscoelastic-Surfactant Based System in the Morrow Sands in Southeast New Mexico," SPE-102677-MS, Society of Petroleum Engineers (SPE), presented at the International Symposium on Oilfield Chemistry, Houston, Feb. 28- Mar. 2, 2007, 8 pages.
Pant, "Nanoindentation characterization of clay minerals and clay-based hybrid bio-geomaterials," dissertation for degree of Doctor of Philosophy in the Department of Civil and Environmental Engineering at the Louisiana State University and Agricultural and Medical College, Dec. 2013, 111 pages.
Passey et al., "From Oil-Prone Source Rock to Gas-Producing Shale Reservoir—Geologic and Petrophysical Characterization of Unconventional Shale-Gas Reservoirs," SPE-131350, Society of Petroleum Engineers (SPE), presented at the CPS/SPE International Oil & Gas Conference and Exhibition, Beijing, China, Jun. 8-10, 2010, 29 pages.
Patel et al., "Analysis of US Hydraulic Fracturing Fluid System and Proppant Trends," SPE 168645, Society of Petroleum Engineers (SPE), presented at the SPE Hydraulic Fracturing Technology Conference, Feb. 4-6, 2014, 20 pages.
Petoud et al., "Brilliant SM, Eu, Tb, and Dy Chiral Lanthanide Complexes with Strong Circularly Polarized Luminescence," Journal for the American Chemical Society (JACS), 129: 77-83, Dec. 15, 2006, 7 pages.
petrowiki.org [online], "Fluid flow in naturally fractured reservoirs," retrieved from URL <https://petrowiki.org/Fluid_flow_in_naturally_fractured_reservoirs>, available on or before Jul. 16, 2015, retrieved on Nov. 11, 2019, 12 pages.
Pittman, "Investigation of Abrasive-Laden-Fluid Method for Perforation and Fracture Initiation," SPE 1607-G, Society of Petroleum Engineers (SPE), presented at the 31st Annual California Regional Fall Meeting of SPE, Oct. 20-21, 1960, Journal of Petroleum Technology, May 1961, 13:5 (489-495), 7 pages.
Podio et al., "Dynamic Properties of Dry and Water-Saturated Green River Shale under Stress," SPE 1825, Society of Petroleum Engineers (SPE), presented at SPE 42nd Annual Fall Meeting, Oct. 1-4, 1967, Society of Petroleum Engineers Journal, Jun. 1968, 16 pages.

(56) References Cited

OTHER PUBLICATIONS

Pollard et al., "Fundamentals of Structural Geology," Cambridge University Press, Sep. 1, 2005, 291, 3 pages.

Pollock and Hammiche, "Micro-thermal analysis: techniques and applications," Journal of Physics D: Applied Physics, 34.9 (R23-R53), 2001, 31 pages.

Poon et al., "An Analysis of Nanoindentation in Linearly Elastic Solids," International Journal of Solids and Structures, Dec. 2008, 45:24 (6018-6033), 16 pages.

Qin et al, "Applicability of nonionic surfactant alkyl poly glucoside in preparation of liquid CO2 emulsion," Journal of CO2 Utilization, 2018, 26: 503-510, 8 pages.

Raghavan et al., "Highly Viscoelastic Wormlike Micellar Solutions Formed by Cationic Surfactants with Long Unsaturated Tails," Langmuir 2001, 17:2 (300-306), 7 pages.

Rajbanshi et al., "Sulfate Separation from Aqueous Alkaline Solutions by Selective Crystallization of Alkali Metal Coordination Capsules," American Chemical Society Publications (ACS), Crystal Growth and Design, 2011, 11: 2702-2706, 5 pages.

Rawat et al., "Case Evaluating Acid Stimulated Multilayered Well Performance in Offshore Carbonate Reservoir: Bombay High," OTC-25018-MS, Offshore Technology Conference (OTC), presented at the Offshore Technology Conference—Asia, Kuala Lumpur, Mar. 25-28, 2014.

Ribeiro and Sharma, "Fluid Selection for Energized Fracture Treatments," SPE 163867, Society of Petroleum Engineers (SPE), presented at the SPE Hydraulic Fracturing Technology Conference, Feb. 4-6, 2013, 11 pages.

Richard et al, "Slow Relaxation and Compaction of Granular Systems," Nature Materials, Feb. 2005, 4, 8 pages.

Rodriguez et al., "Imagining techniques for analyzing shale pores and minerals," National Energy Technology Laboratory, Dec. 2, 2014, 44 pages.

Rostami et al., "DABCO tribromide immobilized on magnetic nanoparticle as a recyclable catalyst for the chemoselective oxidation of sulfide using H2O2 under metaland solvent-free condition," Catal. Commun. 2014, 43: 16-20, 20 pages.

Rowan et al., "Dynamic Covalent Chemistry," Angewante Chemie International Edition, 41: 898-952, Mar. 15, 2002, 55 pages.

Ryoo et al, "Water-in-Carbon Dioxide Microemulsions with Methylated Branched Hydrocarbon Surfactants," Industrial & Engineering Chemistry Research 2003, 42:25 (6348-6358), 11 pages.

Sagisaka et al, "Effect of Fluorocarbon and Hydrocarbon Chain Lengths In Hybrid Surfactants for Supercritical CO2," Langmuir 2015, 31(27): 7479-7487, 36 pages.

Sagisaka et al, "Nanostructures in Water-in-CO2 Microemulsions Stabilized by Double-Chain Fluorocarbon Solubilizers," Langmuir 2013, 29(25): 7618-7628, 11 pages.

Sagisaka et al., "A New Class of Amphiphiles Designed for Use in Water-in-Supercritical CO2 Microemulsions," Langmuir 2016, 32(47): 12413-12422, 44 pages.

Samuel et al., "A New Solids-Free Non-Damaging High Temperature Lost-Circulation Pill: Development and First Field Applications," SPE-81494-MS, Society of Petroleum Engineers (SPE), presented at the Middle East Oil Show, Bahrain, 9-12 Jun. 9-12, 2003, 12 pages.

Samuel et al., "Polymer-Free Fluid for Fracturing Applications," SPE-59478-PA, Society of Petroleum Engineers (SPE), SPE Drill & Compl 1999, 14:4 (240-246), 7 pages.

Samuel et al., "Polymer-Free Fluid for Hydraulic Fracturing," SPE-38622-MS, Society of Petroleum Engineers (SPE), presented at the SPE Annual Technical Conference and Exhibition, San Antonio, Texas, Oct. 5-8, 1997, 7 pages.

Samuel et al., "Viscoelastic Surfactant Fracturing Fluids: Application in Low Permeability Reservoirs," SPE-60322-MS, Society of Petroleum Engineers (SPE), presented at the SPE Rocky Mountain Regional/Low-Permeability Reservoirs Symposium and Exhibition, Denver, 12-15 Mar. 12-15, 2000, 7 pages.

Santarelli et al., "Drilling through Highly Fractured Formations: A Problem, a Model, and a Cure," Society of Petroleum Engineers (SPE), presented at the 67th Annual Technical Conference and Exhibition of the Society of Petroleum Engineers, Washington D.C., Oct. 4-7, 1992, 10 pages.

Sayed and Al-Muntasheri, "A Safer Generation of Wettability Alteration Chemical Treatments," SPE-184566-MS, Society of Petroleum Engineers (SPE), presented at the SPE International Conference on Oilfield Chemistry, Apr. 3-5, 2017, 25 pages.

Schubert et al., "The Microstructure and Rheology of Mixed Cationic/Anionic Wormlike Micelles," Langmuir 2003, 19:10 (4079-4089), 11 pages.

Selvin et al., "Principles and biophysical applications of lanthanide-based probes," Annual Review of Biophysics and Biomolecular Structure, Jun. 2002, 31:275-302, 28 pages.

Semmelbeck et al., "Novel CO2-Emulsified Viscoelastic Surfactant Fracturing Fluid System Enables Commercial Production from Bypassed Pay in the Olmos Formation of South Texas," SPE-100524-MS, Society of Petroleum Engineers (SPE), presented at the SPE Gas Technology Symposium, Calgary, May 15-17, 2006, 8 pages.

Sepulveda et al., "Oil-Based Foam and Proper Underbalanced-Drilling Practices Improve Drilling Efficiency in a Deep Gulf Coast Well," SPE 115536, Society of Petroleum Engineers (SPE), presented at the 2008 SPE Annual Technical Conference and Exhibition in Denver, Colorado, Sep. 21-24, 2008, 8 pages.

Serra, "No Pressure Transient Analysis Methods for Naturally Fractured Reservoirs," (includes associated papers 12940 and 13014), Journal of Petroleum Technology, Dec. 1983, 35:12, Society of Petroleum Engineers, 18 pages.

Serres-Piole et al., "Water tracers in oilfield applications: Guidelines," Elsevier Ltd., Journal of Science and Engineering, Nov. 2012, 98-99:22-39, 18 pages.

Shabro et al., "Pore-scaling modeling of electrical resistivity and permeability in FIB-SEM images of organic mudrock," Geophysics, Society of Exploration Geophysicists 79:5 (D289-D299), Sep.-Oct. 2014, 11 pages.

Shahid et al., "Natural-fracture reactivation in shale gas reservoir and resulting microseismicity," SPE 178437, Journal of Canadian Petroleum Technology, Nov. 2015, 54:06, 10 pages.

Shashkina et al., "Rheology of Viscoelastic Solutions of Cationic Surfactant. Effect of Added Associating Polymer," Langmuir 2005, 21:4 (1524-1530), 7 pages.

Shi et al., "Research and Application of Drilling Technology of Extended-reach Horizontally-intersected Well Used to Extract Coalbed Methane," 2011 Xi'an International Conference on Fine Geological Exploration and Groundwater & Gas Hazards Control in Coal Mines, Procedia Earth and Planetaiy Science, Dec. 2011, 3: 446-454, 9 pages.

Shin et al., "Development and Testing of Microcompression for Post Irradiation Characterization of ODS Steels," Journal of Nuclear Materials, 2014, 444: 43-48, 6 pages.

Shook et al., "Determining Reservoir Properties and Flood Performance from Tracer Test Analysis," SPE 124614, Society of Petroleum Engineers (SPE), presented at SPE Annual Technical Conference and Exhibition, Oct. 4-7, 2009, 19 pages.

Shukla et al., "Nanoindentation Studies on Shales," ARMA 13-578, American Rock Mechanics Association (ARMA), presented at the 47th US Rock Mechanics/Geomechanics Symposium, Jun. 23-26, 2013, 10 pages.

Siddig et al., "A review of different approaches for water-based drilling fluid filter cake removal," Journal of Petroleum Science and Engineering, Apr. 2020.

Sierra et al., "Woodford Shale Mechanical Properties and the Impacts of Lithofacies," ARMA 10-461, American Rock Mechanics Association (ARMA), presented at the 44th US Rock Mechanics Symposium and 5th US-Canada Rock mechanics Symposium, Jun. 27-30, 2010, 10 pages.

Singh et al., "Facies classification based on seismic waveform," presented at the 5th Conference & Exposition on Petroleum Geophysics, Jan. 15-17, 2004, 456-462, 7 pages.

Siskin et al., "Reactivity of organic compounds in hot water: geochemical and technological implications," Science, Oct. 11, 1991, 254, 8 pages.

(56) References Cited

OTHER PUBLICATIONS

Slatt et al., "Merging Sequence Stratigraphy and Geomechanics for Unconventional Gas Shales," The Leading Edge, Special Section: Shales, Mar. 2011, 8 pages.

Slatt et al., "Outcrop/Behind Outcrop (Quarry), Multiscale Characterization of the Woodford Gas Shale," Chapter 12 in Shale-Reservoirs—Giant Resomces for the 21st Century: AAPG Memoir, 2011, 97: 1-21, 22 pages.

Sone et al., "Mechanical Properties of Shale-Gas Reservoir Rocks—Part 1: Static and Dynamic Elastic Properties and Anisotropy," Geophysics, Sep.-Oct. 2013, 78:5 (D381-D392), 12 pages.

Sone et al., "Mechanical Properties of Shale-Gas Reservoir Rocks—Part 2: Ductile Creep, Brittle Strength, and their Relation to the Elastic Modulus," Geophysics, Sep.-Oct. 2013, 78:5 (D393-D402), 10 pages.

Song et al., "SERS-Encoded Nanogapped Plasmonic Nanoparticles: Growth of Metallic Nanoshell by Templating Redox-Active Polymer Brushes," Journal of the American Chemical Society (JACS), Apr. 28, 2014, 136: 6838-6841, 4 pages.

Soni, "LPG-Based Fracturing: An Alternative Fracturing Technique in Shale Reservoirs," IADC/SPE-170542-MS, Society of Petroleum Engineers (Spe), IADC/SPE Asia Pacific Drilling Technology Conference, Aug. 25-27, 2014, 7 pages.

Stewart et al., "Use of a Solids-Free Viscous Carrying Fluid in Fracturing Applications: An Economic and Productivity Comparison in Shallow Completions," SPE-30114-MS, Society of Petroleum Engineers (SPE), presented at the SPE European Formation Damage Control Conference, Hague, The Netherlands, May 15-16, 1994, 14 pages.

Stiles et al., "Surface-enhanced Raman Spectroscopty," Annual Review of Analytical Chemistry, Mar. 18, 2008, 1:601-26, 29 pages.

Sullivan et al., "Optimization of a Viscoelastic Surfactant (VES) Fracturing Fluid for Application in High-Permeability Formations," SPE-98338-MS, Society of Petroleum Engineers (SPE), presented at the SPE International Symposium and Exhibition on Formation Damage Control, Lafayette, Louisiana, Feb. 15-17, 2006, 8 pages.

Tabatabaei et al., "Well performance diagnosis with temperature profile measurements," SPE 147448, Society of Petroleum Engineers (SPE), in SPE Annual Technical Conference and Exhibition, Oct. 30-Nov. 2, 2011, published Jan. 2011, 16 pages.

Taheri et al., "Investigation of rock salt layer creep and its effects on casing collapse," International Journal of Mining Science and Technology, 2020, 9 pages.

Tathed et al., "Hydrocarbon saturation in Bakken Petroleum System based on joint inversion of resistivity and dielectric dispersion logs," Fuel, Dec. 2018, 233: 45-55, 11 pages.

Taylor et al., "Laboratory Evaluation of In-Situ Gelled Acids for Carbonate Reservoirs," SPE-71694-MS, Society of Petroleum Engineers (SPE), presented at the SPE Annual Technical Conference and Exhibition, New Orleans, Sep. 30-Oct. 3, 2001, 10 pages.

Tian et al., "Off-Resonant Gold Superstructures as Ultrabright Minimally Invasive Surface-Enhanced Raman Scattering (SERS) Probes," American Chemical Society (ACS), Chemistry of Materials (CM), Jul. 2015, 27: 5678-5684, 7 pages.

Trippetta et al., "The seismic signature of heavy oil on carbonate reservoir through laboratory experiments and AVA modelling," Journal of Petroleum Science and Engineering, 2019, 177: 849-860, 12 pages.

Ulboldi et al., "Rock strength measurement on cuttings as input data for optimizing drill bit selection," SPE 56441, Society of Petroleum Engineers (SPE), presented at the 1999 SPE Annual Technical Conference and Exhibition, Oct. 3-6, 1999, 9 pages.

Uleberg and Kleppe, "Dual Porosity, Dual Permeability Formulation for Fractured Reservoir Simulation," TPG4150, Reservoir Recovery Techniques, Combined Gas/Water Injection Subprogram, 1996, 12 pages.

Ulm et al., "Material Invariant Poromechanics Properties of Shales," Poromechanics III: Biot Centennial, Proceedings of the 3rd Biot Conference on Poromechanics, 2005, 8 pages.

Ulm et al., "The Nanogranular Nature of Shale," Acta Geotechnica, 2006, 12 pages.

Van Zanten et al., "Advanced Viscoelastic Surfactant Gels for High-Density Completion Brines," SPE-143844-MS, Society of Petroleum Engineers (SPE), presented at the SPE European Formation Damage Control Conference, Noordwijk, The Netherlands, Jun. 7-10, 2011, 7 pages.

Van Zanten, "Stabilizing Viscoelastic Surfactants in High-Density Brines," SPE-141447-PA, Society of Petroleum Engineers (SPE), SPE Drill & Compl 26:4 (499-505), 7 pages.

Vanlandingham, "Review of Instrumented Indentation," Journal of Research of the National Institute of Standards and Technology, July-Aug. 2003, 108:4 (249-265), 17 pages.

Vernik et al., "Ultrasonic Velocity and Anisotropy of Hydrocarbon Source Rocks," Geophysics, May 1992, 57:5 (727-735), 9 pages.

Walters et al., "Kinetic rheology of hydraulic fracturing fluids," SPE 71660, Society of Petroleum Engineers (SPE), SPE Annual Technical Conference and Exhibition, Sep. 30-Oct. 3, 2001, 12 pages.

Wang and Samuel, "Geomechanical Modelling of Wellbore Stability in Salt Formations, 3D Geomechanical Modeling of Salt-Creep Behavior on Wellbore Casing for Presalt Reservoirs," SPE Drilling and Completion, 31(04): 261-272, Sep. 2013, 13 pages.

Wang et al, "A Feasibility Analysis on Shale Gas Exploitation with Supercritical Carbon Dioxide," Energy Sources, Part A: Recovery, Utilization, and Environmental Effects 2012, 34:15 (1426-1435), 11 pages.

Wang et al., "A New Viscoelastic Surfactant for High Temperature Carbonate Acidizing," SPE-160884-MS, Society of Petroleum Engineers (SPE), presented at the SPE Saudi Arabia Section Technical Symposium and Exhibition, Al-Khobar, Saudi Arabia, Apr. 8-11, 2012, 18 pages.

Wang et al., "A Numerical Study of Factors Affecting the Characterization of Nanoindentation on Silicon," Materials Science and Engineering: A, Feb. 25, 2007, 447:1 (244-253), 10 pages.

Wang et al., "Characterization of electrical properties of organic-rich shales at nano/micro scales," Marine and Petroleum Geology, 86:563-572, Jun. 16, 2017, 10 pages.

Wang et al., "Iron Sulfide Scale Dissolvers: How Effective Are They?" SPE-168063-MS, Society of Petroleum Engineers (SPE), presented at the SPE Saudi Arabia section Annual Technical Symposium and Exhibition, Khobar, Saudi Arabia, May 19-22, 2013, 22 pages.

Wang et al., "The Flattened Brazilian Disc Specimen Used for Testing Elastic Modulus, Tensile Strength and Fracture Toughness of Brittle Rocks: Analytical and Numerical Results," International Journal of Rock Mechanics and Mining Sciences, 2004, 41:2 (245-253), 9 pages.

Warpinski, "Understanding Hydraulic Fracture Growth, Effectiveness, and Safety Through Microseismic Monitoring," Chapter 6, in Effective and Sustainable Hydraulic Fracturing, Intech, May 17, 2013, 14 pages.

Warren and Root, "The Behavior of Naturally Fractured Reservoirs," SPE 426, Society of Petroleum Engineers (SPE), SPE Journal, Sep. 1963, 3:3 (245-255), 11 pages.

Wegst et al., "Bioinspired Structural Materials," Nature Materials, Jan. 2015, 14, 14 pages.

Weijermars et al., "Closure of open wellbores in creeping salt sheets" Geophysical Journal International, 196, 279-290, 2014, 12 pages.

Welton et al., "Anionic Surfactant Gel Treatment Fluid," SPE-105815-MS, Society of Petroleum Engineers (SPE), presented at the SPE International Symposium on Oilfield Chemistry, Houston, Feb. 28- Mar. 2, 2007, 8 pages.

Wenk et al., "Preferred Orientation and Elastic Anisotropy of Illite-Rich Shale," Geophysics, Mar.-Apr. 2007, 72:2 (E69-E75), 7 pages.

Wessels et al., "Identifying fault activation during hydraulic stimulation in the Barnett shale: source mechanisms, b values, and energy release analyses of microseismicity," presented at the SEG San Antonio 2011 Annual Meeting, Sep. 18-23, 2011, 5 pages.

Wilson and Aifantis, "On the Theory of Consolidation with Double Porosity," International Journal of Engineering Science, 1982, 20:9 (1009-1035), 27 pages.

(56) References Cited

OTHER PUBLICATIONS

Wilson et al., "Fracture testing of bulk silicon microcantilever beams subjected to a side load," Journal of Microelectromechanical Systems, Sep. 1996, 5:3, 9 pages.

Winkler et al, "Effects of borehole stress concentrations on dipole anisotropy measurements," Geophysics, Jan. 1998, 63:1 (11-17), 7 pages.

Witten et al., "Structured Fluids: Polymers, Colloids, Surfactants," New York: Oxford University Press, 2010, 231 pages.

Wu et al., "A reusable biosensor chip for SERS-fluorescence dual mode immunoassay," Proc. SPIE 9543:954317-1, Third International Symposium on Laser Interaction with Matter, LIMIS 2014, May 4, 2015, 6 pages.

Wu et al., "A SERS-Assisted 3D Barcode Chip for High-Throughput Biosensing," Nano Micro Small Journal, Jun. 11, 2015, 11:23 (2798-2806), 9 pages.

Wu et al., "Extraction of kerogen from oil shale with supercritical carbon dioxide: Molecular dynamics simulations," the Journal of Supercritical Fluids, 107: 499-506, Jan. 2016, 8 pages.

Wurster et al., "Characterization of the fracture toughness of microsized tungsten single crystal notched specimens," Philosophical Magazine, May 2012, 92:14, 23 pages.

Wurzenberger et al., "Nitrogen-Rich Copper(II) Bromate Complexes: an Exotic Class of Primary Explosives," Journal of Inorganic Chemistiy, 2018, 57: 7940-7949, 10 pages.

Xi et al., "Uncertainty Analysis Method for Intersecting Process of U-Shaped Horizontal Wells," Arabian Journal for Science and Engineering, 40:2 (615-625), Feb. 2015, 12 pages.

Xu et al., "Anisotropic elasticity of jarosite: A high-P synchrotron XRD study," American Mineralogist, 2010, 95:1 (19-23), 5 pages.

Xu et al., "Measurement of two-photon excitation cross sections of molecular fluorophores with data from 690 to 1050 nm," Journal of the Optical Society of America B, Mar. 1996, 13:3, 11 pages.

Yang et al., "Nanoscale geochemical and geomechanical characterization of organic matter in shale," Nature Communications, Dec. 19, 2017, 8:2179, 9 pages.

Yang et al., "Viscoelastic Evaluation of Gemini Surfactant Gel for Hydraulic Fracturing," SPE-165177-MS, Society of Petroleum Engineers (SPE), presented at the SPE European Formation Damage Conference and Exhibition, Noordwijk, The Netherlands, Jun. 5-7, 2013, 5 pages.

Yoldas, "Alumina gels that form porous transparent Al2O2," Journal of Materials Science, 1975, 10: 1856-1860, 5 pages.

Yu et al., "Impact of Hydrolysis at High Temperatures on the Apparent Viscosity of Carboxybetaine Viscoelastic Surfactant-Based Acid: Experimental and Molecular Dynamics Simulation Studies," SPE-142264-PA, Society of Petroleum Engineers (SPE), SPE J. 2012, 17:4 (1119-1130), 12 pages.

Yu et al., "Propagation and Retention of Viscoelastic Surfactants Following Matrix-Acidizing Treatments in Carbonate Cores," SPE-128047-PA, Society of Petroleum Engineers (SPE), SPE J. 2011, 16:4 (993-1001), 9 pages.

Zamberi et al., "Improved Reservoir Surveillance Through Injected Tracers In A Saudi Arabian Field: Case Study," SPE 166005, Society of Petroleum Engineers (SPE), presented at SPE Reservoir Characterization and Simulation Conference and Exhibition, Sep. 16-18, 2013, 15 pages.

Zeilinger et al., "Improved Prediction of Foam Diversion in Matrix Acidizing," SPE-29529-MS, Society of Petroleum Engineers (SPE), presented at the Production Symposium, Oklahoma City, Oklahoma, Apr. 2-4, 1995, 13 pages.

Zemel, "Chapter 3: Interwell Water Tracers," Tracers in the Oil Field, 43:1, Elsevier Science, Jan. 13, 1995, 47 pages.

Zeszotarski et al., "Imaging and Mechanical Property Measurements of Kerogen via Nanoindentation," Geochimica et Cosmochimica Acta, 2004, 68:20, 7 pages.

Zhao et al., "A New Fracturing Fluid for HP/HT Applications," SPE-174204-MS, Society of Petroleum Engineers (SPE), presented at the SPE European Formation Damage Conference and Exhibition, Budapest, Hungary, Jun. 3-5, 2015, 17 pages.

Zhou et al., "Upconversion luminescent materials: advances and applications," American Chemical Society (ACS), Chemical Reviews, Jan. 14, 2015, 115: 395-465, 71 pages.

Zielinski et al, "A Small-Angle Neutron Scattering Study of Water in Carbon Dioxide Microemulsions," Langmuir 1997, 13(15): 3934-3937, 4 pages.

Zimmerman and Bodvarsson, "Hydraulic Conductivity of Rock Fractures," transport in Porous Media, Jan. 1996, 23: 1-30, 31 pages.

Zwanenburg et al., "Well Abandonment: Abrasive Jetting to Access a Poorly Cemented Annulus and Placing a Sealant," SPE-159216-MS, Society of Petroleum Engineers (SPE), presented at the SPE Annual Technical Conference and Exhibition, Oct. 8-10, 2012, 11 pages.

\* cited by examiner

| Input Parameters | | |
|---|---|---|
| No leakoff | | |
| Kerogen density | 1.3 | kg/m³ |
| Kerogen wt% | 7 | % |
| Kerogen vol% | 14 | % |
| Fracture length | 300 | m |
| Fracture height | 10 | m |
| Total porosity | 25 | % |
| % Connected porosity | 20 | % |
| Additive/Kerogen ratio | 500 | kg/kg |
| Fracture face depth affected | 0.005 | m |
| Fractured kerogen porosity | 50 | % |

602: Kerogen density, Kerogen wt%, Kerogen vol%
604: Fracture length, Fracture height
606: Total porosity, % Connected porosity
608: Additive/Kerogen ratio
610: Fracture face depth affected, Fractured kerogen porosity

FIG. 6

Dataset Retrieval

| | |
|---|---|
| Field | Field A ▼ |
| Well | Well #1 ▼ |
| Temperature | 100 ▼ °C |
| Kerogen Maturity | Early Oil ▼ |

Treatment Effects

| | | |
|---|---|---|
| Bulk formation volume affected | 30.00 | $m^3$ |
| Void space created | 2.10 | $m^3$ |
| Connected porosity before | 5.00 | % |
| Connected porosity after | 12.00 | % |

1000 (first two rows)
1002 (last two rows)

DETERMINING EFFECT OF OXIDATIVE HYDRAULIC FRACTURING

TECHNICAL FIELD

This disclosure relates to oxidative hydraulic fracturing of unconventional formations.

BACKGROUND

Hydraulic fracturing employs fluid and material to generate fractures in a subterranean formation to stimulate production from oil and gas wells. Hydraulic fracturing is a well-stimulation technique in which rock is fractured by a pressurized fluid that may be a fracturing fluid. The process can involve the pressure injection of fracturing fluid into a wellbore to generate cracks in the deep-rock formations through which natural gas, petroleum, and brine will flow more freely. The hydraulic fracturing typically generates paths that increase the rate at which production fluids, such as crude oil or natural gas, can be produced from the reservoir formations. The amount of increased production may be related to the amount of fracturing. Proppant may be employed to maintain the fractures as pressure depletes in the well during hydrocarbon production. The proppant may resist formation closure stresses to keep fractures open.

SUMMARY

An aspect relates to a method of estimating enhancement of porosity and permeability of a subterranean formation due to presence of an oxidizer in a fracturing fluid. The method includes determining kerogen volume percent (vol %) in the subterranean formation and estimating fractured kerogen porosity, wherein the fractured kerogen porosity is associated with presence of the oxidizer. The method includes determining an increase in connected porosity in the subterranean formation correlative with the kerogen vol % and the fractured kerogen porosity.

Another aspect is a method of evaluating effect of hydraulic fracturing fluid having an oxidizer on a subterranean formation. The method includes determining porosity of the subterranean formation before hydraulic fracturing the subterranean formation with the hydraulic fracturing fluid comprising the oxidizer, determining percent of the porosity that is connected porosity, and determining an increase in the connected porosity correlative with kerogen vol % in the subterranean formation and fractured kerogen porosity due to the oxidizer.

Yet another aspect is a method of determining effect of oxidative hydraulic fracturing on a subterranean formation. The method includes determining porosity of the subterranean formation before the oxidative hydraulic fracturing, determining percent of the porosity that is connected porosity, determining kerogen volume percent (vol %) in the subterranean formation, and estimating, via imaging of a sample of the subterranean formation, fractured kerogen porosity caused by an oxidizer of a fracturing fluid.

The details of one or more implementations are set forth in the accompanying drawings and the description below. Other features and advantages will be apparent from the description and drawings, and from the claims.

BRIEF DESCRIPTION OF DRAWINGS

FIG. 6 is a diagram of an example list of input parameters that may be utilized to calculate and determine effects (e.g., permeability enhancement) of an oxidizing fracturing fluid on an unconventional rock formation.

FIG. 9 is a diagram of a user-interface (e.g., input pane) for dataset retrieval.

FIG. 10 is a diagram of a user-interface (e.g., output pane) for presenting treatment effects as calculated or determined, such as based at least in part on the input parameters of FIG. 6.

DETAILED DESCRIPTION

Figure 1:
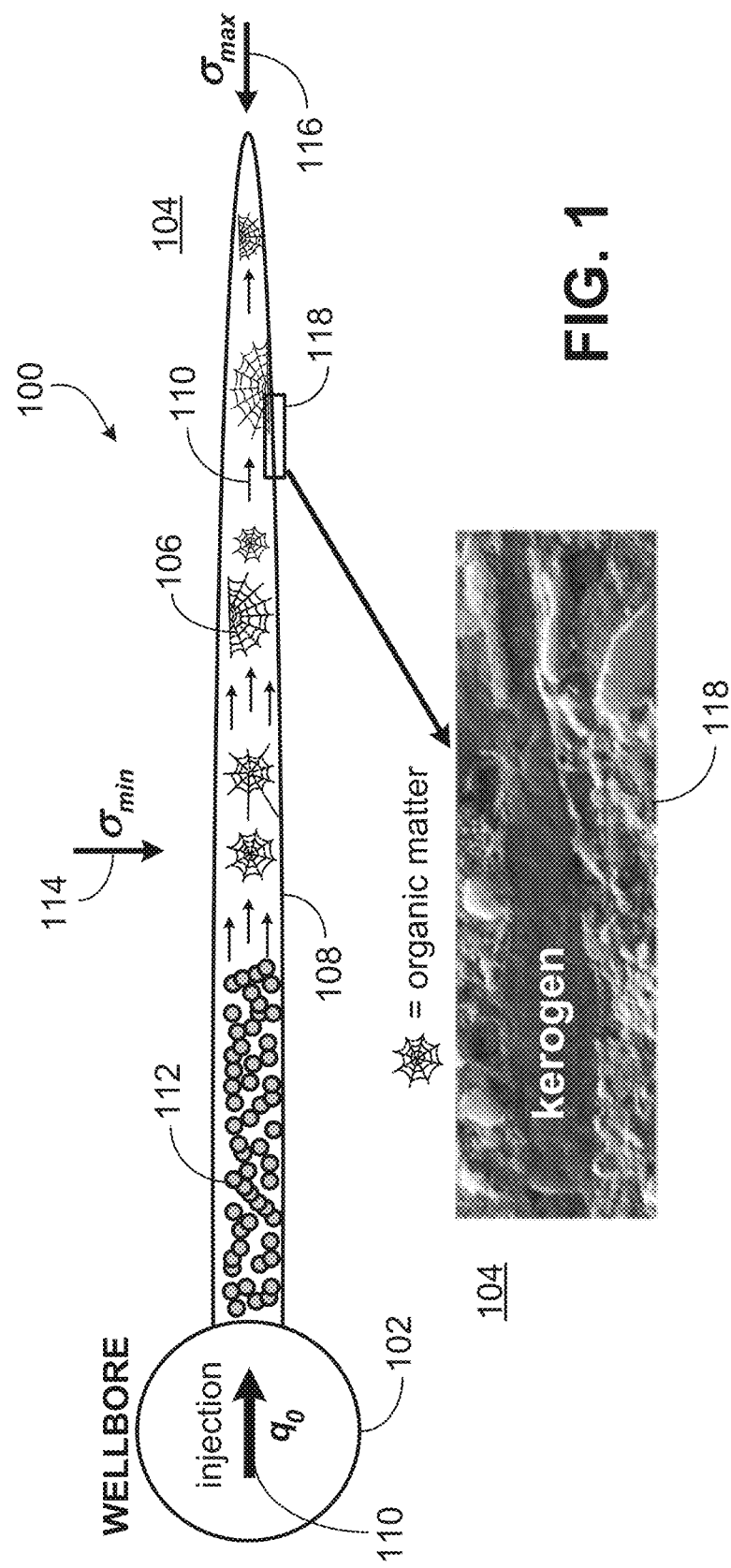
FIG. 1 is a diagram of a well having a wellbore formed in a subterranean formation having organic matter, such as kerogen.

Some aspects of the present disclosure are directed to determining porosity and permeability enhancement of hydraulically-fractured unconventional formations, such as hydraulically-fractured kerogen-rich shales. The permeability enhancement may be characterized as the increase (difference or ratio) in permeability and can be related to increase in connected porosity. The disclosure relates to oxidative treatment of unconventional formations in hydraulic fracturing with oxidative treatment fluids (e.g., fracturing fluids having an oxidizer). The permeability enhancement (or increase in connected porosity) may be determined based on comparison of hydraulically fracturing the subterranean formation with a fracturing fluid having an oxidizer versus the subterranean formation not hydraulically fractured. It can be noted that the permeability enhancement from an oxidative hydraulic fracturing treatment is expected to be higher than the permeability enhancement from a non-oxidative hydraulic fracturing treatment.

Embodiments of the present techniques may estimate effect (e.g., enhancement of porosity and permeability) on a subterranean formation due to presence of an oxidizer in a fracturing fluid. The technique may include determining kerogen volume percent (vol %) in the subterranean formation and estimating fractured kerogen porosity associated with presence of the oxidizer. In implementations, an increase in connected porosity in the subterranean formation may be determined correlative with the kerogen vol % and the fractured kerogen porosity. As discussed below, the fractured kerogen porosity may be estimated via imaging. The kerogen vol % may be based on kerogen weight percent (wt %) in the subterranean formation and kerogen density of kerogen in the subterranean formation. In certain implementations, the kerogen wt % and the kerogen maturity may be estimated via pyrolysis testing. The kerogen density may be estimated based on the kerogen maturity. The fracturing fluid having the oxidizer may be utilized in hydraulic fracturing of the subterranean formation.

Hydraulic fracturing may allow for the recovery of crude oil and natural gas from unconventional formations that geologists once believed were impossible to produce. Unconventional source rocks may be fine-grained, organic-rich sedimentary deposits, such as shales and mud rocks. Although unconventional rock formations or reservoirs are porous composites, their very small pore sizes and low permeability make them relatively resistant to economical hydrocarbon flow. The low permeability of the shale reservoir means that oil and gas typically are not economically produced from the well geometry, but rather through hydraulically fractured and stimulated wells. Unconventional formations typically include organic material (e.g., kerogen) intertwined with the rock matrix and the pores. In some circumstances, high-yield unconventional formations may be characterized or labeled as a kerogen-rich shale (KRS). The organic components of the source shale may include the hydrocarbon-source material kerogen and kerogen-produced components bitumen and pyrobitumen. Kerogen is a solid organic matter in sedimentary rocks, and is a natural organic biopolymer of irregular structure. Kerogen can range in degree of saturation where the ratio of the aliphatic to aromatic content contributes to thermal maturity designations. Kerogen is insoluble in normal organic solvents because of its high molecular weight. Upon significant heating, kerogen may convert to liquid or gaseous hydrocarbons.

Unconventional source-rock formations may typically be known for their very low permeability and very low hydraulic conductivity. The permeability may be less than 1 millidarcy. Shale rock can be generally impermeable having nanodarcy permeability. Hydrocarbon production (crude oil and/or natural gas) from unconventional source rock formations has generally become economically viable, for example, through extended-reach horizontal drilling and the creative multistage hydraulic-fracturing operation. Unconventional source rock reservoirs may differ from conventional reservoirs due to the presence of the hydrocarbon-source material (kerogen and other abundant organic matter) in unconventional reservoirs. This irregular natural polymer often represents, for example, 8% to 15% by weight (or 16% to 30% by volume) of the sedimentary source-rock formation in an unconventional formation. The rock matrix of minerals may be interwoven and compacted together with the kerogen, bitumen, and other organic components that also have nanopore size that contribute immensely to the low permeability and the overall oil and gas flow. The kerogen and the other organic matter with elastomeric properties exposed after the hydraulic fracture operation on the fracture face are clearly masking any fluid flow and contributing to the very low permeability (see, e.g., FIG. 1) and the hydraulic conductivity of the fractured faces and handicapping the overall hydraulic fracture conductivity and well productivity. FIG. 1 is a schematic of hydraulic fracture extending from wellbore, where the fracturing fluid system encounters the ductile organic matter illustrated as spider webs.

FIG. 1 is well 100 having a wellbore 102 formed in a subterranean formation 104 having organic matter 106 (organic material), such as kerogen. The wellbore 102 is depicted as a circular cross section. The subterranean formation 104 is a geological formation in the Earth's crust and may be an unconventional source-rock formation having hydrocarbon. The subterranean formation 104 may be an organic-rich shale zone. The spider-web symbol represents the presence of the organic matter 106. In FIG. 1, a fracture 108 is being formed via injection of a fracturing fluid 110 (stimulation fluid) from the Earth's surface through the wellbore 102 into the subterranean formation 104. The fracturing fluid 110 may be injected at a specified flow rate ($q_o$). The flow rate ($q_o$) may be specified as a volumetric flow rate or mass flow rate. The fracturing fluid 110 may include proppant 112, such as sand or ceramic proppant. The fracture 108 may propagate perpendicular to a minimum principal stress 114 of the formation 104 and in a direction against a maximum principal stress 116 of the formation.

The schematic in FIG. 1 depicts the hydraulic fracture 108 extending from the wellbore 102. The fracturing fluid 110 system encounters the ductile organic matter 106 illustrated as spider webs. The presence of the organic matter 106 at the fracture face 118 may restrict the generation of permeable channels from the geological formation 104 into the fracture 108. Thus, the organic matter 106 may inhibit the subsequent production of hydrocarbon from the formation 104 into and through the fracture 108 to the wellbore 102 and Earth surface. The fracture face 118 may be an interface of the forming fracture 108 with the subterranean formation 104. The polymer-like organic material 106 may be intertwined within the organic material and with the rock. The organic material 106 affects fracturing (fracture) behavior and reduces resulting hydraulic conductivity.

The interwoven structure of organic matter and mineralogy seen in the offset image of the fracture face 118, which is a scanning electron microscope (SEM) image. The SEM image illustrates an example of what a fracturing fluid encounters at the fractured faces as the fracture tip and length extends into the source-rock formation (subterranean formation 104). The highly viscous polymer nature of the organic matter augments creep effects and proppant embedment, reducing the aperture of the induced hydraulic fracture. The SEM image shows that these organic macerals of kerogen and other organic components are much less porous that of the hosting mineral matrix, and can act as barriers to fluid flow from the stimulated formation 104 into the opened hydraulic fracture 108, thus limiting the source rock permeability and formation hydraulic conductivity while reducing the overall hydraulic fracture conductivity. These laboratory observations are a direct indication of what the field will encounter, in terms of permeability reduction and potential losses of the economic returns in the overall hydraulic fracturing operation.

Figure 2:
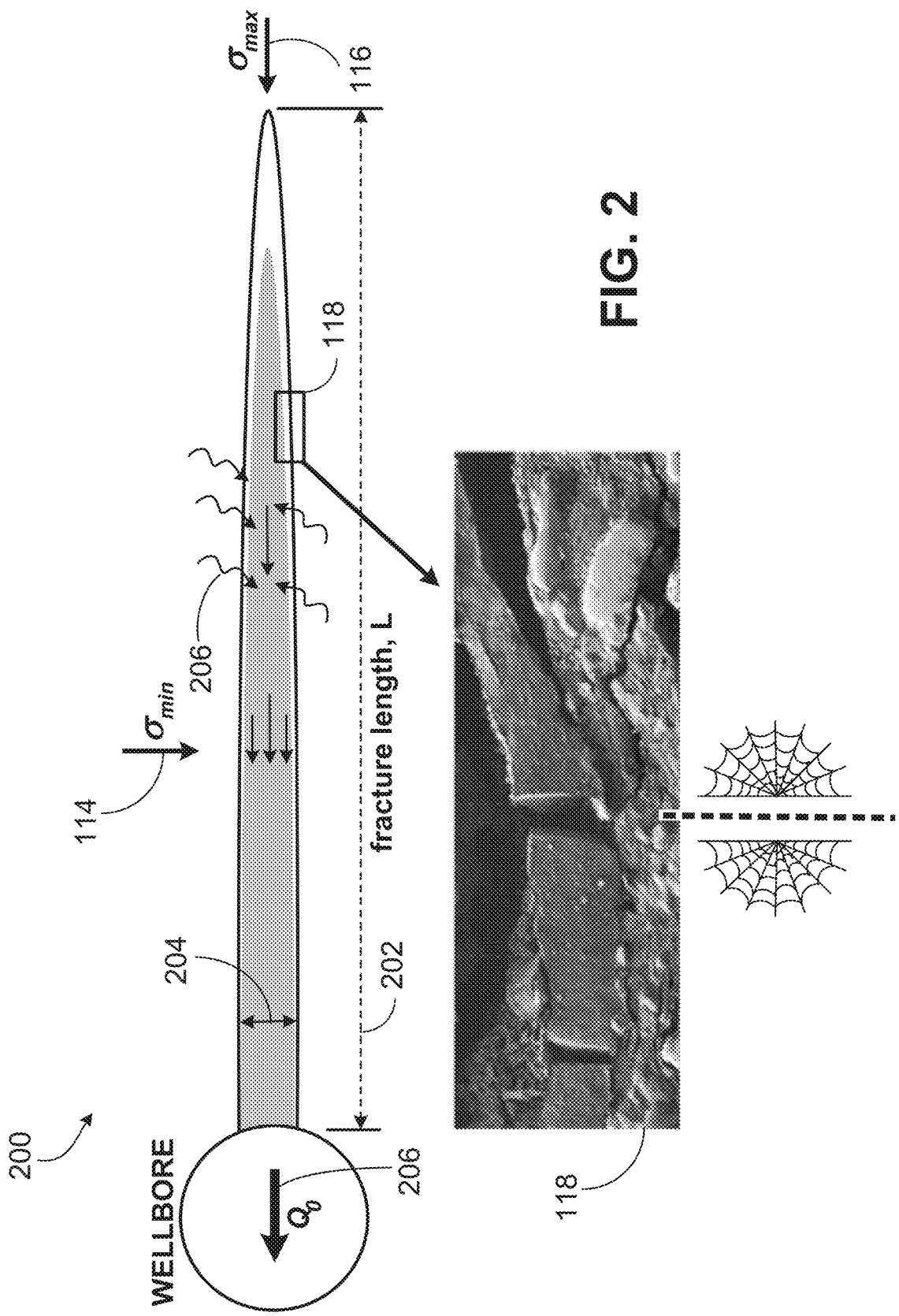
FIG. 2 a diagram of the well of FIG. 1 after a hydraulic fracture is formed and with the well in production.

FIG. 2 is a well 200 that is the well 100 of FIG. 1 after the hydraulic fracture 108 is formed and with the well 200 in production. FIG. 2 depicts the hydraulic fracture 108 extending from the wellbore 102. The fracture 108 has a length 202 and width 204. The fracturing fluid 110 (FIG. 1) that formed the fracture 108 was a fracturing fluid having an oxidizer that attacked the organic matter 106. Thus, the fracturing fluid 110 system caused organic matter 106 to crack open to generate permeable channels from the formation 104 into the fracture 108 and therefore provide for conductivity from the formation 104 through the fracture 108 to the wellbore 102. The well 200 as depicted is in production phase with produced hydrocarbon 206 flow from the geological formation 104 through the fracture 108 and wellbore 102 to the Earth surface. The flow rate of the produced hydrocarbon 206 may be labeled as $Q_0$ and may be a characterized as a volumetric flow rate or mass flow rate. Thus, FIG. 2 is a schematic of the hydraulic fracture 108 extending from wellbore 102, where the fracturing fluid 110 system caused the organic matter to crack open, creating brittle polymer with open channels and increased porosity, and thus giving increased formation 104 permeability. As indicated by FIG. 2, to address the challenges with the kerogen polymer and to improve the overall hydraulic fracturing conductivity, reactive (oxidizing) fluid additives are implemented in treatment fluid (e.g., hydraulic fracturing fluid 110) that can break down the polymeric structure, creating micro cracks in the organic matter encountered on the hydraulic fracture rock faces. In other words, kerogen and other organic matter (e.g., 16-30 volume percent of the formation 104) encountered at the fracture faces may become brittle and cracked with visible fractures (cracks) on the order of tens of microns (e.g., less than 100 microns) as noted under SEM imaging. These microfractures at the fracture faces 118, in turn, can generally lead to an increase in the porosity of the exposed formation 104 face and to enhanced permeability and fluid flow channels. This induced brittleness and cracking may reduce or minimize the potential for viscous kerogen creep and the masking of the overall matrix porosity and permeability. Again, FIG. 2 provides a schematic that shows an example of kerogen that has cracked open after exposure to the aqueous oxidizing conditions. SEM images of treated source shale samples indicate a range of effects. Whether the organic matter is rendered brittle and cracked or completely degraded (or nearly completely degraded), the hydrocarbon (e.g., gas and/or oil) stored in the source shale formation 104 may more readily find its way into the fractured width (w), thus largely increasing oil or gas production ($Q_0$ and Q-after) at the wellhead.

Again, the present techniques may be applicable to shale formations and other unconventional formations. A fracturing fluid having the aqueous oxidizer as an additive may be pressure pumped to hydraulically crack and propagate the fracture. The oxidizer in the fracturing fluid may include, for example, hydrogen peroxide, inorganic peroxide, bromate (e.g., sodium bromate), persulfate (e.g., ammonium persulfate), permanganate, chlorite, hypochlorite, chlorine dioxide, chlorate, perchlorate, iodate, periodate, perborate, or any combinations thereof. The organic matter on the fracture faces exposed to the oxidizer may become brittle and break open. The newly-formed channels in the organic matter generally increase the porosity across the surface of the exposed fracture face that, in turn, may contribute to an increase in fractured formation face permeability. The SEM image of the fracture face 118 in FIG. 2 (as compared to the SEM image of the fracture face 118 in FIG. 1 prior to treatment) illustrates the depth scale of the effects of the invasive oxidizer additive into the fracture face and the extent to which the organic matter becomes brittle and physically cracks open.

Embodiments may predict and estimate the effects on the porosity and the opened formation-face permeability that such an oxidizing fluid treatment has or will have and, ultimately, how those effects influence the success of the hydraulic fracturing operation and the fractured well productivity. For instance, in particular, embodiments may estimate and calculate the increase in porosity and the enhancement of the formation permeability associated with the treated fracture faces. To this end, embodiments may include a technique that combines a series of formation properties with the results of laboratory experiments in order to calculate the amount of porosity and particularly connected porosity that are generated by the oxidizer fluid treatment.

The in-situ temperature, and the oxidizer composition and concentration in the treatment (e.g., fracturing) fluid, may also be factors considered that affect the degree of the organic matter degradation and hence in-situ connected porosity increase and hydraulic conductivity formation enhancement. Increasing in-situ temperature and increasing oxidizer concentration generally increase the degree of the organic matter degradation and thus may increase in-situ connected porosity and hydraulic conductivity. Increasing temperature generally escalates the rate of organic matter degradation and, thus, for a given amount of time, a higher temperature may result in more degradation. The in-situ temperature may be approximately the wellbore temperature or the subterranean formation temperature at the hydraulic fracturing.

To determine or estimate increase in porosity and formation permeability enhancement associated with the treated fracture faces, the analysis may rely on images (e.g., SEM images of formation samples) and calculations. The fracture face porosity and changes in fracture face porosity may be determined through visual inspection of SEM images or other types of images. The physical-structural changes that occur to the organic matter as a result of oxidative treatment can be visually inspected by high-resolution microscope (e.g., SEM). See, for example, FIG. 11. Imaging or microscopy other than scanning electron microscopy may be employed. Example calculations and equations are discussed below.

The analysis employing images and calculations can be performed before, during, and after the oxidative fracturing treatment of the subterranean formation. The techniques (e.g., relying on images and calculations) can be performed before the oxidative fracturing treatment on the subterranean formation to predict (estimate) what will be the effects of the oxidative fracturing treatment, and also performed after the oxidative fracturing treatment of the subterranean formation to estimate the realized effects of the oxidative fracturing treatment after the treatment.

The analysis may be performed before the oxidative fracturing treatment in the field occurs to predict the effects of the oxidative fracturing treatment on the subterranean formation. Before oxidative treatment in the field, a shale sample(s) from the subterranean formation may be collected (e.g., via core sampling) and analyzed in the laboratory before and after oxidative treatment in the laboratory. Thus, effects of the oxidative treatment in the field on the subterranean formation may be predicted. Moreover, in general, the oxidative treatment may be performed in the laboratory on several representative shale samples (e.g., collected via core sampling before oxidative treatment is implemented in the field on given unconventional formations) to construct a database from which predictive capabilities are built. For example, results of analysis performed on a treated shale sample that had a particular pre-treatment kerogen maturity and kerogen weight percent (and volume percent) in the rock can be applied or correlated to other pre-treated shales of similar composition. This may facilitate that laboratory tests and analyses can be utilized as a predictive tool for an engineer designing a hydraulic fracturing job in the field. Thus, the analyses may be by analogy to predict the effects of a potential oxidative fracturing treatment. By imaging and analyzing samples collected before and after oxidative treatment in the field, conclusions regarding analogous samples from a pre-treated formation may be drawn with respect to an oxidative treatment. Analogous samples may be samples (prior to oxidative treatment) composed of similar kerogen maturity (e.g., which includes density and porosity) and total organic content.

As mentioned, the aforementioned analysis (e.g., involving images and calculations) may be performed contemporaneous with or after oxidative fracturing treatment of the subterranean formation. The imaging and calculations may be performed with respect to samples collected during or after the oxidative fracturing treatment. SEM images of the samples may be inspected to determine changes in fracture-face porosity of the hydraulic fractures due to the oxidative treatment.

In the analyses (before or after the oxidative fracturing treatment), a permeability model may be employed. Permeability models may be relations or correlations that associate permeability with porosity. Examples of such relations include the Kozeny-Carman relation, Hagen-Poiseuille capillary tube models, and so on. The Kozeny-Carman relation (or similar correlation) or a capillary tube model may be employed to capture the induced porosity in shale from images and estimate the increase in permeability that results. The induced porosity may be the increase in porosity (e.g., at the fracture face) caused by the oxidative fracturing treatment.

In the Kozeny-Carman relation, the absolute permeability of a porous granular material is related to the porosity and the grain size. As indicated by Equation (1) below, absolute permeability may be directly proportional to the square of the grain size and the cube of the porosity. The Kozeny-Carman relation may be considered or utilized in modeling the permeability enhancement observed in, for example, kerogen-rich shale. Permeability can be predicted consistently in certain implementations with varying the number and type of conduit radii. In this technique, the absolute permeability k may be related to porosity $\phi$ (e.g., connected porosity) and grain size d, as indicated by the Kozeny-Carman relation given as Equation (1):

$$k \sim d^2 \phi^3 \quad (1)$$

Figure 3:
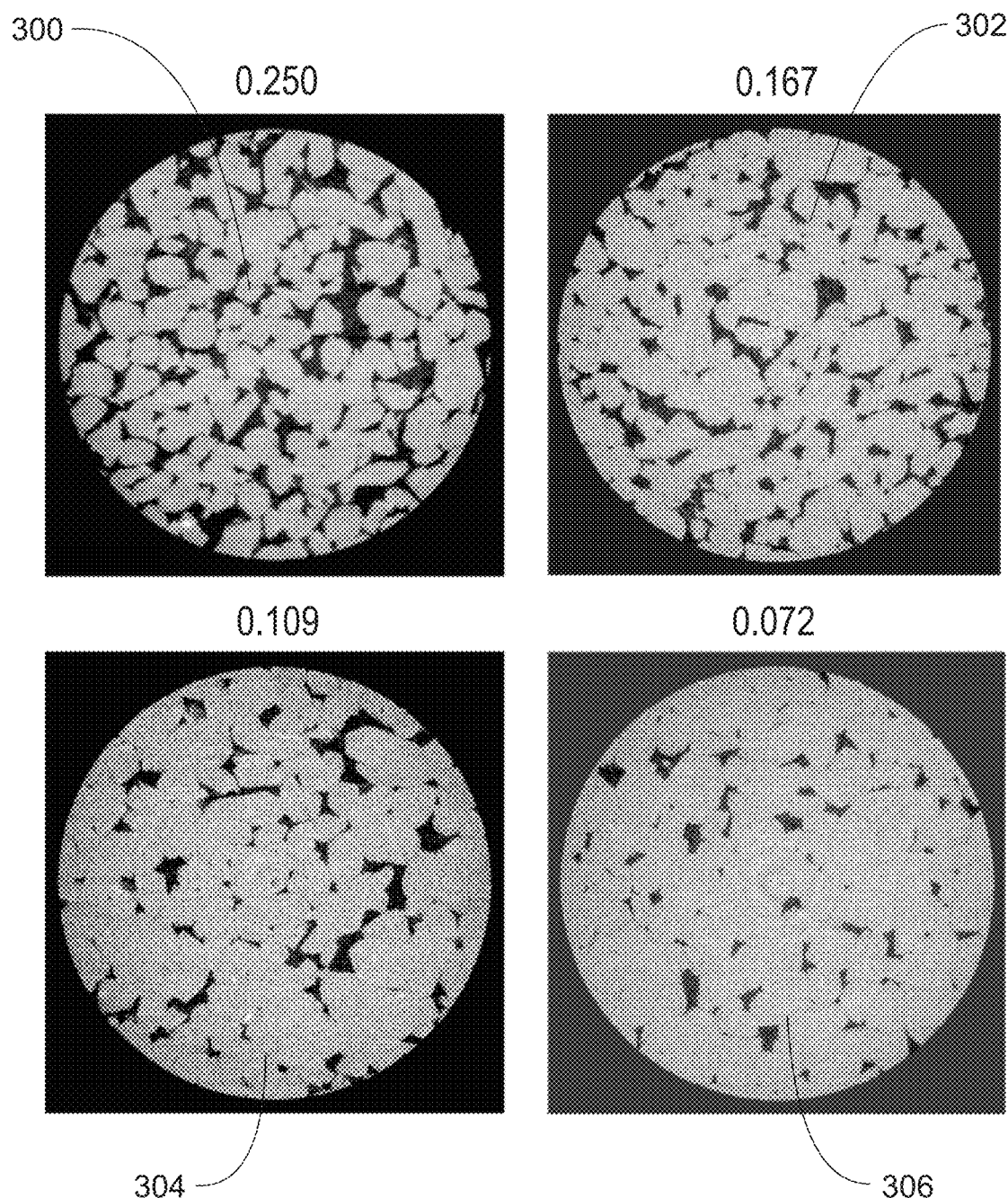
FIG. 3 is four images of Fontainebleau sandstone samples.

FIG. 3 is four images of Fontainebleau sandstone samples in which the depicted circular diameter of the imaged sample is about 2.5 millimeters (mm). The scale bar is 0.5 mm. Fontainebleau sandstone is composed generally of relatively well-sorted quartz grains. Fontainebleau sandstone may be considered a natural porous medium because of its mineral composition (e.g., 0.995 weight-percent Quartz) and generally constant grain size in relatively large sample blocks. FIG. 3 depicting the four Fontainebleau sand samples with varying respective grain size between the samples illustrates decrease in porosity according to the Kozeny-Carman approach. The four images are image 300, image 302, image 304, and image 306. A corresponding numerical value (units of mm) for grain size is given above each image for the respective sample. The Fontainebleau sandstone sample of image 300 has a grain size of 0.250 mm. The Fontainebleau sandstone sample of image 302 has a grain size of 0.167 mm. The Fontainebleau sandstone sample of image 304 has a grain size of 0.109 mm. The Fontainebleau sandstone sample of image 306 has a grain size of 0.072 mm. In accordance with the Kozeny-Carman relation, as the grain size decreases from 0.25 mm in the first image 300 to 0.072 mm in the final image 306, the porosity also decreases.

Figure 4:
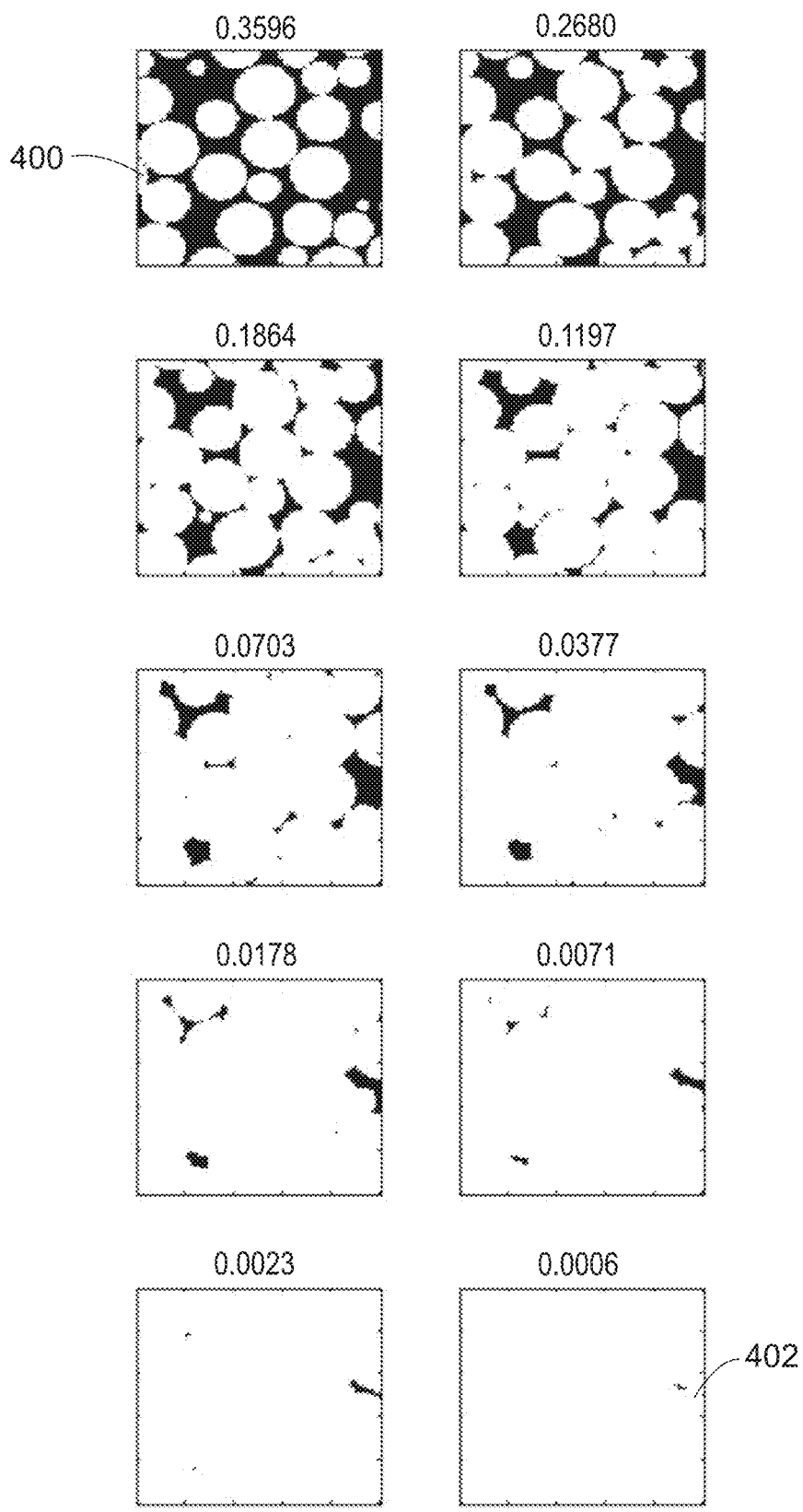
FIG. 4 is eight images of a Finney pack with decreasing porosity noted by the numerical value for porosity above each image.

FIG. 4 gives eight images of a Finney pack with decreasing porosity noted by the numerical value for porosity (unitless) above each image and with the sphere radius increasing from 1.00 mm (first image 400) to 1.45 mm (final image 402). FIG. 4 indicates an example with the Kozeny-Carman relation that demonstrates the decrease in permeability as a result of increasing grain size.

As mentioned, capillary tube models may be employed. For example, the permeability k after oxidative hydraulic fracturing treatment may be estimated utilizing a capillary tube model based on Hagen-Poisseuille's law for flow in a tube. In this model, the permeability k is related to the porosity $\phi$ (e.g., connected porosity) and the tube diameter $\delta$ as given in Equation (2) below.

$$k = \frac{\phi \delta^2}{96} \quad (2)$$

Figure 5:
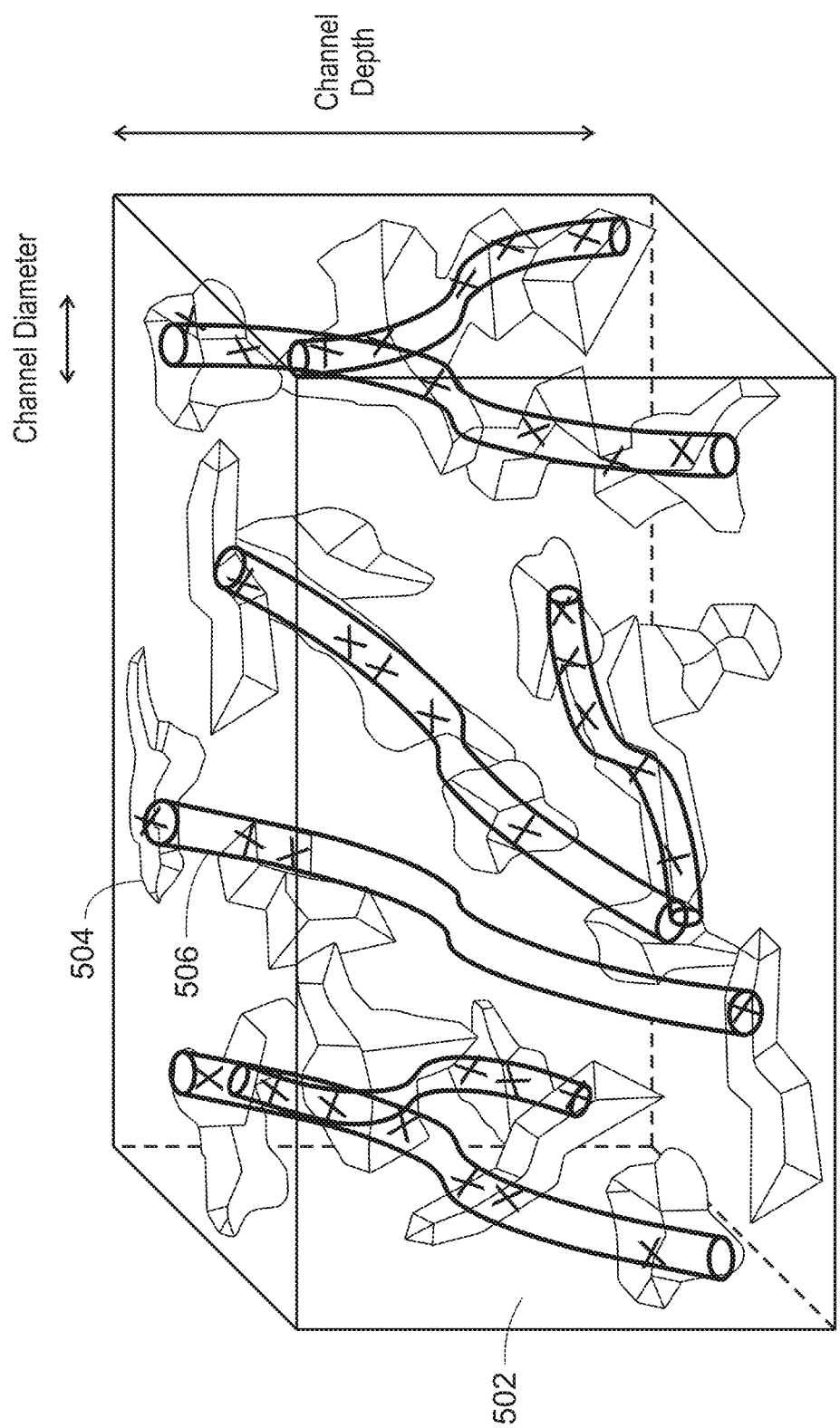
FIG. 5 is a diagram of a section of rock (e.g., shale rock) of a subterranean formation subjected to hydraulic fracturing including oxidative treatment via an oxidizer.

Applicability of this tube model expressed as Equation (2) is indicated in FIG. 5 where cracked organic matter on the fracture faces of the rock (e.g., shale) connect to or form flow channels within the rock. FIG. 5 is a schematic illustrating the flow channels that extend from the fracture faces into the depth of the rock.

FIG. 5 is a section 500 of rock 502 (e.g., shale rock) of a subterranean formation subjected to hydraulic fracturing including oxidative treatment via an oxidizer. The subterranean formation may be a shale formation having organic matter such as kerogen. The depicted section 502 extends into the formation from a hydraulic fracture having fracture faces 504. At the fracture faces 504, organic matter cracked or broke open due to the oxidative degradation may form flow channels 506 into the rock 502 into the depth of the subterranean formation. Each 'X' may represent a crack in the organic matter. The depth of these flow channels 506 may be related to the concentration of the oxidizer in the hydraulic fracturing fluid in the hydraulic fracturing treatment. The tubes or channels may extend through layers of kerogen macerals. Again, utilizing this Equation (2) model, the permeability k is related to the porosity $\phi$ and diameter $\delta$ of the flow tubes.

Given the pre-treatment permeability input $k_0$ and the pre-treatment connected porosity $\phi_0$, the average tube diameter $\delta_0$ before treatment can be estimated using Equation (3) below.

$$\delta_0 = \sqrt{\frac{96k}{\phi}} \quad (3)$$

After oxidative hydraulic fracturing, the average diameter of the tubes in fractured kerogen increases to $\overline{\delta}_k$. The $\overline{\delta}_k$ can be estimated by taking the average of the width and depth of the fractures created by oxidative treatment (oxidative hydraulic fracturing). These may be input parameters, as discussed below. For an assumption that the average diameter of the tubes in other portions of the rock after treatment remains as $\delta_0$, the average diameter of all tubes after treatment can be calculated as in Equation (4), where $v_k$ is kerogen volume fraction which is an input parameter.

$$\overline{\delta} = v_k \overline{\delta}_k + (1 - v_k) \delta_0 \quad (4)$$

The average connected porosity of the whole rock after oxidative treatment (oxidative hydraulic fracturing) given as $\overline{\phi}$ may be calculated. The estimated permeability after treatment, according to Equation (2) above may be given by Equation (5) below. The permeability enhancement factor may be $\bar{k}/k_0$, which is the ratio of the permeability after treatment to the permeability before treatment.

$$\bar{k} = \frac{\overline{\phi \delta}^2}{96} \qquad (5)$$

The effects of an oxidizing fracturing fluid on an unconventional rock formation may be determined. For instance, the changes in fracture face porosity may be determined through visual inspection of SEM images and estimating the resulting changes in fracture-face permeability. Some input parameters for these types of calculations may be determined from field logs while other input parameters may be determined by performing laboratory tests. Multiple input parameters may be combined to estimate the positive changes in porosity and permeability that may occur in an unconventional formation (e.g., unconventional shale formation) subjected to oxidative hydraulic fracturing. The fracturing fluid has an oxidizer to attack organic matter in the unconventional shale formation including at fracture faces.

FIG. 6 is an example list of input parameters that may be utilized to calculate and determine effects (e.g., permeability enhancement) of an oxidizing fracturing fluid on an unconventional rock formation. The organic matter in the formation including at fracture faces includes kerogen. In the illustrated embodiment, the example input parameters are listed in a dialog box that may be a user interface of a computing device to receive or calculate values of the input parameters. The input parameters may be calculated or determined and input before, during, or after the oxidative fracturing treatment of the formation. The numerical values given for the input parameters listed in the dialog box are not limiting and only given as examples. The calculations can be for water-based hydraulic fracturing fluids with the oxidizer aqueous additive. No leakoff into the formation may be assumed in implementations.

Kerogen parameters 600 as input parameters may include kerogen density of kerogen in the subterranean formation, kerogen weight percent (wt %) of the rock in the subterranean formation, and kerogen volume percent (vol %) of the rock in the subterranean formation. The kerogen density may be, for example, in kilograms per cubic meter (kg/m3). The kerogen density may be estimated based upon its maturity. The kerogen vol % may be determined by combining wt % with density. The kerogen vol % can be determined correlative with kerogen wt % with kerogen density. The vol % of kerogen relative to the entire shale matrix may be determined by joining wt % with the density. With the mass and dimensions of the kerogen-containing rock sample as known, then the wt % of kerogen can be converted to a mass: kerogen wt %×mass of kerogen-rich rock=mass of kerogen. Then, the mass is converted to vol % using the density: mass of kerogen/density of kerogen=volume of kerogen. The kerogen vol % may be the volume of kerogen/volume of kerogen-rich rock× 100%=kerogen vol %.

The kerogen parameters 602 may be determined, for example, via standard lab methodology utilizing a crushed rock sample. Rock-Eval® pyrolysis may be employed to determine kerogen wt % and maturity. Rock-Eval® pyrolysis (or similar pyrolysis testing analysis) may be performed to determine the percent weight of organic matter (delineate the amount of each organic matter component) and the overall maturity of the rock sample. Rock samples may be cut and milled, for instance, with a Retsch™ Mixer Mill MM400 to obtain a powder. The powder, e.g., about 60 milligrams (mg), may be subjected to a programmed temperature where the organic matter thermally decomposes over time and the resulting by-products of this decomposition are measured via a flame ionization detector. During the pyrolysis analysis a maximum temperature (Tmax) of complete combustion is reached and a pyrogram is produced that records the hydrocarbon generative potential of the kerogen, both of which can be used to define the maturity. Elemental analysis can also be performed on kerogen samples to determine concentrations of hydrogen, carbon, oxygen, nitrogen and sulfur. Because kerogen loses more hydrogen than carbon as kerogen is transformed into hydrocarbons, monitoring the changes in hydrogen relative to the carbon may be considered an indication of maturity. See Example 1 in the Examples section below in which Rock-Eval® pyrolysis was performed on about 60 mg of an unconventional rock sample.

Once the maturity is determined, the density may be obtained via empirical relationships. For examples of such empirical relationships, see Okiongbo, K. S.; Aplin, A. C.; Larter, S. R., Changes in Type II Kerogen Density as a Function of Maturity: Evidence from the Kimmeridge Clay Formation, Energy & Fuels 2005 19 (6), 2495-2499. The density may be correlated to maturity through the hydrogen index (e.g., FIG. 7) or through Tmax (e.g., FIG. 8).

Figure 7:
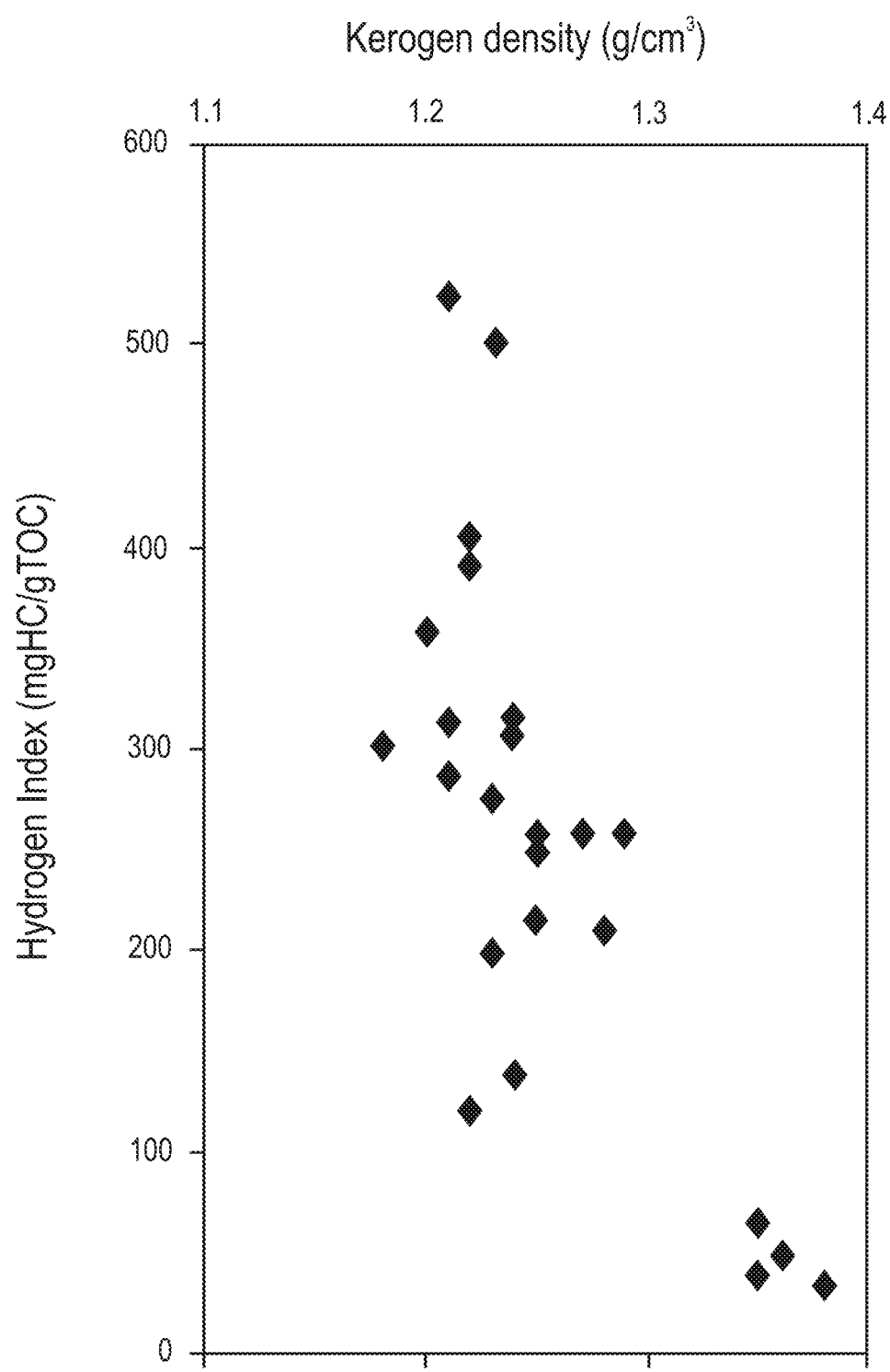
FIG. 7 is a plot of an example empirical relation of kerogen density with hydrogen index.
Figure 8:
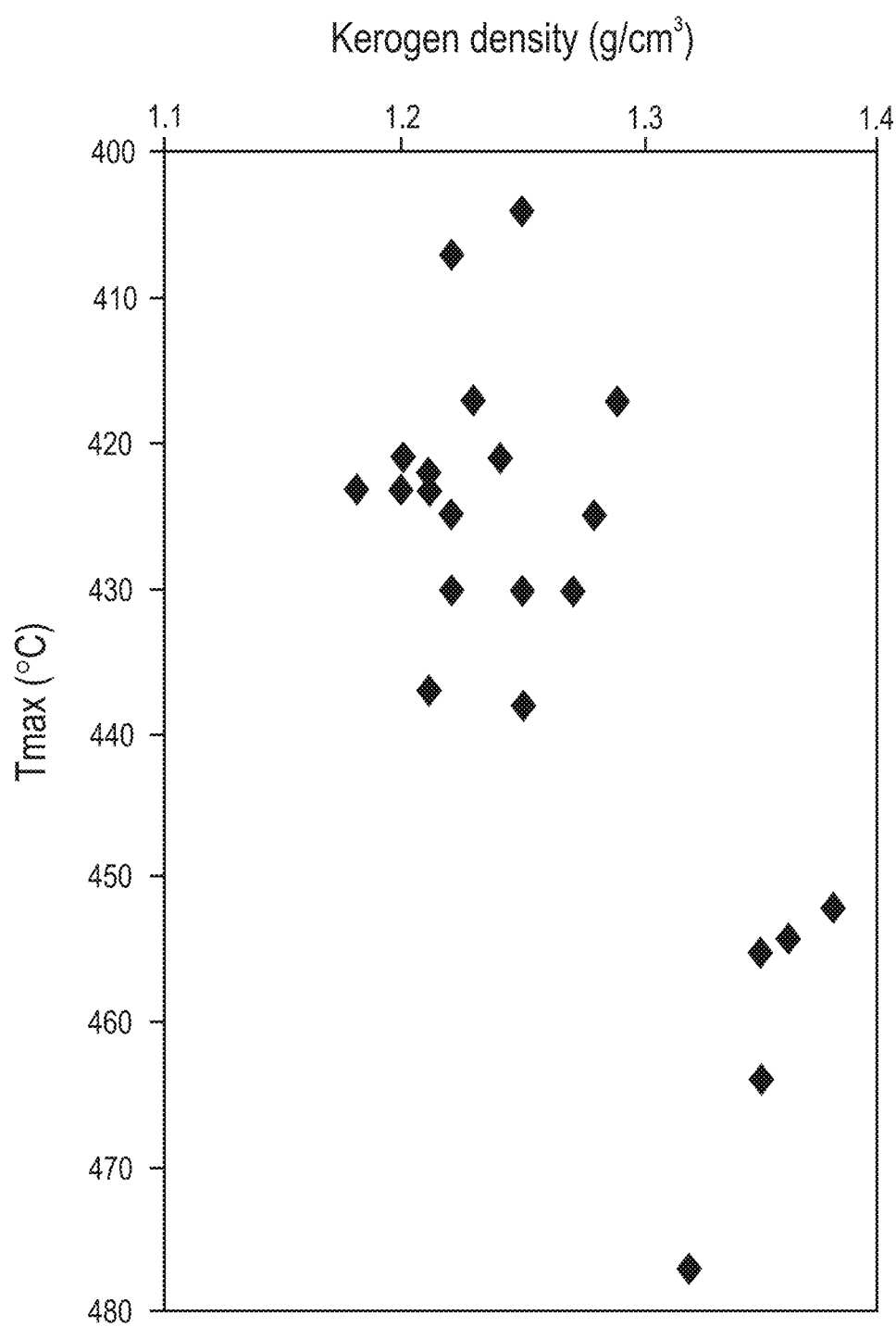
FIG. 8 is a plot of an example empirical relation of kerogen density with Tmax (° C.).

FIG. 7 is a plot of an example empirical relation of kerogen density (grams per cubic centimeter or g/cm3) with hydrogen index having units of milligrams hydrocarbon per grams of total organic content (mgHC/g TOC). The data points of kerogen density versus hydrogen index are depicted at triangles on the plot. FIG. 8 is a plot of an example empirical relation of kerogen density (g/cm3) with Tmax (° C.). The data points of kerogen density versus Tmax are depicted at triangles on the plot. Hydrogen index (HI) and Tmax (maximum temperature) are determined by Rock-Eval® pyrolysis where peaks S1, S2, S3, and S4 are obtained and quantified. The equation HI=S2 (mg/g)/% TOC×100 is applicable. Tmax is determined directly from Rock-Eval® pyrolysis, where the maximum temperature is obtained upon complete combustion of the sample.

Fracture dimension parameters 604 as input parameters may include fracture length and fracture height that may be input, for example, in meters (m). The values for fracture length and fracture height may be estimated, for example, based on fracture-dimension data from similar wells in the same reservoir field of the subterranean formation. The values for fracture length and fracture height may be estimated from hydraulic fracturing simulation software, such as Gohfer® software (available from Halliburton Corporation having headquarters in Houston, Tex., USA), FracPro software (available from Carbo Ceramics, Inc. having headquarters in Houston, Tex., USA), etc. The length, width, and height of fractures may be estimated on the basis of the volume of hydraulic fracturing fluid and proppant pumped, as well as assuming there is no leakoff into the formation in implementations.

The porosity input parameters 606 as input parameters may include total porosity and percent (%) connected porosity. The total porosity and % connected porosity as input parameters 606 may be variables before hydraulic fracturing. The rock porosity can be determined, for example, either from well log measurements or by laboratory methods. The values will generally vary from one rock formation to the next. Again, values for the porosity input parameters 606 may be obtained, for instance, from well logs or from analysis of collected formation samples via standard laboratory methodologies. Moreover, as total porosity is a ratio or dimensionless, the units may be porosity units (PU) or %. The % connected porosity is the percent of the total porosity that is connected porosity. Analyses to obtain porosity values of samples may include mercury intrusion porosimetry, gas injection prorosimetry, and high-resolution imaging and digital image processing. The porosity of the formation may be determined from a nuclear magnetic resonance (NMR) log taken of the well. NMR logging measures the hydrogen nuclei of the fluids (oil, gas, water) in the pore space of reservoir rocks. The log provides information about the sizes of the pores containing these fluids such that the volume (porosity) and distribution (permeability) of the rock pore space can be determined. Alternatively, there are standard laboratory techniques for determining porosity and connected porosity including mercury intrusion porosimetry, gas injection porosimetry, and high resolution imaging in conjunction with digital image processing.

An additive/kerogen ratio 608 may be an input parameter 600. The additive may be the oxidizer in the fracturing fluid. The additive/kerogen ratio 608 may be a mass or weight ratio, for example, in kilogram (kg) per kg. The "additive/kerogen ratio" or "oxidizer/kerogen ratio" may be the mass of oxidizer per the mass of kerogen degraded or decomposed by the oxidizer. The additive/kerogen ratio may be the mass of additive in the fracturing fluid divided by the mass of kerogen that the fracturing fluid contacts or decomposes.

The additive (oxidizer)/kerogen ratio may be obtained from or determined by laboratory methods, e.g., at respective temperatures. For instance, rock samples may be cut and milled, for example, with a Retsch™ Mixer Mill MM400 to obtain a powder. In this implementation, the soluble bitumen from the rock powders may then then extracted using dichloromethane and the remaining rock matrix composed of silicates, aluminosilicates and carbonates was then digested using a combination of hydrochloric acid (HCl) and hydrofluoric acid (HF) to isolate and recover the remaining insoluble kerogen. The recovered kerogen may then be segregated into a float (e.g., <1.8 g/cc) versus sink (e.g., >1.8 g/cc) fraction employing a density liquid separation technique utilizing, for instance, zinc bromide. This segregation may facilitate for the use of kerogen containing less pyrite (float) versus kerogen with higher amounts of pyrite (sink) to test the sensitivity of the kerogen to the oxidizing fluids. In a particular implementation, oxidizer (e.g., 0.26 M oxidizer) is dissolved in water (e.g., 25 mL of water) in a pressure tube (e.g., 120 mL glass pressure tube). Isolated kerogen (e.g., 0.10 g of isolated kerogen) is added to the solution, and the pressure tube is sealed. The mixture is heated to (e.g., 100-150° C.) (determined by the bottom hole static temperature of the well of interest) in an oil bath (e.g., for 20 hours), then cooled to room temperature. The solid residue is filtered, rinsed several times, dried in an oven (e.g., at 60° C.), and massed. The oxidizer mass is divided by the decomposed kerogen mass (0.1 g—residue mass) to determine the additive/kerogen mass ratio. See Example 2 in the Examples section below giving an example of determining an additive/kerogen mass ratio. Again, the "additive" may generally refer to the "oxidizer" employed in the hydraulic fracturing fluid.

The treated fracture-faces parameters 610 may include fracture face depth affected and fractured kerogen porosity. Laboratory methods at respective temperatures may be utilized to determine the parameters 610. For instance, a laboratory technique may include to cut and polish a shale sample, heat the sample in fluid with additive (oxidizer), remove sample from fluid and dry sample, perform high-resolution imaging on dried sample, and determine depth of fracture face affected and the increase in porosity. Rock specimens may be cut from the same core from which the kerogen and bitumen samples were recovered. Each sample may be polished to expose parallel bedding planes of the shale to facilitate that the tests made on isolated kerogen could be compared to tests made on kerogen in the rock. See Example 3 in the Examples section below.

In certain implementations, an assumption may be that there is no hydraulic-fracturing fluid leakoff that occurs in the formation. Values for the aforementioned input parameters listed in FIG. 6 may be, for example: kerogen density (1.18-1.25 g/cm3 during early phase of petroleum generation and increases to at least 1.35 g/cm3 at higher maturities), kerogen wt % (2-20 wt % and 6-12 wt %), kerogen vol % (4-40 vol % and 12-24 vol %), fracture face depth affected (μm to mm for water-based fracturing), fracture length (100 to 400 m), fracture height (10 to 50 m), formation or fracturing temperature (80-150° C.), and additive/kerogen ratio (1 to 1000 wt/wt). These example value ranges of input values may be based on our knowledge of kerogen-rich source rock formations where hydraulic fracturing is performed. For example, in order for the formation to be sufficiently hydrocarbon rich to warrant hydraulic fracturing, the kerogen levels may generally be at least 2% but more likely at least 6%. Some input values (e.g., kerogen weight % and total porosity) may be based on well logs or standard laboratory tests. As discussed, fracture length and height may be obtained from standard hydraulic fracturing modeling software. Expected input values (e.g., for fracture face depth affected, fractured kerogen porosity, and additive/kerogen ratio) may arise from specific laboratory results based on the workflow in embodiments of the present techniques. The temperature of the experiments may be dictated by the bottom hole static temperature of the well or other temperatures or factors.

FIG. 9 is a user-interface (e.g., input pane) for dataset retrieval. The techniques may provide for sets of input parameter values to be stored in a database for later retrieval. A database look-up can be performed by specifying the field name, well identifier, in-situ formation temperature, and kerogen maturity, as indicated in FIG. 9. In some implementations, pull-down menus may facility such specifying. Then, as the corresponding dataset is retrieved from the database, the stored input parameter values may be populated (e.g., automatically populated) in the input pane of the user interface. The input pane of FIG. 9 or similar interface as an implementation may provide for database look-up of stored input parameter values.

FIG. 10 is a user-interface (e.g., output pane) for presenting treatment effects as calculated or determined, such as based on the aforementioned input parameters. In implementations, these treatment effects affected by the additive/kerogen ratio. The additive/kerogen ratio can be relevant for determining treatment quantities to be implemented in the field. Again, in implementations, the additive/kerogen ratio is not directly utilized to calculate the treatment effects but instead to determine the treatment quantity.

After values of the input parameters are established and input (e.g., in FIG. 6), then calculations may be performed to determine the volume of porosity and % volume of porosity created by the oxidizer fluid additive treatment. The example specific values displayed in FIG. 10 are the output values associated with the input values shown in FIG. 6 for the input parameters. These treatment effects in FIG. 10 may include porosity-created variables 1000 and connected porosity-created variables 1002. In general, most or all treatment effects characterized may be outputs. The permeability increase or permeability enhancement may an output variable.

The porosity-created variables 1000 may include treatment effects of both bulk formation volume affected (e.g., cubic meters or m3) and void space created (e.g., m3). The porosity created may be calculated correlative with the bulk formation volume affected. Porosity created is the same as void space created. The bulk formation volume affected is the amount of the formation that was affected by the treatment. This is determined by multiplying the fracture length by the fracture height (surface area) times the "fracture face depth affected" times 2 (for the 2 fracture faces). The void space created may be determined by multiplying the "treated kerogen porosity" by the kerogen vol % times the bulk formation volume affected. The treated formation volume may be equal to the mathematical product of the fracture length·fracture height·fracture face depth·2. The "treated formation volume" is the same as "bulk formation volume affected."

The connected porosity-created variables 1002 may include connected porosity before oxidative hydraulic fracturing (of the subterranean formation) and connected porosity after oxidative hydraulic fracturing. Again, oxidative hydraulic fracturing may be hydraulic fracturing of the subterranean formation with a fracturing fluid having an oxidizer. The connected porosity before oxidative hydraulic fracturing is not a treatment effect but is before treatment. The connected porosity before oxidative hydraulic fracturing may be equal to the mathematical product of % connected porosity (before oxidative hydraulic fracturing) multiplied by total porosity (before oxidative hydraulic fracturing). The connected porosity after oxidative hydraulic fracturing is a treatment effect and may be equal to the sum of the connected porosity before oxidative hydraulic fracturing plus the mathematical product of the fractured kerogen porosity multiplied by kerogen volume percent (vol %). Thus, the increase in connected porosity may be the fractured kerogen porosity multiplied by the kerogen vol % (in the rock). See Example 3 below in the Examples section, which is an example of evaluating treated fracture faces.

As discussed above, Rock-Eval® pyrolysis may be performed to interpret thermal maturity or other properties. Rock-Eval® pyrolysis was developed by Institut Français du Pétrole (IFP) (French Institute of Petroleum) based at Rueil-Malmaison, France. In such a pyrolysis analysis, a rock sample undergoes increasing temperature in an inert atmosphere where three peaks of released hydrocarbons can be measured. The first peak (S1) represents the volatilization of any previously generated hydrocarbons present in the rock, given that the rock has reached thermal maturity. The second peak (S2) indicates the thermal degradation of any remaining organic material into hydrocarbons. The final peak (S3) is any organic CO2 present in the rock. The temperature at which the S2 peak occurs may be an approximation of the thermal maturity of the rock. In addition to thermal maturation, pyrolysis peaks S1, S2, and S3 yield information about the type of organic material present in the rock. During the pyrolysis analysis, a maximum temperature (Tmax) of complete combustion may be reached and a pyrogram produced that records the hydrocarbon generative potential of the kerogen, both of which can be utilized to define the maturity.

Thus, the Rock-Eval® pyrolysis may be performed to interpret thermal maturity or other properties. Rock-Eval® pyrolysis as a pyrolysis technique may be pyrolysis that is the decomposition of organic matter by heating in the absence of oxygen. The pyrolysis may be employed to measure richness and maturity of potential source rocks. In a pyrolysis analysis, the organic content may be pyrolyzed in the absence of oxygen, then combusted. The amount of hydrocarbons and carbon dioxide released may be measured. In Rock-Eval® pyrolysis, a sample may be placed in a vessel and progressively heated (for example, to 550° C.) under an inert atmosphere. During the analysis, the hydrocarbons already present in the sample are volatized and the amount of these hydrocarbons measured and recorded as a peak known as S1. Next, the amount of hydrocarbons generated by pyrolysis of kerogen in the sample is recorded as an S2 peak. The amount of CO2 generated is recorded as the S3 peak. The amount of residual carbon is measured and recorded as S4. The percent total organic carbon (TOC) may be related to the S peaks.

Various water-based (aqueous) oxidative fracturing fluids may be employed. An oxidative fracturing fluid for hydraulic fracturing of subterranean formation is a fracturing fluid having an additive that is an oxidizer. Concentration of the oxidizer (e.g., less than 4 M) in that the oxidative fracturing fluid (e.g., an aqueous composition) may be specified based at least in part on an amount of organic matter or kerogen to degrade in the subterranean formation. The oxidative fracturing fluid having the oxidizer may be placed (pumped) through a wellbore into the subterranean formation to hydraulically fracture the subterranean formation and degrade the kerogen. The oxidizer in the fracturing fluid may include one or more oxidizers. The oxidizer may include hydrogen peroxide, an inorganic peroxide, a bromate, a persulfate, a permanganate, a hypochlorite, a chlorite, chlorine dioxide, a chlorate, an iodate, a perchlorate, a periodate, or a perborate, or any combinations thereof. The concentration of the oxidizer in the fracturing fluid may be less than 4 M, less than 2 M, or less than 1 M. The oxidative fracturing fluid may include produced water, flowback water, brackish water, Arab-D-brine, or seawater, or any combinations thereof. The oxidative fracturing fluid may include salt at less than 20 weight percent (wt %) in the aqueous composition. The salt may include, for example, potassium chloride, sodium chloride, lithium chloride, potassium bromide, sodium bromide, lithium bromide, ammonium chloride, ammonium bromide, ammonium iodide, calcium chloride, magnesium chloride, strontium chloride, calcium bromide, magnesium bromide, strontium bromide, calcium iodide, magnesium iodide, or strontium iodide, or any combinations thereof. The oxidative fracturing fluid for hydraulic fracturing may include an imidazolium, an imidazole, an ammonia, a pyrrolidinium, a pyrrolidine, pyridinium, a pyridine, a phosphonium, chloride, bromide, iodide, tetrafluoroborate, hexafluorophosphate, sulfonate, or proppant, or any combinations thereof. Other components are applicable. Other oxidative fracturing fluids may be employed. Discussion of hydraulic fracturing fluids having an oxidizer(s) for treating (degrading) organic matter or kerogen in the hydraulic fracturing of a subterranean formation may be found, for example, in U.S. Pat. No. 10,351,758, which is incorporated by reference herein in its entirety.

EXAMPLES

The Examples are not intended to limit the present techniques and are given only as examples. Example 1, Example 2, and Example 3 are presented.

Example 1

Example 1 is associated with the kerogen parameters 600 discussed above with respect to FIG. 6. Table 1 below gives results of Example 1 in which Rock-Eval® pyrolysis was performed on about 60 mg of an unconventional rock sample containing type II-S kerogen. The results of the test are shown in Table 1. The maturity was determined to be late oil based on the Tmax value and the hydrocarbon generative potential. The properties in Table 1 include are S1 (milligram per gram or mg/g), S2 (mg/g), S3 in (mg/g), (productivity index), Tmax (° C.), HI (hydrogen index), OI (oxygen index), and H/C (hydrogen to carbon ratio), and maturity. S1, S2, and S3 are pyrolysis peaks. S1 is free hydrocarbons present in the sample before the analysis. S2 is the amount of hydrocarbons that formed during thermal pyrolysis of the sample (utilized to estimate the remaining hydrocarbon-generating potential of the sample). S3 is the CO2 yield during thermal breakdown of kerogen.

TABLE 1

Rock Eval pyrolysis parameters determined for a source rock sample

| S1 (mg/g) | S2 (mg/g) | S3 (mg/g) | PI | Tmax (° C.) | TOC (wt %) | HI | OI | H/C | Maturity |
|---|---|---|---|---|---|---|---|---|---|
| 0.74 | 5.92 | 0.51 | 0.11 | 465 | 10.93 | 54 | 10 | 0.612 | Late |

Example 2

Example 2 is associated with the additive/kerogen ratio 608 discussed above with respect to FIG. 6. Example 2 is an example of determining the additive (oxidizer)/kerogen weight (mass) ratio. In Example 2, 1.0 g NaBrO$_3$ was dissolved in 25 mL of water in a 120 mL glass pressure tube. Then, 0.10 g of isolated type II-S kerogen with late oil maturity was added to the solution, and the pressure tube was sealed. The mixture was heated to 150° C. in an oil bath for 20 hours, then cooled to room temperature. The solid residue was filtered, rinsed several times, dried in an oven at 60° C., and massed. The oxidizer mass is divided by the decomposed kerogen mass (0.1 g-0.0797 g) to determine the additive/kerogen mass ratio of 49 in Example 2.

Example 3

Example 3 is associated with the fracture-faces parameters 610 discussed above with respect to FIG. 6 and treatment effects discussed with respect to FIG. 10. Example 3 is an example of evaluating fracture faces treated with an oxidizer. In Example 3, shale rock specimens were cut from the same core from which the kerogen and bitumen samples were recovered. Each sample was polished to expose parallel bedding planes of the shale to facilitate that the tests made on isolated kerogen could be compared to tests made on kerogen in the rock. These source shale samples were mechanically polished with the Allied High Tech Multi-Prep™ system (available from Allied high Tech Products Inc. having headquarters in Compton, Calif., USA) first using 600 and 1200 grit silicon carbide paper, and then with progressively finer diamond suspensions beginning at 3 microns (μm) and continuing until reaching 0.05 μm. The small polished source shale samples (<10 mm in each dimension) were imaged via SEM (e.g., SEM image 1100 in FIG. 11)). Specific organic matter features were identified, and then SEM images were obtained. Each sample and image were then analyzed with energy-dispersive x-ray spectroscopy (EDS) to confirm the carbon nature of the features. The sample was then unmounted and added to the treatment fluid containing 0.0087 molar (M) ammonium persulfate, 0.013 M sodium bromate, and 0.27 M potassium chloride in 10 mL of water for 20 hours at 100° C. The fluid was then cooled, and then the sample removed from the fluid and dried in an oven at 80° C. After drying, SEM imaging (e.g., SEM image 1102 in FIG. 11) was again performed, and the location of the previous organic matter features were identified and reimaged via SEM and EDS. The fractured kerogen porosity was estimated by identifying the new pores and new fractures (e.g., microfractures) generated in the kerogen by the treatment process. The fracture face depth affected was also estimated from the electron microscope images.

Figure 11:
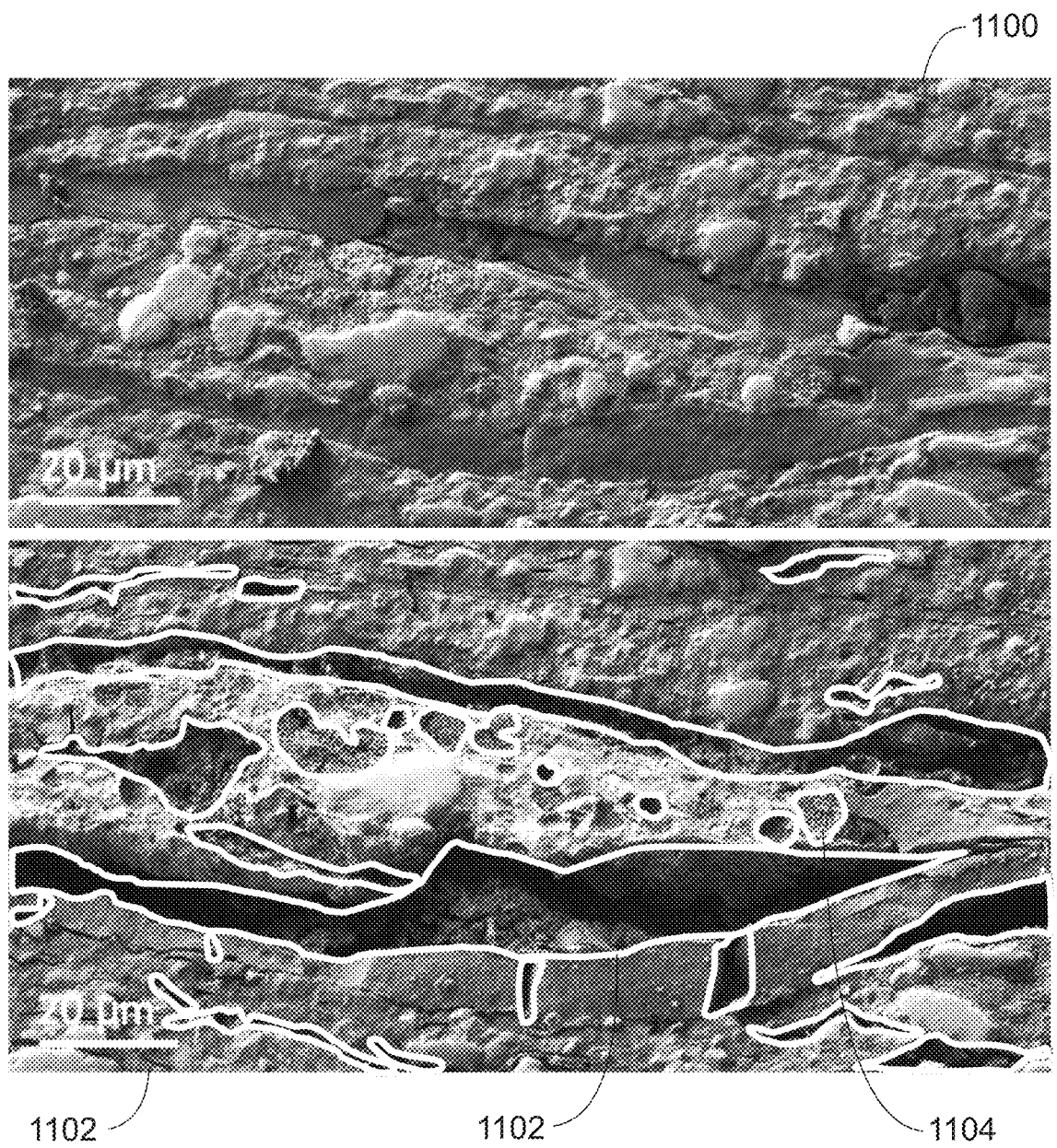
FIG. 11 are two images of the same shale sample, and associated with Example 3.

FIG. 11 are SEM image 1100 and SEM image 1102, each of the same shale sample pre-oxidative treatment and post-oxidative treatment, respectively, and associated with Example 3. The SEM image 1100 is an SEM image of a shale sample that has not been treated with an oxidizer. The SEM image 1102 is an SEM image of that shale sample after being treated with an oxidizer. Thus, with respect to oxidative treatment, image 1100 is a before image and image 1102 is an after image. As discussed in Example 3, the shale sample was treated with an aqueous treatment fluid (solution) having two oxidizers 0.0087 M ammonium persulfate and 0.013 M sodium bromate, as well as the salt 0.27 M potassium chloride, for 20 hours at 100° C. Items 1104 in the shale sample in the SEM image 1102 (the after image) are new items that increase total porosity of the shale sample. These new items (items 1104) were caused by the shale sample being subjected to a treatment fluid having oxidizer. The items 1104 are artifacts caused by the oxidative treatment and that contribute to total porosity. In other words, the items 1104 are new pores (new microfractures) formed in and around the organic matter (kerogen) and that increase total porosity of the shale sample.

Figure 12:
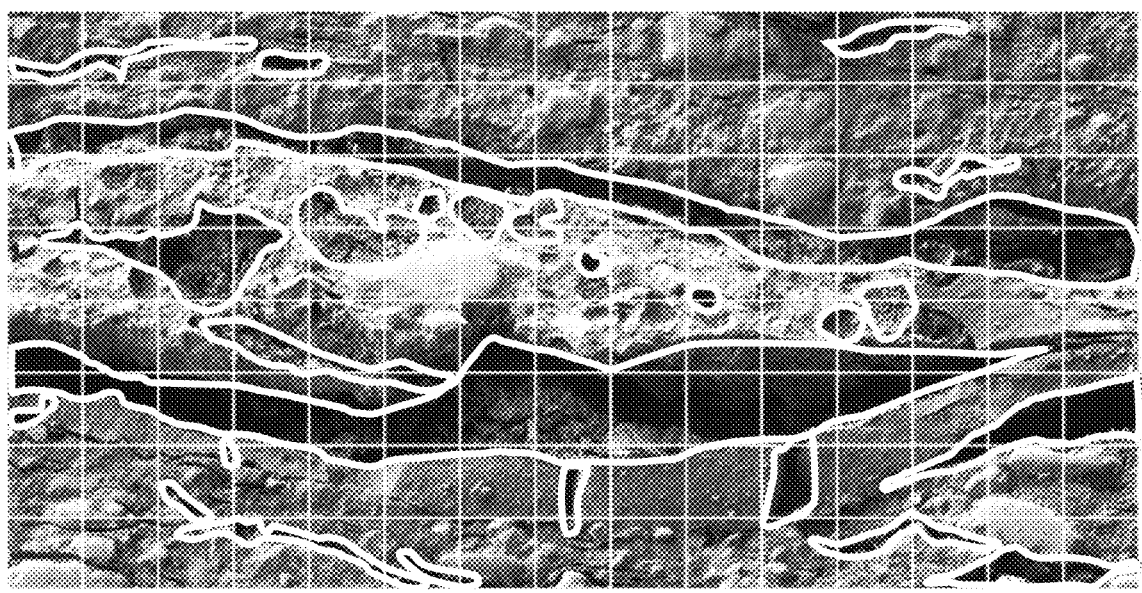
FIG. 12 is an image of the shale sample of FIG. 11 but with a grid placed over the image.

FIG. 12 is an image 1200 that is the SEM image 1102 of FIG. 11 but with a grid placed over the SEM shale image. To give the image 1200, a grid pattern is drawn over the surface of the SEM shale image 1102. In this illustrated example, the grid is 8 rows by 15 columns. Thus, there are 15 blocks (squares) in each of the 8 rows, and there are 8 blocks (squares) in each of the 15 columns. The grid is placed over the SEM shale image to estimate the surface area covered by the new items 1104 (new pore features) that increase total porosity of shale sample.

In this example, a scale of numbers 0, 1, 2, or 3 for each square of the grid represents an estimate of area coverage of items 1104 within the given square, where 0=0%, 1=33%, 2=67%, and 3=100%. As tabulated below in Table 2, these numbers of 0, 1, 2, or 3 from the scale that are assigned for each square are summed to estimate the added total porosity of 34% to the shale sample due to the oxidative treatment. Knowing this 34% facilitates determine permeability enhancement or increase in connected porosity. This 34% would be utilized as the treated kerogen porosity (0.34) and would be utilized to determine the void space created.

Computer digital-image processing may be employed in determining coverage (and thus added total porosity) of the items 1104 (new pores/microfractures) in and around the organic matter (kerogen) of the shale sample as imaged at the surface (face) of the shale sample.

multiplied by total porosity (before oxidative hydraulic fracturing). This connected porosity or percent connected porosity may be compared to the connected porosity or

TABLE 2

Assigned numerical scale values for each square of 8 × 15 grid

|   | 1 | 2 | 3 | 4 | 5 | 6 | 7 | 8 | 9 | 10 | 11 | 12 | 13 | 14 | 15 | T |
|---|---|---|---|---|---|---|---|---|---|----|----|----|----|----|----|---|
| 1 | 1 | 1 | 1 | 1 | 1 | 0 | 0 | 0 | 0 | 0  | 0  | 2  | 1  | 0  | 0  | 8 |
| 2 | 2 | 2 | 2 | 1 | 1 | 1 | 0 | 0 | 0 | 0  | 0  | 0  | 0  | 0  | 0  | 9 |
| 3 | 1 | 0 | 1 | 1 | 1 | 2 | 3 | 2 | 2 | 1  | 0  | 0  | 2  | 1  | 1  | 18 |
| 4 | 1 | 1 | 3 | 1 | 2 | 1 | 1 | 1 | 0 | 1  | 1  | 2  | 2  | 2  | 3  | 22 |
| 5 | 1 | 0 | 1 | 1 | 1 | 0 | 1 | 1 | 1 | 1  | 2  | 3  | 1  | 1  | 0  | 15 |
| 6 | 1 | 1 | 2 | 2 | 2 | 3 | 3 | 3 | 3 | 3  | 3  | 2  | 1  | 2  | 3  | 34 |
| 7 | 0 | 0 | 1 | 0 | 1 | 1 | 1 | 1 | 1 | 0  | 2  | 0  | 1  | 0  | 0  | 9 |
| 8 | 0 | 0 | 1 | 1 | 1 | 1 | 0 | 0 | 0 | 0  | 1  | 1  | 1  | 1  | 1  | 9 |
|   |   |   |   |   |   |   |   |   |   |    |    |    |    |    |    | 124 |

Table 2 depicts the grid of 8 rows by 15 columns. The T (total) per row of the scale numbers of squares in that row is given. The sum of the T for the grid is 124. The total 100% (scale number 3) coverage for an 8×15 grid is 120 0.3=360. Thus, the added total porosity is estimated at 124/360=34%. Thus, for instance, if the total porosity was 25%, this added 34% can mean that the total porosity is increased to 59%. The added total porosity may be the fractured kerogen porosity. The added total porosity may be additional connected porosity.

Figure 13:
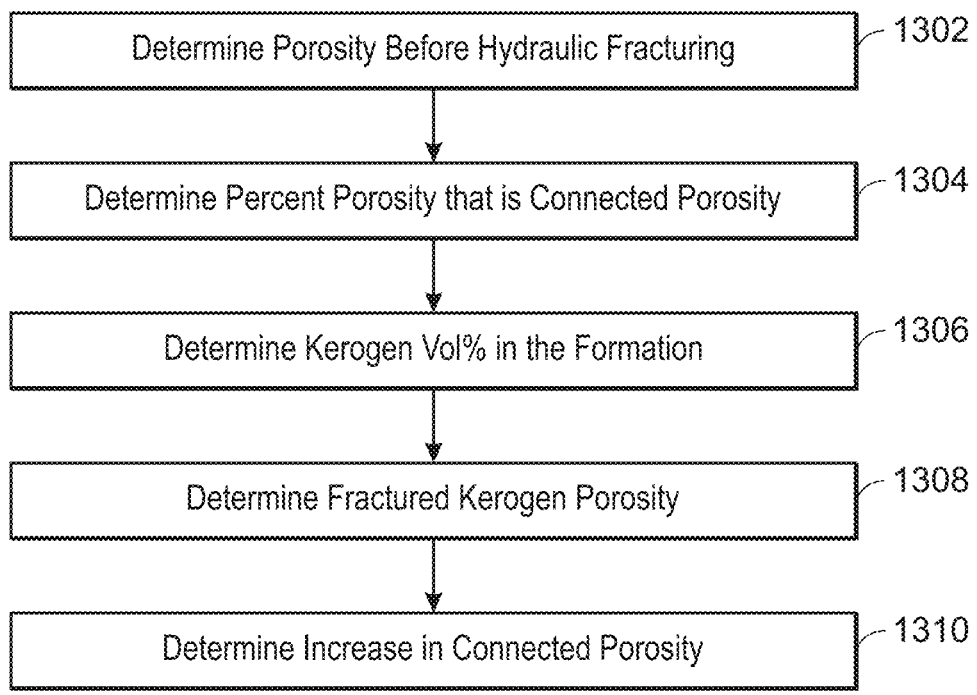
FIG. 13 is a block flow diagram of evaluating treatment effects of oxidative hydraulic fracturing.

FIG. 13 is a method 1300 of evaluating or determining effect of hydraulic fracturing fluid having an oxidizer on a subterranean formation with the oxidative hydraulic fracturing on the subterranean formation. The method can be characterized as estimating enhancement of porosity and/or enhancement of permeability of a subterranean formation due to presence of an oxidizer in a fracturing fluid. The fracturing fluid is utilized in hydraulic fracturing of the subterranean formation.

At block 1302, the method includes determining porosity (e.g., total porosity) of the subterranean formation before the oxidative hydraulic fracturing of the subterranean formation. In other words, this can be the porosity of the subterranean formation before the hydraulic fracturing of the subterranean formation with the hydraulic fracturing fluid having the oxidizer. This subterranean formation porosity (including rock porosity) can be determined, for example, from well log measurements or by laboratory methods, and the like. The values can generally vary from one rock formation to the next. Again, the porosity (before oxidative hydraulic fracturing) may be obtained, for instance, from well logs or from analysis of collected formation samples via standard laboratory methodologies. This porosity may be compared to porosity after the oxidative hydraulic fracturing. As for units of the porosity values, because porosity is a ratio or dimensionless, the units may be porosity units (PU), dimensionless, or %.

At block 1304, the method includes determining the percent of the porosity (from block 1302) of the subterranean formation before oxidative hydraulic fracturing that is connected porosity. The percent of the total porosity that is connected porosity can be determined, for example, via standard laboratory techniques on samples of the subterranean formation collected before oxidative hydraulic fracturing. The connected porosity before oxidative hydraulic fracturing may be equal to the mathematical product of % connected porosity (before oxidative hydraulic fracturing) percent connected porosity after the oxidative hydraulic fracturing.

At block 1306, the method includes determining kerogen vol % in the subterranean formation. The kerogen vol % can be determined based on (correlative with) the kerogen wt % and the kerogen density. Thus, the kerogen vol % may be determined, for example, by determining kerogen wt % in the subterranean formation and determining kerogen density of kerogen in the subterranean formation. Therefore, the method may include estimating kerogen wt % in the subterranean formation. The method may include estimating the kerogen wt % and the kerogen maturity via pyrolysis testing of a sample of the subterranean formation. The method may include estimating kerogen density of kerogen in the subterranean formation based on maturity of the kerogen. In implementations, the estimating of the kerogen density based on the maturity may involve employing an empirical relationship.

At block 1308, the method includes determining (e.g., estimating) fractured kerogen porosity of the subterranean formation as subjected to oxidative hydraulic fracturing. The fractured kerogen porosity is generally associated with presence of the oxidizer. The method may include estimating, via SEM imaging of a sample of the subterranean formation, the fractured kerogen porosity caused by an oxidizer of a fracturing fluid.

The estimating of the fractured kerogen porosity may involve, after oxidative treatment via the oxidizer, imaging (e.g., SEM imaging) a sample of the subterranean formation. The sample may be collected from the subterranean formation before hydraulic fracturing of the subterranean formation with the fracturing fluid having the oxidizer, and the oxidative treatment is performed on the collected sample (e.g., in the laboratory). On the other hand, the sample is collected from the subterranean formation after hydraulic fracturing the subterranean formation with the fracturing fluid having the oxidizer, and thus the oxidative hydraulic fracturing is the oxidative treatment of the sample (before collection). However, again, the estimating of the fractured kerogen porosity may involve imaging a sample of the subterranean formation (before oxidative hydraulic fracturing) with the sample subjected to oxidative treatment (e.g., in the laboratory) via the oxidizer. Indeed, in some implementations, samples are generally not collected from the formation after hydraulic fracturing. Instead, samples are from core sample obtained before the well is completed. In those cases, samples imaged before and after treatment are from laboratory treatment and may be utilized as a proxy for the actual hydraulic fracturing treatment. A core sample may generally be a cylindrical section obtained by drilling with special drills into the subterranean formation, such as with a hollow steel tube or a core drill. In the coring technique, the sample may be pushed more or less intact into the tube.

The method may include estimating the fractured kerogen porosity via imaging a sample of the subterranean formation, wherein the sample is treated with the oxidizer or wherein the subterranean formation is treated with the oxidizer. The imaging can involve image processing to estimate the fractured kerogen porosity. Estimating the fractured kerogen porosity via the imaging may include identifying items of the sample in an image of the sample, wherein the items are caused by the oxidizer. The items may be, for example, pores associated with organic matter caused by attack of the organic matter by the oxidizer. The items may be items in or adjacent organic matter at an external surface of the sample, wherein the items contribute connected porosity. In all, the estimating of the fractured kerogen porosity via the imaging can involve identifying items on the sample in an image of the sample caused by the oxidizer, wherein the items include pores or fractures, or both, in or adjacent organic matter of the sample.

At block 1310, the method includes determining the increase in connected porosity caused by an oxidative hydraulic fracturing. The method may include determining (e.g., estimating) the increase in connected porosity in the subterranean formation correlative with (based on) the kerogen vol % and the fractured kerogen porosity (e.g., due to the oxidizer). The connected porosity after oxidative hydraulic fracturing is a treatment effect and may be equal to the sum of the connected porosity before oxidative hydraulic fracturing plus the mathematical product of the fractured kerogen porosity multiplied by kerogen vol %. Thus, the increase in connected porosity may be the fractured kerogen porosity multiplied by the kerogen vol % (in the formation).

Figure 14:
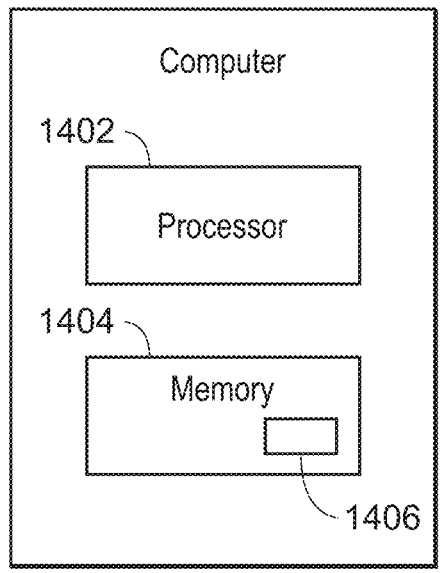
FIG. 14 is a diagram of a computer that implements techniques herein.

FIG. 14 is a computing system 1400 having a processor 1402 and memory 1404 storing code 1406 (e.g., logic, instructions, etc.) executed by the processor 1402. The code 1406 may include the executable components or logic to implement the aforementioned techniques including actions described with respect to (and associated with) the preceding figures. The computing system 1400 may be single computing device, a server, a desktop, a laptop, multiple computing devices or nodes, a distributed computing system, or a control system or component of a control system, or a computer associated with an analytical device or instrument (e.g., SEM). The processor 1402 may be one or more processors and may have one or more cores. The hardware processor(s) 1402 may include a microprocessor, a central processing unit (CPU), a graphics processing unit (GPU), or other circuitry. The memory 1404 may include volatile memory, nonvolatile memory, and firmware. The volatile memory can include, for example, cache or random access memory (RAM). The nonvolatile memory can include, for example, hard drive, solid-state drive, read only memory (ROM), etc. As indicated, the computing system 1400 may be programmed via the code 1406 stored in memory 1404 and executed by the processor 1402 to perform actions discussed throughout the present disclosure including with respect to the figures.

The computing system 1400 improves, for example, the technologies of subterranean formation evaluation, hydraulic fracturing, and the production of hydrocarbons from a subterranean formation. In addition, the computing system 1400 is an improved computing system via the code 1406 in providing for timely evaluations or predictions of oxidative treatment effects on subterranean formations, an in facilitating planning and implementing oxidative hydraulic-fracturing treatments. Such is plainly unconventional, including with respect to the present techniques described herein.

An embodiment a method of estimating enhancement of porosity and permeability of a subterranean formation due to presence of an oxidizer in a fracturing fluid. The fracturing fluid may be utilized in hydraulic fracturing of the subterranean formation. The method includes determining kerogen vol % in the subterranean formation and estimating fractured kerogen porosity, wherein the fractured kerogen porosity is associated with presence of the oxidizer. The method includes determining an increase in connected porosity in the subterranean formation correlative with the kerogen vol % and the fractured kerogen porosity. In implementations, the determining of the kerogen vol % involves determining kerogen wt % in the subterranean formation and determining kerogen density of kerogen in the subterranean formation, wherein the kerogen vol % is correlative with the kerogen wt % and the kerogen density. The method may include estimating kerogen density based on maturity of the kerogen. The method may include estimating the kerogen wt % and the maturity via pyrolysis testing of a sample of the subterranean formation. The estimating of the fractured kerogen porosity may include imaging, after oxidative treatment via the oxidizer, a sample of the subterranean formation. The imaging may be via a scanning electron microscope. In implementations, the oxidative treatment is performed on the sample, wherein the sample is collected from the subterranean formation before hydraulic fracturing of the subterranean formation with the fracturing fluid having the oxidizer, and the oxidative treatment is performed in the laboratory on the sample. In other implementations, the sample is collected from the subterranean formation after hydraulic fracturing the subterranean formation with the fracturing fluid having the oxidizer. In some implementations, samples are generally not collected from the subterranean formation after the oxidative hydraulic fracturing. Instead, samples are obtained from the formation (e.g., from a core sample) collected before the well is completed. In those cases, samples imaged before and after treatment are from laboratory treatment and may be utilized as a proxy for the actual hydraulic fracturing treatment.

Another embodiment is a method of evaluating effect of hydraulic fracturing fluid having an oxidizer on a subterranean formation. The method includes determining porosity of the subterranean formation before hydraulic fracturing the subterranean formation with the hydraulic fracturing fluid comprising the oxidizer, determining percent of the porosity that is connected porosity, and determining an increase in the connected porosity correlative with kerogen vol % in the subterranean formation and fractured kerogen porosity due to the oxidizer. The method may include estimating the fractured kerogen porosity via imaging a sample of the subterranean formation, wherein the sample is treated with the oxidizer or wherein the subterranean formation is treated with the oxidizer. The imaging may include image processing to estimate the fractured kerogen porosity. The estimating of the fractured kerogen porosity via the imaging may include identifying items of the sample in an image of the sample, wherein the items are caused by the oxidizer, and wherein the imaging gives the image. In implementations, the items may include pores associated with organic matter caused by attack of the organic matter by the oxidizer.

Yet another embodiment is a method of determining effect of oxidative hydraulic fracturing on a subterranean formation. The method includes determining porosity of the subterranean formation before the oxidative hydraulic fracturing, determining percent of the porosity that is connected porosity, determining kerogen vol % in the subterranean formation, and estimating, via imaging of a sample of the subterranean formation, fractured kerogen porosity caused by an oxidizer of a fracturing fluid. The imaging may include SEM imaging. The method may include estimating an increase in connected porosity in the subterranean formation based on the kerogen vol % and the fractured kerogen porosity. In implementations, the method includes estimating kerogen wt % in the subterranean formation, and estimating kerogen density of kerogen in the subterranean formation based on maturity of the kerogen, wherein the kerogen vol % is determined based on the kerogen wt % and the kerogen density. The estimating of the kerogen density based on the maturity may involve employing an empirical relationship. The estimating of the fractured kerogen porosity via the imaging may involve identifying items on the sample in an image of the sample caused by the oxidizer, wherein the items include pores or fractures, or both, in or adjacent organic matter of the sample. In implementations, the items include items in or adjacent organic matter at an external surface of the sample, wherein the items contribute connected porosity.

A number of implementations have been described. Nevertheless, it will be understood that various modifications may be made without departing from the spirit and scope of the disclosure.

What is claimed is:

1. A method, comprising:
    determining porosity of a subterranean formation before hydraulic fracturing the subterranean formation with a fracturing fluid that is a hydraulic fracturing fluid comprising an oxidizer;
    determining percent of the porosity that is connected porosity before the hydraulic fracturing;
    determining kerogen volume percent (vol %) in the subterranean formation;
    collecting a sample of the subterranean formation comprising kerogen before the hydraulic fracturing;
    performing oxidative treatment via the oxidizer on the sample;
    estimating, via imaging of the sample, fractured kerogen porosity caused by the oxidizer in the oxidative treatment;
    predicting an increase in the connected porosity in the subterranean formation that would be caused by the hydraulic fracturing of the subterranean formation with the fracturing fluid based on the kerogen vol % of the subterranean formation and the fractured kerogen porosity of the sample caused by the oxidizer in the oxidative treatment of the sample; and
    wherein the fracturing fluid is utilized in hydraulic fracturing of the subterranean formation.

2. The method of claim 1, wherein determining the kerogen vol % comprises determining kerogen weight percent (wt %) in the subterranean formation and determining kerogen density in the subterranean formation, and wherein the kerogen vol % is correlative with the kerogen wt % and the kerogen density.

3. The method of claim 2, wherein determining the kerogen density comprises estimating the kerogen density based on maturity of the kerogen.

4. The method of claim 3, comprising estimating the maturity via pyrolysis testing.

5. The method of claim 1, comprising hydraulic fracturing the subterranean formation with the fracturing fluid.

6. The method of claim 1, wherein determining the kerogen wt % comprises estimating the kerogen wt % via pyrolysis testing.

7. The method of claim 1, wherein estimating, via the imaging of the sample, the fractured kerogen porosity caused by the oxidative treatment performed on the sample comprises identifying pores of the sample in an image of the sample, and wherein the pores are caused by the oxidizer.

8. The method of claim 1, wherein the sample is from a core sample of the subterranean formation collected via a well comprising the wellbore.

9. The method of claim 1, wherein the imaging comprises imaging via a scanning electron microscope.

* * * * *